(12) United States Patent
Kurihara et al.

(10) Patent No.: US 6,255,339 B1
(45) Date of Patent: Jul. 3, 2001

(54) TETRAHYDRONAPHTHOFURANONE DERIVATIVES AND PROCESS FOR PRODUCING THE SAME

(75) Inventors: Kenichi Kurihara; Rie Shinei; Kiyoshi Tanabe; Yasuo Yamamoto; Keiichi Ajito; Kaori Miyajima; Yuji Tabata, all of Yokohama; Shohei Yasuda; Kuniaki Tatsuta, both of Shinjuku-Ku; Tsuneo Okonogi, Yokohama, all of (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 09/117,070

(22) PCT Filed: Feb. 19, 1997

(86) PCT No.: PCT/JP97/00451

§ 371 Date: Jul. 21, 1998

§ 102(e) Date: Jul. 21, 1998

(87) PCT Pub. No.: WO97/30040

PCT Pub. Date: Aug. 21, 1997

(30) Foreign Application Priority Data

Feb. 19, 1996 (JP) ................................... 8-031061
Aug. 28, 1996 (JP) ................................... 8-228005
Dec. 18, 1996 (JP) ................................... 8-338308

(51) Int. Cl.$^7$ .................................................. A61K 31/34
(52) U.S. Cl. ........................................... 514/468; 549/299
(58) Field of Search ............................. 514/468; 549/299

(56) References Cited

FOREIGN PATENT DOCUMENTS 8-253467 10/1996 (JP) .

OTHER PUBLICATIONS

K. Tatsuta et al., *Tetrahedron Letters*, 38(8), 1439–1442 (1997).
Y. Ishizaki et al., *Tetrahedron*, 26(23), 5387–5383 (1970).
A Mericli et al., *Phytochemistry*, 28(4), 1149–1153 (1989).
Y. Tabata et al., *J. Antibiot.*, 50(4), 309–313 (1997).
K. Kurihara et al., *J. Antibiot.*, 50(4), 360–362 (1997).

*Primary Examiner*—Amelia Owens
(74) *Attorney, Agent, or Firm*—Wenderoth, Lind & Ponack, L.L.P.

(57) ABSTRACT

Compounds represented by the following formula (I) and pharmaceutically acceptable salts thereof are disclosed. The compounds have progesterone receptor binding inhibitory activity and, hence, can be used as therapeutic and prophylactic agents for progesterone-related diseases. Specifically, they are useful as abortifacients, oral contraceptive pills, carcinostatic agents for breast cancer and ovarian cancer, therapeutic agents for endometriosis, meningioma, and myeloma, and therapeutic and prophylactic agents for osteoporosis and climacteric disturbance.

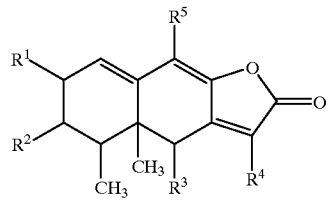

(I)

wherein $R^1$ and $R^2$ represent a hydroxyl group, alkyloxy, alkenyloxy, alkynyloxy, cycloalkyloxy, alkoxyalkyloxy, cycloalkyloxy containig one oxygen atom, aralkyloxy, alkylcarbonyloxy, alkenylcarbonyloxy, alkynylcarbonyloxy, cycloalkylcarbonyloxy, alkoxycarbonyloxy, aryloxy carbonyloxy, aralkylcarbonyloxy, aromatic acyloxy, heteroaromatic acyloxy, saturated heterocyclic carbonyloxy, alkylsulfonyloxy, aromatic sulfonyloxy, alkylcarbamoyloxy, aromatic carbamoyloxy, alkylcarbonylamino, or aromatic acylamino, provided that $R^1$ may further represent a hydrogen atom, alkyl, alkenyl, or alkynyl; and $R^3$, $R^4$, and $R^5$ each independently represent a hydrogen atom, alkyl or alkenyl.

32 Claims, 9 Drawing Sheets

TETRAHYDRONAPHTHOFURANONE DERIVATIVES AND PROCESS FOR PRODUCING THE SAME

BACKGROUND OF THE INVENTION

1. Field of Invention

The present invention relates to compounds having progesterone receptor binding inhibitory activity and pharmaceutical compositions containing the same.

2. Background Art

In recent years, also in Japan, there is a tendency for the number of patients suffering from breast cancer to increase, and it is foreseen that the number of patients suffering from breast cancer would become largest among the malignant tumors in women in the 21st century. Ovariectomy has for the first time been used as endocrinotherapy for breast cancer. Thereafter, adrenalectomy and hypophysectomy have been reported to be useful as therapy for breast cancer in progress, and, since then, surgical endocrinotherapy has been mainly used and made progress. In the surgical endocrinotherapy, an organ involved in the secretion of estrogen is removed to regress estrogen dependent breast cancer. This, however, results in loss of not only estrogen but also life-sustaining hormones, including steroid hormones, posing many problems associated with the quality of life.

Non-steroidal anti-estrogen agents typified by Tamoxifen Citrate which appeared in the latter half of 1970s, by virtue of high effect against breast cancer and much lower side effect than conventional androgen and estrogen, have become extensively applied in clinical investigations and replaced the surgical endocrinotherapy used as main therapy for breast cancer up to that point.

More recently, agents having a new mechanism of action, such as medroxyprogesterone acetate (MPA) ("NYUGAN NO RINSHO", vol. 1, 201–213 (1986)), aromatase inhibitor, luteinizing hormone releasing hormone (LH-RH) agonist ("GAN TO KAGAKU RYOHO", 16, 2729 (1994)) have been developed, resulting in diversified endocrinotherapy for breast cancer.

On the other hand, the treatment of breast cancer with an antiprogesterone agent based on progesterone receptor has been actively attempted particularly in recent years. For example, Mifepristone (RU38486) (FR2497807), Onapristone (ZK98299) (DE3321826) are under development.

Since, however, all of them have a steroidal skeleton, they have been pointed out to have side effect characteristic of steroid. Therefore, in order to overcome these problems, the appearance of an agent having progesterone receptor binding inhibitory activity without the steroid skeleton has been desired in the art.

The present inventors have previously succeeded in isolation of substance PF1092, having inhibitory activity against binding of progesterone to progesterone receptor, from a cultured mixture of a strain belonging to the genus Penicillium (Japanese Patent Application Nos. 20860/1995 and 17074/1996 and EP96100580.8, which are incorporated herein by reference).

SUMMARY OF THE INVENTION

The present inventors have now succeeded in synthesis of various derivatives of substance PF1092 and confirmed that these derivative still have progesterone receptor binding inhibitory activity. The present invention is based on such novel finding.

Thus, according to one aspect of the present invention, there is provided a compound represented by the following formula (I) or a pharmaceutically acceptable salt thereof:

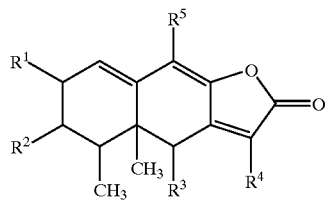

(I)

wherein
$R^1$ represents
a hydroxyl group,
optionally substituted $C_1$–$C_{10}$ alkyloxy,
optionally substituted $C_2$–$C_{10}$ alkenyloxy,
optionally substituted $C_2$–$C_{10}$ alkynyloxy,
$C_3$–$C_6$ cycloalkyloxy,
$C_2$–$C_{12}$ alkoxyalkyloxy,
five- or six-membered cycloalkyloxy containig one oxygen atom,
optionally substituted $C_7$–$C_{15}$ aralkyloxy,
optionally substituted $C_2$–$C_{11}$ alkylcarbonyloxy,
optionally substituted $C_3$–$C_{11}$ alkenylcarbonyloxy,
optionally substituted $C_3$–$C_{11}$ alkynylcarbonyloxy,
$C_4$–$C_{15}$ cycloalkylcarbonyloxy,
$C_2$–$C_{11}$ alkoxycarbonyloxy,
$C_7$–$C_{15}$ aryloxy carbonyloxy,
optionally substituted $C_8$–$C_{15}$ aralkylcarbonyloxy,
optionally substituted $C_7$–$C_{15}$ aromatic acyloxy,
optionally substituted $C_3$–$C_{15}$ heteroaromatic acyloxy having at least one hetero atom selected from the group consisting of nitrogen, oxygen, and sulfur atoms,
optionally substituted $C_4$–$C_{12}$ saturated heterocyclic carbonyloxy having at least one hetero atom selected from the group consisting of nitrogen, oxygen, and sulfur atoms,
$C_1$–$C_6$ alkylsulfonyloxy,
optionally substituted $C_6$–$C_{12}$ aromatic sulfonyloxy,
$C_2$–$C_7$ alkylcarbamoyloxy
optionally substituted $C_7$–$C_{12}$ aromatic carbamoyloxy,
optionally substituted $C_2$–$C_{11}$ alkylcarbonylamino,
optionally substituted $C_7$–$C_{15}$ aromatic acylamino,
a hydrogen atom,
optionally substituted $C_1$–$C_{10}$ alkyl,
optionally substituted $C_2$–$C_{10}$ alkenyl, or
optionally substituted $C_2$–$C_{10}$ alkynyl;
$R^2$ represents
a hydroxyl group,
optionally substituted $C_1$–$C_{10}$ alkyloxy,
optionally substituted $C_2$–$C_{10}$ alkenyloxy,
optionally substituted $C_2$–$C_{10}$ alkynyloxy,
$C_3$–$C_6$ cycloalkyloxy,
$C_2$–$C_{12}$ alkoxyalkyloxy,
five- or six-membered cycloalkyloxy containing one oxygen atom,
optionally substituted $C_7$–$C_{15}$ aralkyloxy,
optionally substituted $C_2$–$C_{11}$ alkylcarbonyloxy,
optionally substituted $C_3$–$C_{11}$ alkenylcarbonyloxy,
optionally substituted $C_3$–$C_{11}$ alkynylcarbonyloxy,
$C_4$–$C_{15}$ cycloalkylcarbonyloxy,
$C_2$–$C_{11}$ alkoxycarbonyloxy,
$C_7$–$C_{15}$ aryloxy carbonyloxy, optionally substituted $C_8$–$C_{15}$ aralkylcarbonyloxy,
optionally substituted $C_7$–$C_{15}$ aromatic acyloxy,
optionally substituted $C_3$–$C_{15}$ heteroaromatic acyloxy having at least one hetero atom selected from the group consisting of nitrogen, oxygen, and sulfur atoms,
optionally substituted $C_4$–$C_{12}$ saturated heterocyclic carbonyloxy having at least one hetero atom selected from the group consisting of nitrogen, oxygen, and sulfur atoms,
$C_1$–$C_6$ alkylsulfonyloxy,
optionally substituted $C_6$–$C_{12}$ aromatic sulfonyloxy,
$C_2$–$C_7$ alkylcarbamoyloxy
optionally substituted $C_7$–$C_{12}$ aromatic carbamoyloxy,
optionally substituted $C_2$–$C_{11}$ alkylcarbonylamino,
optionally substituted $C_7$–$C_{15}$ aromatic acylamino;

$R^3$ represents
a hydrogen atom
optionally substituted $C_1$–$C_{10}$ alkyl, or
optionally substituted $C_2$–$C_{10}$ alkenyl;

$R^4$ represents
a hydrogen atom
optionally substituted $C_1$–$C_{10}$ alkyl, or
optionally substituted $C_2$–$C_{10}$ alkenyl; and $R^5$ represents
a hydrogen atom
optionally substituted $C_1$–$C_{10}$ alkyl, or
optionally substituted $C_2$–$C_{10}$ alkenyl, provided that a compound wherein both $R^1$ and $R^2$ represent a hydroxyl group, $R^3$ and $R^5$ represent a hydrogen atom, and $R^4$ represents methyl, a compound wherein $R^1$ represents methylcarbonyloxy, and $R^2$ represents a hydroxyl group, $R^3$ and $R^5$ represent a hydrogen atom, and $R^4$ represents methyl, a compound wherein $R^1$ represents a hydroxyl group, $R^2$ represent methylcarbonyloxy, $R^3$ and $R^5$ represent a hydrogen atom, and $R^4$ represents methyl are excluded.

According to another aspect of the present invention, there is provided a process for producing a compound represented by the formula (I) according to claim 1, wherein $R^1$ and $R^2$ represent a hydroxyl group, $R^3$ represents a hydrogen atom, $R^4$ represents a hydrogen atom, optionally substituted $C_1$–$C_{10}$ alkyl, or $C_2$–$C_{10}$ alkenyl and $R^5$ represents a hydrogen atom, said process comprising the steps of:

(a) oxidizing the following compound (11):

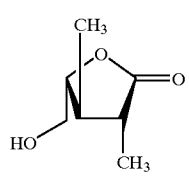

(11)

and then conducting acetal protection;

(b) reacting the resultant compound (12):

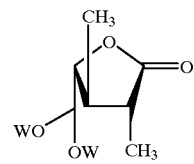

(12)

wherein W is a protective group of an acetal group, with benzenesulfonylmethyl in the presence of a base;

(c) protecting the resultant compound (13):

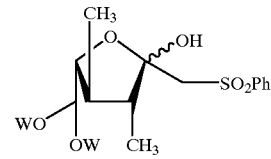

(13)

with a hydroxyl group and then conducting a ring-opening reaction in the presence of a base;

(d) subjecting the resultant compound (14):

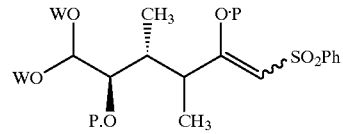

(14)

to a ring-closing reaction with a Lewis acid;

(e) reducing the resultant compound (15):

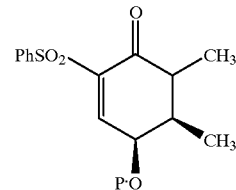

(15)

(f) subjecting the resultant compound (16):

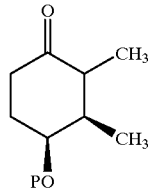

(16)

and 3-trimethylsilyl-3-buten-2-one to Michael addition and cyclocondensation in the presence of a base;

(g) condensing the resultant compound (17):

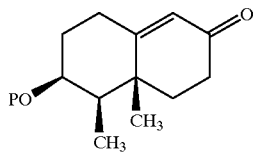
(17)

with α-keto ester by aldol condensation in the presence of a base and optionally a catalytic amount of zinc chloride;

(h) heating the resultant compound (18):

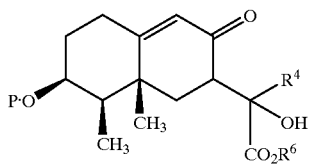
(18)

wherein $R^4$ is as defined above in connection with the formula (I) and $R^6$ is as defined above, under reflux in the presence of an acid catalyst;

(i) oxidizing the resultant compound (19):

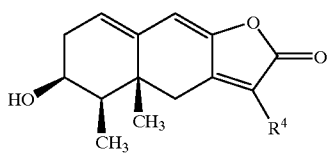
(19)

DETAILED DESCRIPTION OF THE INVENTION

Definition

Figure 1:
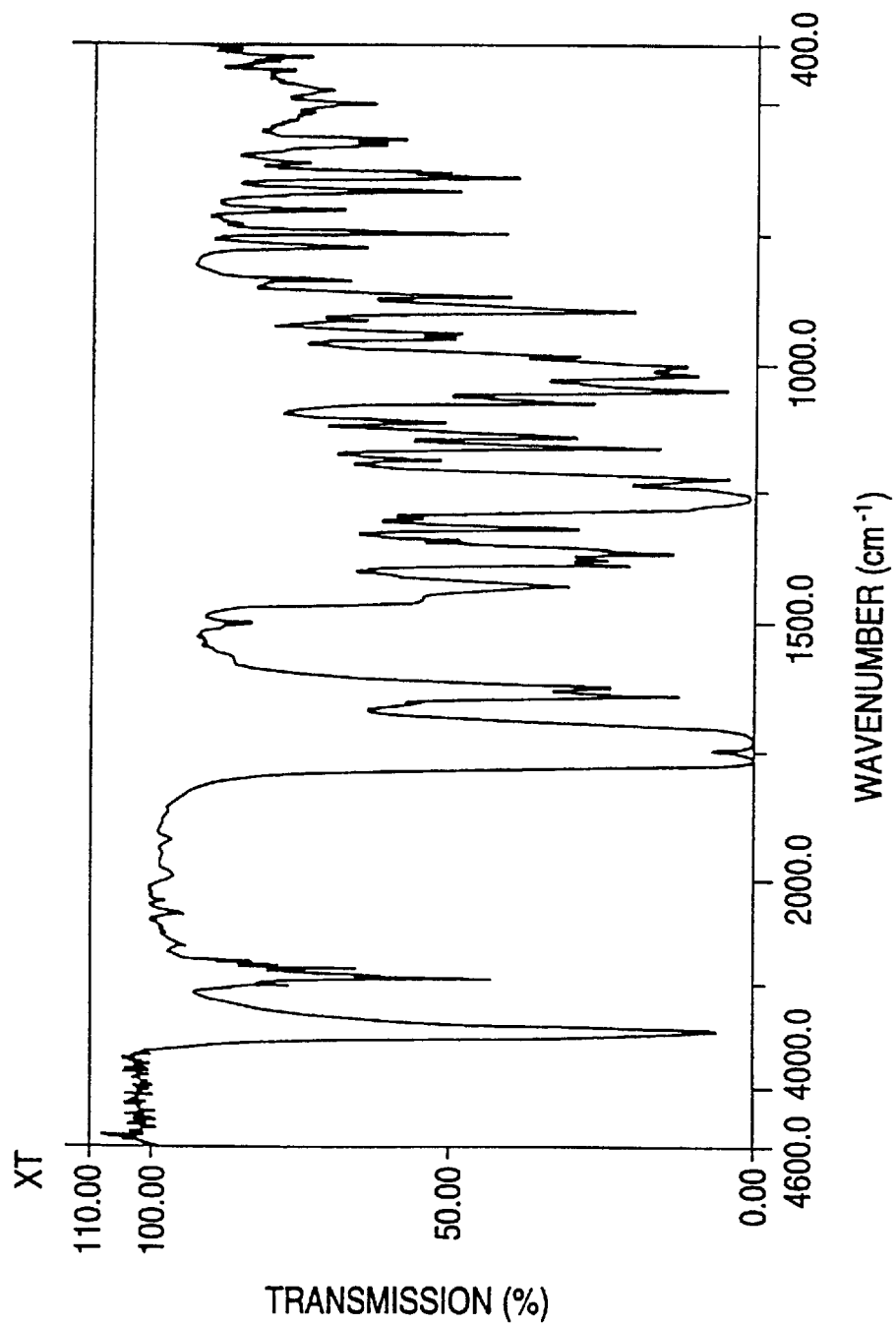
FIG. 1 is a graph showing infrared absorption spectrum of substance PF1092A in KBr tablet.

As used herein, the terms "alkyl," "alkenyl," and "alkynyl" as a group or a part of a group respectively mean straight or branched chain alkyl, alkenyl, and alkynyl. The term "halogen" used herein means a fluorine, chlorine, bromine, or iodine atom. The term "aralkyl" used herein means benzyl, phenylethyl (phenethyl), methylbenzyl, naphthyl or the like. The term "acyl" used herein means alkoxycarbonyl or arylcarbonyl. The term "aryl" preferably means phenyl, naphthyl, tolyl or the like.

Compounds Represented by Formula (I)

In the formula (I), the $C_1-C_{10}$ alkyloxy represented by $R^1$ and $R^2$ is preferably $C_1-C_6$ alkyloxy, more preferably $C_1-C_4$ alkyloxy. At least one hydrogen atom on the alkyloxy may be substituted by a substituent.

The $C_2-C_{10}$ alkenyloxy represented by $R^1$ and $R^2$ is preferably $C_2-C_6$ alkenyloxy, more preferably $C_2-C_4$ alkenyloxy. At least one hydrogen atom on the alkenyloxy may be substituted by a substituent.

The $C_2-C_{10}$ alkynyloxy represented by $R^1$ and $R^2$ is preferably $C_2-C_6$ alkynyloxy, more preferably $C_2-C_{10}$ alkynyloxy. At least one hydrogen atom on the alkynyloxy may be substituted by a substituent.

Examples of the $C_3-C_6$ cycloalkyloxy represented by $R^1$ and $R^2$ include cyclopropyloxy, cyclobutyloxy, cyclopentyloxy, and cyclohexyloxy.

The $C_2-C_{12}$ alkoxyalkyloxy represented by $R^1$ and $R^2$ is preferably $C_1-C_6$ alkoxy $C_1-C_6$ alkyloxy, more preferably $C_1-C_4$ alkoxy $C_1-C_4$ alkyloxy. Examples of the $C_7-C_{15}$ aralkyloxy represented by $R^1$ and $R^2$ include benzyloxy, phenylethyloxy, methylbenzyloxy, and naphthylmethyloxy.

The $C_2-C_{11}$ alkylcarbonyloxy represented by $R^1$ and $R^2$ is preferably $C_2-C_7$ alkylcarbonyloxy, more preferably $C_2-C_5$ alkylcarbonyloxy. At least one hydrogen atom on the alkylcarbonyloxy may be substituted by a substituent.

The five- or six-membered cycloalkyloxy containing one oxygen atom, represented by $R^1$ and $R^2$, includes tetrahydrofuryloxy and tetrahydropyranyloxy.

The $C_3-C_{11}$ alkenylcarbonyloxy represented by $R^1$ and $R^2$ is preferably $C_3-C_7$ alkenylcarbonyloxy, more preferably $C_3-C_5$ alkenylcarbonyloxy. At least one hydrogen atom on the alkenylcarbonyloxy may be substituted by a substituent.

The $C_3-C_{11}$ alkynylcarbonyloxy represented by $R^1$ and $R^2$ is preferably $C_3-C_7$ alkynylcarbonyloxy, more preferably $C_3-C_5$ alkynylcarbonyloxy. At least one hydrogen atom on the alkynylcarbonyloxy may be substituted by a substituent.

The $C_4-C_{15}$ cycloalkylcarbonyloxy represented by $R^1$ and $R^2$ is preferably $C_4-C_8$ cycloalkylcarbonyloxy, and examples thereof include cyclopropylcarbonyloxy, cyclobutylcarbonyloxy, cyclopentylcarbonyloxy, and cyclohexylcarbonyloxy.

The $C_2-C_{11}$ alkoxycarbonyloxy represented by $R^1$ and $R^2$ is preferably $C_2-C_7$ alkoxycarbonyloxy, more preferably $C_2-C_5$ alkoxycarbonyloxy.

Examples of the $C_7-C_{15}$ aryloxy carbonyloxy represented by $R^1$ and $R^2$ include phenycarbonyloxy, naphthylcarbonyloxy, and tricarbonyloxy.

Examples of the $C_8-C_{15}$ aralkylcarbonyloxy represented by $R^1$ and $R^2$ include benzylcarbonyloxy, phenylethylcarbonyloxy, methylbenzylcarbonyloxy, and naphthylmethylcarbonyloxy. At least one hydrogen atom on the aralkylcarbonyloxy may be substituted by a substituent.

Examples of the $C_7-C_{15}$ aromatic acyloxy represented by $R^1$ and $R^2$ include benzoyloxy, trioyloxy, cinnamoyloxy, and naphthoyloxy. At least one hydrogen atom on the aromatic acyloxy may be substituted by a substituent.

The $C_3-C_{15}$ heteroaromatic acyloxy, having at least one hetero atom selected from the group consisting of nitrogen, oxygen, and sulfur atoms, represented by $R^1$ and $R^2$ is preferably a five- or six-membered heteroaromatic acyloxy group containing one oxygen or sulfur atom, for example, furoyloxy, pyranylcarbonyloxy, or thenoyloxy, or a five- or six-membered heteroaromatic acyloxy group containing a nitrogen atom and a sulfur atom, for example, thiazolylcarbonyloxy. The heteroaromatic ring, together with other ring, for example, a benzene ring, may form a condensed ring, and examples thereof include benzothiophene. At least one hydrogen atom on the heteroaromatic acyloxy may be substituted by a substituent, and examples of the substituent include $C_1-C_6$ alkyl.

Examples of the $C_4-C_{12}$ saturated heterocyclic carbonyloxy, having at least one hetero atom selected from the group consisting of nitrogen, oxygen, and sulfur atoms, represented by $R^1$ and $R^2$ include tetrahydrofurylcarbonyloxy and tetrahydropyranylcarbonyloxy. At least one hydrogen atom on the saturated heterocyclic carbonyloxy may be substituted by a substituent.

The $C_1-C_6$ alkylsulfonyloxy represented by $R^1$ and $R^2$ is preferably $C_1-C_4$ alkylsulfonyloxy.

Examples of the $C_6-C_{12}$ aromatic sulfonyloxy represented by $R^1$ and $R^2$ include phenylsulfonyloxy. At least one hydrogen atom on the aromatic sulfonyloxy may be substituted by a substituent.

The $C_2-C_7$ alkylcarbamoyloxy represented by $R^1$ and $R^2$ is preferably $C_2-C_5$ alkylcarbamoyloxy.

Examples of the $C_7-C_{12}$ aromatic carbamoyloxy represented by $R^1$ and $R^2$ include phenylcarbamoyloxy. At least one hydrogen atom on the aromatic carbamoyloxy may be substituted by a substituent.

The $C_1-C_{10}$ alkyl represented by $R^1$ and $R^2$ is preferably $C_1-C_6$ alkyl, more preferably $C_1-C_4$ alkyl. At least one hydrogen atom on the alkyl may be substituted by a substituent.

The $C_2-C_{10}$ alkenyl represented by $R^1$ and $R^2$ is preferably $C_2-C_6$ alkenyl, more preferably $C_2-C_4$ alkenyl. At least one hydrogen atom on the alkenyl may be substituted by a substituent.

The $C_2-C_{10}$ alkynyl represented by $R^1$ and $R^2$ is preferably $C_2-C_6$ alkynyl, more preferably $C_2-C_4$ alkynyl. At least one hydrogen atom on the alkynyl may be substituted by a substituent.

In the formula (I), the $C_1-C_{10}$ alkyl represented by $R^3$ is preferably $C_1-C_6$ alkyl, more preferably $C_1-C_4$ alkyl. At least one hydrogen atom on the alkyl may be substituted by a substituent.

The $C_2-C_{10}$ alkenyl represented by $R^3$ is preferably $C_2-C_6$ alkenyl, more preferably $C_2-C_4$ alkenyl. At least one hydrogen atom on the alkenyl may be substituted by a substituent.

In the formula (I), the $C_1-C_{10}$ alkyl represented by $R^4$ is preferably $C_1-C_6$ alkyl, more preferably $C_1-C_4$ alkyl. At least one hydrogen atom on the alkyl may be substituted by a substituent.

The $C_2-C_{10}$ alkenyl represented by $R^4$ is preferably $C_2-C_6$ alkenyl, more preferably $C_2-C_4$ alkenyl. At least one hydrogen atom on the alkenyl may be substituted by a substituent.

In the formula (I), the $C_1-C_{10}$ alkyl represented by $R^5$ is preferably $C_1-C_6$ alkyl, more preferably $C_1-C_4$ alkyl. At least one hydrogen atom on the alkyl may be substituted by a substituent.

The $C_2-C_{10}$ alkenyl represented by $R^5$ is preferably $C_2-C_6$ alkenyl, more preferably $C_2-C_4$ alkenyl. At least one hydrogen atom on the alkenyl may be substituted by a substituent.

The compound according to the present invention are represented by the formula (I). However, a compound wherein both $R^1$ and $R^2$ represent a hydroxyl group, $R^3$ and $R^5$ represent a hydrogen atom, and $R^4$ represents methyl (sometimes referred to as "substance PF1092C"), a compound wherein $R^1$ represents methylcarbonyloxy, and $R^2$ represents a hydroxyl group, $R^3$ and $R^5$ represent a hydrogen atom, and $R^4$ represents methyl (sometimes referred to as "substance PF1092B"), a compound wherein $R^1$ represents a hydroxyl group, $R^2$ represents methylcarbonyloxy, $R^3$ and $R^5$ represent a hydrogen atom, and $R^4$ represents methyl (sometimes referred to as "substance PF1092A") are excluded from the scope of the present invention.

Among the compounds represented by the formula (I) according to the present invention, the following groups of compounds are preferred.

Specifically, a group of preferred compounds are those represented by the formula (I) wherein $R^1$ represents
  a hydroxyl group,
  $C_1-C_{10}$ alkyloxy,
  $C_3-C_6$ cycloalkyloxy,
  $C_2-C_{12}$ alkoxyalkyloxy,
  optionally substituted $C_7-C_{15}$ aralkyloxy,
  optionally substituted $C_2-C_{11}$ alkylcarbonyloxy,
  $C_4-C_{15}$ cycloalkylcarbonyloxy,
  $C_2-C_{11}$ alkoxycarbonyloxy,
  $C_7-C_{15}$ aryloxy carbonyloxy,
  optionally substituted $C_8-C_{15}$ aralkylcarbonyloxy,
  optionally substituted $C_7-C_{15}$ aromatic acyloxy,
  optionally substituted $C_3-C_{15}$ heteroaromatic acyloxy having at least one hetero atom selected from the group consisting of nitrogen, oxygen, and sulfur atoms,
  optionally substituted $C_4-C_{12}$ saturated heterocyclic carbonyloxy having at least one hetero atom selected from the group consisting of nitrogen, oxygen, and sulfur atoms,
  $C_1-C_6$ alkylsulfonyloxy,
  $C_2-C_7$ alkylcarbamoyloxy
  optionally substituted $C_7-C_{12}$ aromatic carbamoyloxy,
  optionally substituted $C_2-C_{11}$ alkylcarbonylamino,
  a hydrogen atom, or
  optionally substituted $C_1-C_{10}$ alkyl;
$R^2$ represents a hydroxyl group;
$R^3$ represents
  a hydrogen atom or
  optionally substituted $C_1-C_{10}$ alkyl;
$R^4$ represents
  a hydrogen atom or
  optionally substituted $C_1-C_{10}$ alkyl; and
$R^5$ represents
  a hydrogen atom or
  optionally substituted $C_1-C_{10}$ alkyl.

Another group of preferred compounds are those represented by the formula (I) wherein $R^1$ represents a hydroxyl group;
$R^2$ represents
  a hydroxyl group,
  $C_1-C_{10}$ alkyloxy,
  $C_3-C_6$ cycloalkyloxy, $C_2$–$C_{12}$ alkoxyalkyloxy,
optionally substituted $C_7$–$C_{15}$ aralkyloxy,
optionally substituted $C_2$–$C_{11}$ alkylcarbonyloxy,
$C_4$–$C_{15}$ cycloalkylcarbonyloxy,
$C_2$–$C_{11}$ alkoxycarbonyloxy,
$C_7$–$C_{15}$ aryloxy carbonyloxy,
optionally substituted $C_8$–$C_{15}$ aralkylcarbonyloxy,
optionally substituted $C_7$–$C_{15}$ aromatic acyloxy,
optionally substituted $C_3$–$C_{15}$ heteroaromatic acyloxy having at least one hetero atom selected from the group consisting of nitrogen, oxygen, and sulfur atoms,
optionally substituted $C_4$–$C_{12}$ saturated heterocyclic carbonyloxy having at least one hetero atom selected from the group consisting of nitrogen, oxygen, and sulfur atoms,
$C_1$–$C_6$ alkylsulfonyloxy,
$C_2$–$C_7$ alkylcarbamoyloxy
optionally substituted $C_7$–$C_{12}$ aromatic carbamoyloxy,
optionally substituted $C_2$–$C_{11}$ alkylcarbonylamino,
a hydrogen atom, or
optionally substituted $C_1$–$C_{10}$ alkyl;
$R^3$ represents
a hydrogen atom or
optionally substituted $C_1$–$C_{10}$ alkyl;
$R^4$ represents
a hydrogen atom or
optionally substituted $C_1$–$C_{10}$ alkyl; and
$R^5$ represents
a hydrogen atom or
optionally substituted $C_1$–$C_{10}$ alkyl.
Still another group of preferred compounds are those represented by the formula (I) wherein
$R^1$ and $R^2$ each independently represent
a hydroxyl group;
$C_1$–$C_{10}$ alkyloxy,
$C_3$–$C_6$ cycloalkyloxy,
$C_2$–$C_{12}$ alkoxyalkyloxy,
optionally substituted $C_7$–$C_{15}$ aralkyloxy,
optionally substituted $C_2$–$C_{11}$ alkylcarbonyloxy,
$C_4$–$C_{15}$ cycloalkylcarbonyloxy,
$C_2$–$C_{11}$ alkoxycarbonyloxy,
$C_7$–$C_{15}$ aryloxy carbonyloxy,
optionally substituted $C_8$–$C_{15}$ aralkylcarbonyloxy,
optionally substituted $C_7$–$C_{15}$ aromatic acyloxy,
optionally substituted $C_3$–$C_{15}$ heteroaromatic acyloxy having at least one hetero atom selected from the group consisting of nitrogen, oxygen, and sulfur atoms,
optionally substituted $C_4$–$C_{12}$ saturated heterocyclic carbonyloxy having at least one hetero atom selected from the group consisting of nitrogen, oxygen, and sulfur atoms,
$C_1$–$C_6$ alkylsulfonyloxy,
$C_2$–$C_7$ alkylcarbamoyloxy
optionally substituted $C_7$–$C_{12}$ aromatic carbamoyloxy,
optionally substituted $C_2$–$C_{11}$ alkylcarbonylamino,
a hydrogen atom, or
optionally substituted $C_1$–$C_{10}$ alkyl;
$R^3$ represents
a hydrogen atom or
optionally substituted $C_1$–$C_{10}$ alkyl;
$R^4$ represents
a hydrogen atom or
optionally substituted $C_1$–$C_{10}$ alkyl; and
$R^5$ represents
a hydrogen atom or
optionally substituted $C_1$–$C_{10}$ alkyl.
A further group of preferred compounds are those prepared by the formula (I) wherein
$R^1$ represents a hydrogen atom;
$R^2$ represents
a hydroxyl group,
$C_2$–$C_{10}$ alkylcarbonyloxy,
$C_3$–$C_{10}$ alkenylcarbonyloxy,
optionally substituted $C_2$–$C_{10}$ alkylcarbonyloxy,
$C_4$–$C_{15}$ cycloalkylcarbonyloxy,
optionally substituted $C_8$–$C_{15}$ aralkylcarbonyloxy,
optionally substituted $C_7$–$C_{15}$ aromatic acyloxy, or
optionally substituted $C_3$–$C_{15}$ heteroaromatic acyloxy having at least one nitrogen, oxygen, or sulfur atom;
$R^3$ represents
a hydrogen atom
optionally substituted $C_1$–$C_{10}$ alkyl, or
optionally substituted $C_2$–$C_{10}$ alkenyl;
$R^4$ represents
a hydrogen atom,
$C_1$–$C_{10}$ alkyl,
optionally substituted $C_1$–$C_{10}$ alkyl,
optionally substituted $C_2$–$C_{10}$ alkenyl; and
$R^5$ represents
a hydrogen atom
optionally substituted $C_1$–$C_{10}$ alkyl, or
optionally substituted $C_2$–$C_{10}$ alkenyl.
A group of more preferred compounds represented by the formula (I) include:
compounds wherein
$R^2$ represents 2-tetrahydropyranyloxy, propionyloxy, isobutyryloxy, chloroacetyloxy, phenylacetyloxy, cyclopropylcarbonyloxy, cyclohexylcarbonyloxy, cinnamoyloxy, benzoyloxy, 4-nitrobenzoyloxy, 2-thenoyloxy, 2-furoyloxy, 1-benzothiophen-2-ylcarbonyloxy, 4-methyl-5-thiazolylcarbonyloxy, n-propylcarbamoyloxy, or acetylamino and
$R^1$ represents a hydroxyl group;
compounds wherein
$R^2$ represents methoxy, acetyloxy, propionyloxy, cyclopropylcarbonyloxy, benzoyloxy, 2-thenoyloxy, 2-furoyloxy, ethoxycarbonyloxy, phenoxycarbonyloxy, methylsulfonyloxy, or acetylamino and
$R^1$ represents methoxy;
compounds wherein
$R^2$ represents acetyloxy, propionyloxy, cyclopropylcarbonyloxy, benzoyloxy, 2-thenoyloxy, or 2-furoyloxy and
$R^1$ represents ethoxy;
compounds wherein
$R^2$ represents acetyloxy, propionyloxy, cyclopropylcarbonyloxy, benzoyloxy, 2-thenoyloxy, or 2-furoyloxy and
$R^1$ represents n-propyloxy;
compounds wherein
$R^2$ represents a hydroxyl group, acetyloxy, propionyloxy, cyclopropylcarbonyloxy, benzoyloxy, 2-furoyloxy, 2-thenoyloxy, or methoxymethyloxy and
$R^1$ represents propionyloxy;
compounds wherein
$R^2$ represents a hydroxyl group,
$R^1$ represents benzyloxy, cyclopropylcarbonyloxy, cyclohexylcarbonyloxy, benzoyloxy, 4-nitrobenzoyloxy, 2-thenoyloxy, 2-furoyloxy, methylcarbamoyloxy, or n-propylcarbamoyloxy;
compounds wherein
- $R^2$ represents 2-furoyloxy and
- $R^1$ represents acetyloxy, cyclopropylcarbonyloxy, benzoyloxy, 2-thenoyloxy, or 2-furoyloxy;

compounds wherein
- $R^2$ represents propionyloxy and
- $R^1$ represents acetyloxy, cyclopropylcarbonyloxy, benzoyloxy, 2-thenoyloxy, or 2-furoyloxy;

compounds wherein
- $R^2$ represents benzoyloxy and
- $R^1$ represents methoxymethyloxy or methoxyethoxymethyloxy;

compounds wherein
- $R^2$ represents methoxymethyloxy and
- $R^1$ represents benzoyloxy; and compounds wherein $R^2$ represents n-propylcarbamoyloxy and
- $R^1$ represents n-propylcarbamoyloxy;

compounds wherein
- $R^2$ represents phenylcarbamoyloxy and
- $R^1$ represents phenylcarbamoyloxy.

Further, according to a preferred embodiment of the present invention, groups of preferred compounds represented by the formula (I) include:

compounds wherein
- $R^1$ represents a hydrogen atom,
- $R^2$ represents a hydroxyl group, acetyloxy, propionyloxy, butyryloxy, isobutyryloxy, isovaleryloxy, benzoyloxy, 2-furoyloxy, or 2-thenoyloxy,
- $R^3$ represents a hydrogen atom,
- $R^4$ represents methyl, and
- $R^5$ represents a hydrogen atom;

compounds wherein
- $R^1$ represents a hydrogen atom,
- $R^2$ represents a hydroxyl group, acetyloxy, propionyloxy, butyryloxy, isobutyryloxy, isovaleryloxy, benzoyloxy, 2-furoyloxy, or 2-thenoyloxy,
- $R^3$ represents a hydrogen atom,
- $R^4$ represents methyl, and
- $R^5$ represents methyl;

compounds wherein
- $R^1$ represents a hydrogen atom,
- $R^2$ represents a hydroxyl group, acetyloxy, propionyloxy, butyryloxy, isobutyryloxy, isovaleryloxy, benzoyloxy, 2-furoyloxy, or 2-thenoyloxy,
- $R^3$ represents a hydrogen atom,
- $R^4$ represents ethyl, and
- $R^5$ represents a hydrogen atom;

compounds wherein
- $R^1$ represents a hydrogen atom,
- $R^2$ represents a hydroxyl group, acetyloxy, propionyloxy, butyryloxy, isobutyryloxy, isovaleryloxy, benzoyloxy, 2-furoyloxy, or 2-thenoyloxy,
- $R^3$ represents a hydrogen atom,
- $R^4$ represents a hydrogen atom, and
- $R^5$ represents a hydrogen atom;

compounds wherein
- $R^1$ represents a hydrogen atom,
- $R^2$ represents a hydroxyl group, acetyloxy, propionyloxy, butyryloxy, isobutyryloxy, isovaleryloxy, benzoyloxy, 2-furoyloxy, or 2-thenoyloxy,
- $R^3$ represents methyl,
- $R^4$ represents methyl, and
- $R^5$ represents a hydrogen atom; and compounds wherein
- $R^1$ represents methyl,
- $R^2$ represents a hydroxyl group, acetyloxy, propionyloxy, butyryloxy, isobutyryloxy, isovaleryloxy, benzoyloxy, 2-furoyloxy, or 2-thenoyloxy,
- $R^3$ represents a hydrogen atom,
- $R^4$ represents methyl, and
- $R^5$ represents a hydrogen atom.

According to another embodiment of the present invention, the following group of compounds may be mentioned as a group of preferred compounds. Specifically, preferred are a group of compounds represented by the formula (I) wherein
- $R^1$ and $R^2$ each independently represent
  - a hydroxyl group,
  - optionally substituted $C_1$–$C_{10}$ alkyloxy,
  - optionally substituted $C_2$–$C_{10}$ alkenyloxy,
  - optionally substituted $C_2$–$C_{10}$ alkynyloxy,
  - $C_3$–$C_6$ cycloalkyloxy,
  - $C_2$–$C_{12}$ alkoxyalkyloxy,
  - five- or six-membered cycloalkyloxy containing one oxygen atom,
  - optionally substituted $C_7$–$C_{15}$ aralkyloxy,
  - optionally substituted $C_2$–$C_{11}$ alkylcarbonyloxy,
  - optionally substituted $C_3$–$C_{11}$ alkenylcarbonyloxy,
  - optionally substituted $C_3$–$C_{11}$ alkynylcarbonyloxy,
  - $C_4$–$C_{15}$ cycloalkylcarbonyloxy,
  - $C_2$–$C_{11}$ alkoxycarbonyloxy,
  - $C_7$–$C_{15}$ aryloxy carbonyloxy,
  - optionally substituted $C_8$–$C_{15}$ aralkylcarbonyloxy,
  - optionally substituted $C_7$–$C_{15}$ aromatic acyloxy,
  - optionally substituted $C_3$–$C_{15}$ heteroaromatic acyloxy having at least one hetero atom selected from the group consisting of nitrogen, oxygen, and sulfur atoms,
  - optionally substituted $C_4$–$C_{12}$ saturated heterocyclic carbonyloxy having at least one hetero atom selected from the group consisting of nitrogen, oxygen, and sulfur atoms,
  - $C_1$–$C_6$ alkylsulfonyloxy,
  - optionally substituted $C_6$–$C_{12}$ aromatic sulfonyloxy,
  - $C_2$–$C_7$ alkylcarbamoyloxy
  - optionally substituted $C_7$–$C_{12}$ aromatic carbamoyloxy,
  - optionally substituted $C_2$–$C_{11}$ alkylcarbonylamino;
- $R^3$ represents a hydrogen atom;
- $R^4$ represents
  - a hydrogen atom or
  - $C_1$–$C_{10}$ alkyl; and
- $R^5$ represents a hydrogen atom.

Among the above groups of compounds, a group of more preferred compounds are those wherein
- $R^1$ and $R^2$ each independently represent
  - a hydroxyl group,
  - $C_1$–$C_6$ alkyloxy group,
  - $C_2$–$C_{12}$ alkoxyalkyloxy which may be substituted by $C_1$–$C_6$ alkoxy group,
  - $C_7$–$C_{15}$ aralkyloxy,
  - $C_2$–$C_7$ alkylcarbonyloxy which may be substituted by a halogen,
  - $C_4$–$C_{15}$ cycloalkylcarbonyloxy,
  - $C_2$–$C_7$ alkoxycarbonyloxy,
  - $C_7$–$C_{15}$ aryloxycarbonyloxy, $C_8$–$C_{15}$ aralkylcarbonyloxy,
$C_7$–$C_{15}$ arylcarbonyloxy which may be substituted by nitro,
five- or six-membered heteroaromatic acyloxy containing one oxygen or sulfur atom,
five- or six-membered heteroaromatic acyloxy, containing a nitrogen or sulfur atom, which may be substituted by $C_1$–$C_6$ alkyl,
five- or six-membered saturated heterocyclic carbonyloxy having at least one hetero atom selected from nitrogen, oxygen, and sulfur atoms,
$C_1$–$C_6$ alkylsulfonyloxy,
$C_2$–$C_7$ alkylcarbamoyloxy,
$C_7$–$C_{12}$ arylcarbamoyloxy,
$C_2$–$C_7$ alkylcarbonylamino:

$R^3$ represents a hydrogen atom;

$R^4$ represents $C_1$–$C_6$ alkyl; and $R^5$ represents a hydrogen atom.

Since the compounds represented by the formula (I) according to the present invention have several asymmetric carbons, various isomers attributable to these carbons are considered. The present invention embraces these individual isomers and mixtures thereof.

The compounds represented by the formula (I) may be present in the form of a salt. Examples of the salt include pharmacologically acceptable salts, and specific examples thereof include lithium, sodium, potassium, magnesium, and calcium salts; salts with ammonium and suitable non-toxic amines, for example, $C_1$–$C_6$ alkylamine (for example, triethylamine) salts, $C_1$–$C_6$ alkanolamine (for example, diethanolamine or triethanolamine) salts, procaine salts, cyclohexylamine (for example, dicyclohexylamine) salts, benzylamine (for example, N-methylbenzylamine, N-ethylbenzylamine, N-benzyl-β-phenethylamine, N,N-dibenzylethylenediamine, or dibenzylamine) salts, and heterocyclic amines (for example, morpholine or N-ethylpyridine) salts; salts of hydrohalogenic acids such as hydrofluoric acid, hydrochloric acid, hydrobromic acid and hydroiodic acid; inorganic acid salts such as sulfate, nitrate, phosphate, perchlorate and carbonate; salts of carboxylic acids such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid and malic acid; salts of amino acids such as arginic acid, aspartic acid and glutamic acid; and salts of organic acids such as methanesulfonic acid and p-toluenesulfonic acid.

Use of Compounds Represented by Formula (I)/Pharmaceutical Compositions

The compounds, represented by the formula (I), according to the present invention have progesterone receptor binding inhibitory activity and, hence, can be used as therapeutic and prophylactic agents for progesterone-related diseases. The progesterone receptor has been reported to be expressed in breast, uterus, ovary, bone, central nerve and the like. Therefore, the compounds represented by the formula (I) are useful as therapeutic and prophylactic agents for progesterone-related diseases in these organs. More specifically, they are useful as abortifacients, oral contraceptive pills, carcinostatic agents for breast cancer and ovarian cancer, therapeutic agents for endometriosis, meningioma, and myeloma, and therapeutic and prophylactic agents for osteoporosis and climacteric disturbance. Especially, the compounds represented by the formula (I) according to the present invention have no steroid skeleton and, hence, are considered to be advantageously free from side effect inherent in steroid such as found in conventional progesterone receptor binding inhibitors having a steroid skeleton.

A pharmaceutical composition comprising as an active ingredient a compound of the present invention can be administered either orally or parenterally (e.g., intravenous injection, intramuscular injection, subcutaneous administration, rectal administration, percutaneous administration) to humans or animals other than humans.

The pharmaceutical composition comprising as an active ingredient a compound of the present invention may be made into a preparation suitable for an administration route to be adopted. Specifically, it may be made into any of the following preparations: an injection for intravenous or intramuscular injection; a capsule, a tablet, a granule, a powder, a pill, fine subtilaes, or a troche for oral administration; a preparation for rectal administration; an oleaginous suppository; and an aqueous suppository. The above-described various preparations can be prepared by a conventional method using an excipient, a filler, a binder, a wetting agent, a disintegrating agent, a surface active agent, a lubricant, a dispersing agent, a buffer, a preservative, a solubilizer, an antiseptic, a flavor, a soothing agent, a stabilizer and the like. Examples of the above additives which are nontoxic and employable in the preparations include milk sugar, fruit sugar, grape sugar, starch, gelatin, magnesium carbonate, synthetic magnesium silicate, talc, magnesium stearate, methyl cellulose, carboxymethyl cellulose or a salt thereof, gum arabic, polyethylene glycol, syrup, vaseline, glycerin, ethanol, propylene glycol, citric acid, sodium chloride, sodium sulfite and sodium phosphate.

The dosage of the compound of the present invention is properly determined in consideration of the symptom and the age and sex of a patient for each case. However, for the treatment of the above diseases, in particular, as a contraceptive pill or an carcinostatic agent for breast cancer or ovarian cancer, in case of intravenous injection, 0.01 mg/kg to 1000 mg/kg, preferably 0.1 mg/kg to 100 mg/kg of the compound is generally administered per day for adult human, desirably at one time or several times. In case of intramuscular injection, 0.01 mg/kg to 1000 mg/kg, preferably 0.1 mg/kg to 100 mg/kg of the compound is generally administered per day for adult human, desirably at one time or several times. In case of oral administration, 0.5 mg/kg to 2000 mg/kg, preferably 1 mg/kg to 1000 mg/kg of the compound is generally administered per day for adult human, desirably at one time or several times.

Preparation of Compound Represented by Formula (I)

Preferably, the compounds represented by the formula (I) according to the present invention can be prepared by the following processes.

The compound represented by the formula (I) according to the present invention can be prepared by providing substance PF1092C as a starting compound and modifying the starting compound.

(a) Acylation of Hydroxyl Group at 6- and 7-positions

Substance PF1092C has a free secondary hydroxyl group at its 6- and 7-positions. One of them is a hydroxyl group at the position of allyl. Therefore, a substituent may be selectively introduced by taking advantage of a difference in reactivity.

Specifically, substance PF1092C may be reacted with a reagent capable of acylating a hydroxyl group, such as an acid halide or an acid anhydride, in the presence of an equivalent or excess amount of a base to acylate the hydroxyl group at the 6- and 7-positions. Either or both of the hydroxyl groups may be selectively acylated by selection of the reagent, the amount of the reagent added, the reaction temperature, and the reaction time.

Selective introduction of an acyl group into the hydroxyl group at the 7-position may be carried out by reacting substance PF1092C with one to three equivalents of an acylating agent in a solvent inert to the reaction (for example, methylene chloride, chloroform, 1,2-dichloroethane, benzene, or toluene) in the presence of one to three equivalents of a suitably bulky organic base (for example, diisopropylethylamine, isopropylcyclohexylamine or the like with one to three equivalents of diisopropylethylamine being preferred) at 20 to 30° C. for 1 to 24 hr.

Selective introduction of an acyl group into the hydroxyl group at the 6-position may be carried out by any of the following two methods.

The first method is to react substance PF1092C with one to three equivalents of an acylating agent $R^{1*}COX$, wherein $R^{1*}$ and X are as defined above, in a solvent inert to the reaction (for example, methylene chloride, chloroform, 1,2-dichloroethane, benzene, or toluene) in the presence of 1 to 1.5 equivalents of an organic base (for example, 4-dimethylaminopyridine, lutidine, or collidine with 1 to 1.5 equivalents of 4-dimethylaminopyridine being preferred) at 20 to 30° C. for 1 to 24 hr.

The second method is a method, utilizing a silyl protective group, wherein after protection of the hydroxyl group at the 7-position with a silyl group, the hydroxyl group at the 6-position is acylated and, in the final stage, the protective group is removed. More specifically, substance PF1092C is reacted with an equivalent or excess amount of a silylating agent in a solvent (for example, dimethylformamide, acetonitrile, methylene chloride, chloroform, or THF) in the presence of a base (for example, imidazole, pyridine, 4-dimethylaminopyridine, lutidine, collidineimidazole with 2 equivalents or excess amount of imidazole being preferred) at 0 to 80° C. for 1 to 24 hr. The silylating agent is not particularly limited, and silylating agents usable herein include, for example, those wherein the silyl group is t-butyldimethylsilyl, isopropyldimethylsilyl, or ethyldimethylsilyl. Silylating agents wherein the silyl group is t-butyldimethylsilyl (TBDMS) include, besides TBDMSCl, $TBDMSOClO_3$, $TBDMSOSO_2CF_3$, and TBDMSCN. Preferably, TBDMSCl is used in an equivalent or excess amount. The resultant substance, of which the hydroxyl group at the 7-position has been protected with a silyl group, is then reacted with an equivalent or excess amount of an acylating agent in a solvent (for example, methylene chloride, chloroform, 1,2-dichloroethane, benzene, or toluene) in the presence of a base (for example, an organic base, such as 4-dimethylaminopyridine, pyridine, lutidine, collidine, triethylamine, or diisopropylethylamine) at 0 to 100° C. for 1 hr to 2 days, thereby acylating the hydroxyl group at the 6-position. Thereafter, the silyl protective group is removed to prepare a compound with the hydroxyl group at the 6-position being acylated. The removal of the protective group may be carried out by reacting the compound having the protective group with an equivalent or excess amount of a fluoride reagent, such as tetrabutylammonium fluoride (TBAF), hydrogen fluoride-pyridine complex or cesium fluoride, acetic acid, trifluoroacetic acid, hydrochloric acid or the like in a suitable solvent (THF, methylene chloride, acetonitrile or the like) at 20 to 100° C. for 30 min to 5 hr. The use of an equivalent or excess amount of TBAF or hydrogen fluoride-pyridine complex is preferred.

Further, an acyl group may be introduced into the two hydroxyl groups respectively at the 6- and 7-positions by the following method. Specifically, substance PF1092C may be reacted with 4 to 5 equivalents of an acylating agent or an acid anhydride in a solvent (for example, methylene chloride, chloroform, 1,2-dichloroethane, benzene, or toluene) in the presence of a base (for example, an organic base, such as 4-dimethylaminopyridine, pyridine, diisopropylethylamine, lutidine, or collidine with 5 to 6 equivalents of 4-dimethylaminopyridine or 5 equivalents or excess amount of pyridine being preferred) at 20 to 30° C. for 1 to 24 hr.

Furthermore, it is also possible to simultaneously synthesize, as a mixture, a compound with both the hydroxyl groups at the 6- and 7-positions being acylated, a compound with only the hydroxyl group at the 6-position being acylated, and a compound with only the hydroxyl group at the 7-position being acylated. Specifically, substance PF1092C is reacted with a large excess of an acylating agent or an acid anhydride in a solvent (for example, methylene chloride, chloroform, 1,2-dichloroethane, benzene, or toluene) in the presence of a suitably bulky organic base (with 2 to 10 equivalents of diisopropylethylamine being preferred) at 20 to 30° C. for 5 to 24 hr. Thereafter, the three compounds may be separated from one another by suitable separating means (for example, silica gel column chromatography).

For the compound, with only the hydroxyl group at the 6- or 7-position acylated, prepared by the above method, the remaining hydroxyl group may further be modified. Further, the compounds represented by the formula (I) may be prepared by alkoxyalkylation, alkylation, carbamoylation, sulfonylation, or modification with acetal, as described in this specification.

(b) Carbamoylation of Hydroxyl Groups at 6- and 7-positions

The hydroxyl groups respectively at the 6- and 7-positions of substance PF1092C may be carbamoylated as follows.

Specifically, substance PF1092C may be reacted with an equivalent or excess amount of an isocyanate in a solvent (for example, DMF, methylene chloride, chloroform, benzene, or toluene) in the presence of a base (for example, an organic base, such as 4-dimethylaminopyridine, pyridine, lutidine, collidine, triethylamine, or diisopropylethylamine with a catalytic amount of 4-dimethylaminopyridine being preferred) at 25 to 120° C. for 1 to 24 hr. Thus, three compounds, i.e., a compound with both the hydroxyl groups at the 6- and 7-positions being carbamoylated, a compound with only the hydroxyl group at the 6-position being carbamoylated, and a compound with only the hydroxyl group at the 7-position being carbamoylated, are obtained as a mixture. Thereafter, the three compounds may be separated from one another by suitable separating means (for example, silica gel chromatography).

Alternatively, after protection of the hydroxyl group at the 7-position with a silyl group by the above method, the hydroxyl group at the 6-position may be carbamoylated followed by removal of the protective group to prepare a compound with the hydroxyl group at the 6-position being selectively carbamoylated.

Furthermore, for the compound, with only the hydroxyl group at the 6- or 7-position acylated, prepared by the above method, the remaining hydroxyl group may be further modified. Furthermore, the compounds represented by the formula (I) may be prepared by alkoxyalkylation, alkylation, carbamoylation, sulfonylation, or modification with acetal, as described in this specification.

(c) Alkyloxylation or Alkoxyalkyloxylation of Hydroxyl Group at 6- and 7-positions The hydroxyl groups respectively at the 6- and 7-positions of substance PF1092C may be alkyloxylated or alkoxyalkyloxylated as follows.

Specifically, the alkyloxylation may be carried out by reacting substance PF1092C with $R^{*3}$-X, wherein $R^{*3}$ represents optionally substituted $C_1$–$C_{10}$ alkyl or optionally substituted $C_7$–$C_{15}$ aralkyl and X represents a halogen atom, in a solvent (for example, toluene, DMF, methylene chloride, chloroform, or benzene) in the presence of a base (for example, a metal hydride such as sodium hydride or potassium hydride) at a temperature of −40 to −40° C. for 5 min to 2 days.

On the other hand, the alkoxyalkyloxylation may be carried out by reacting substance PF1092C with $R^{*4}$-X, wherein $R^{*4}$ represents optionally substituted $C_2$–$C_2$ alkoxyalkyl and X represents a halogen atom, in a solvent (for example, methylene chloride, chloroform, benzene, or toluene) in the presence of a base (for example, an organic base such as pyridine, lutidine, collidine, triethylamine, or diisopropylethylamine) at a temperature of 20 to 100° C. for 10 to 24 hr.

As a result of the above reaction, a compound with the hydroxyl group at 6- or 7-position being alkyloxylated or alkoxyalkyloxylated can be obtained.

For the compound, with only the hydroxyl group at the 6- or 7-position alkyloxylated or alkoxyalkyloxylated, prepared by the above method, the remaining hydroxyl group may be further modified. Further, the compounds represented by the formula (I) may be prepared by alkoxyalkylation, alkylation, carbamoylation, sulfonylation, or modification with acetal, as described in this specification.

(d) Modification with Acetal

Modification of substance PF1092C with acetal may be carried out by reacting substance PF1092C with an equivalent or excess amount of a dihydro ether, such as dihydropyran, dihydrofuran, or ethyl vinyl ether, in a solvent (for example, toluene, benzene, methylene chloride, or chloroform) in the presence of an acid (for example, p-toluenesulfonic acid, or pyridinium p-toluenesulfonic acid preferably in an amount ranging from a catalytic amount to 3 equivalents) at 20 to 100° C. for 10 min to 3 hr.

(e) Introduction of Substituent having α Configuration into 7-position

Although the hydroxyl group at the 7-position of substance PF1092C is of P configuration, a substituent having a configuration can be stereoselectively introduced into the 7-position by the following method.

Specifically, substance PF1092C may be reacted with a sulfonyl halide in the presence of an equivalent or excess amount of a base and, immediately after that, reacted with a nucleophilic reagent, such as water, alcohol or potassium acetate, to give a 7α-o-substituted derivative wherein the 7-position has been subjected to Walden inversion.

More specifically, substance PF1092C is reacted with a sulfonyl halide in a solvent (for example, methylene chloride, chloroform, benzene, or toluene with methylene chloride being preferred) in the presence of a base (for example, an organic base, such as diisopropylethylamine, pyridine, lutidine, collidine, triethylamine, or 4-dimethylaminopyridine, preferably 1 to 3 equivalents of diisopropylethylamine) at −30 to 10° C. for 5 min to one hr, followed by nucleophilic substitution. Sulfonylating agents usable herein include, besides methanesulfonyl chloride, p-toluenesulfonyl chloride and benzylsulfonyl chloride. In many cases, however, use of 1 to 2 equivalents of methanesulfonyl chloride offers good results. Nucleophilic reagents usable herein include water, alcohols, such as methanol, ethanol, and propanol, and metal salts of aliphatic carboxylic acids, such as potassium acetate, sodium acetate, potassium propionate, and sodium propionate. When the nucleophilic reagent is water or an alcohol, the reagent is used in an amount of 3 to 10 equivalents. Solvents usable in this reaction include methylene chloride, chloroform, and acetonitrile with methylene chloride being preferred. The reaction may be carried out at −30 to 10° C. for 30 min to 5 hr. On the other hand, when the nucleophilic reagent is a metal salt of an aliphatic carboxylic acid, use of the reagent in an amount of 1 to 5 equivalents offers good results. Further, addition of a catalytic amount of a crown ether, such as 18-crown-6, accelerates the reaction. Solvents usable in this reaction include acetonitrile, chloroform, and methylene chloride with acetonitrile being preferred. The reaction may be carried out at 0 to 30° C. for 30 min to 6 hr.

For the compound, with only the hydroxyl group at the 7-position being substituted, prepared by the above method, the remaining hydroxyl group may be further modified. Further, the compounds represented by the formula (I) may be prepared by alkoxyalkylation, alkylation, carbamoylation, sulfonylation, or modification with acetal, as described in this specification.

(f) Introduction of Amino Group into 6- or 7 Position

An oxazoline ring may be constructed at the 6- or 7-position of substance PF1092C followed by a ring-opening reaction to introduce an amino group into the 6- or 7-position.

Substance PF1092C is reacted with a nitrile in the presence of an excess amount of 2-acetoxyisobutyryl bromide to give an oxazoline derivative with a nitrogen atom introduced at the 6- or 7-position in p configuration. The oxazoline derivative is then reacted with a nucleophilic reagent, such as water or an alcohol, in the presence of a suitable acid catalyst to give a novel compound with the 6- or 7-position being acylaminated. In the formation of the oxazoline ring, the amount of 2-acetoxyisobutyryl bromide used is preferably an equivalent or excess amount. A nitrile corresponding to an acylamino group to be introduced, for example, acetonitrile, propionitrile, or benzonitrile, is used as a solvent in the reaction. The reaction may be carried out at −40 to 50° C. for 10 min to 24 hr. In the subsequent ring-opening reaction, besides water, an alcohol, such as methanol or ethanol, may be used as the nucleophilic agent. Use of 0.1 to several equivalents of an organic acid, such as p-toluenesulfonic acid or trifluoromethanesulfonic acid, as the acid catalyst is preferred. When the nucleophilic reagent is water, use of an excess amount of an organic base, such as pyridine, is preferred from the viewpoint of preventing the system from becoming acidic. The reaction may be carried out at −20 to 120° C. for 1 to 5 hr.

(g) Total Synthesis of Compounds Represented by Formula (I) (part 1)

According to another embodiment of the present invention, total synthesis of substance PF1092C as described in the following scheme has been established, permitting total synthesis of the compounds represented by the formula (I). The synthesis will be described in the order of description of scheme.

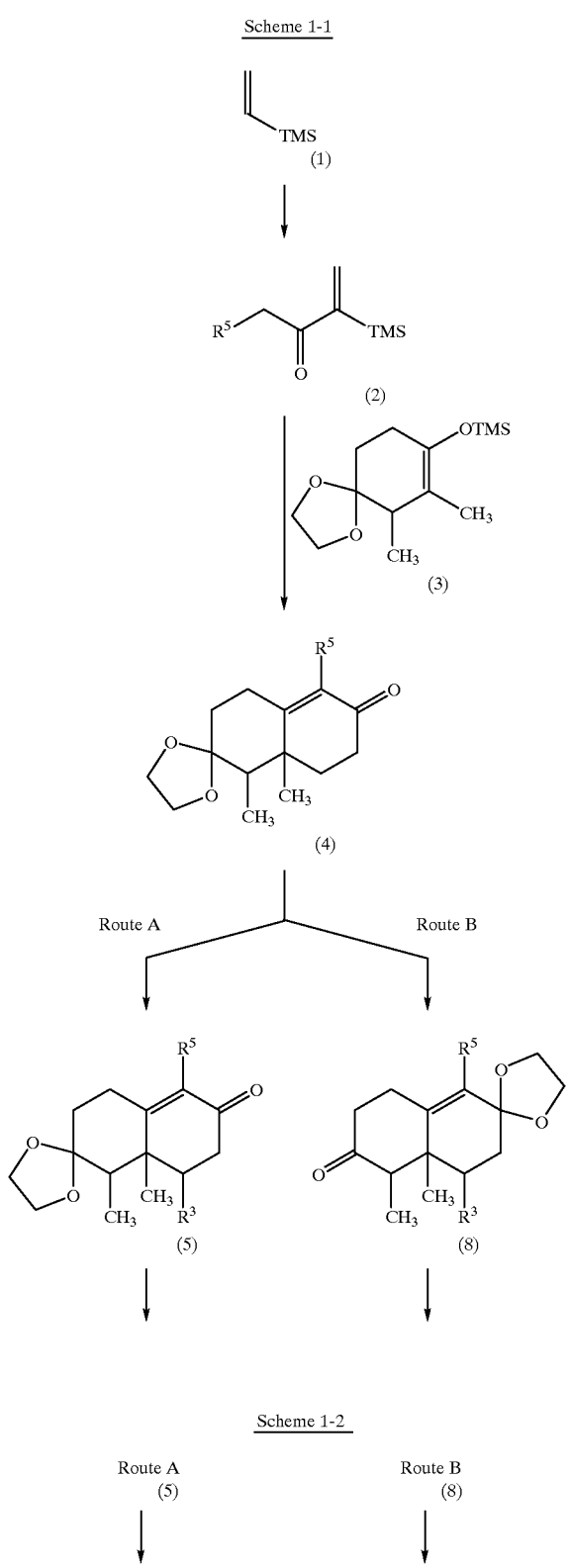

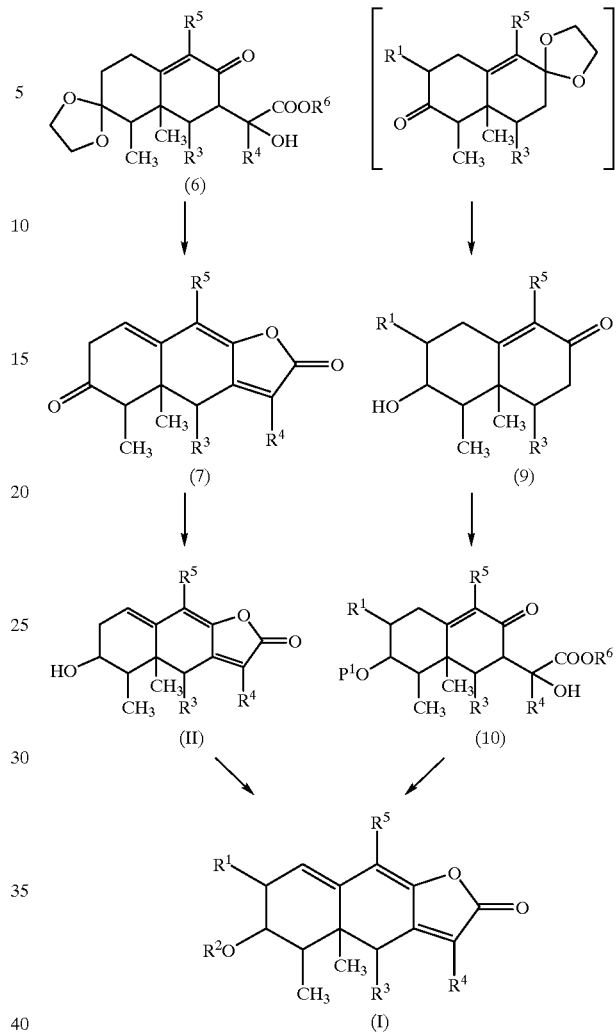

A compound (1) (vinyltrimethylsilane) is converted to a halide in the presence of a base, and the halide is then reacted with magnesium to give a Grignard reagent. The Grignard reagent is then reacted with an aldehyde to give an alcohol compound which is then oxidized to give a compound (2) wherein $R^5$ is as defined above in connection with the formula (I). Halogenating agents usable for the halogenation include bromine, chlorine, and iodine, and the amount of the halogenating agent used is preferably 1 to 2 equivalents. Bases usable herein include organic bases such as diethylamine, and the amount of the organic base used is preferably 1 to 5 equivalents. The halogenation may be carried out at −78 to 0° C. for 1 to 24 hr. Aldehydes usable in the subsequent Grignard reaction include acetaldehyde and propionaldehyde, and the amount of the aldehyde used is preferably 1 to 2 equivalent. The reaction may be carried out in a solvent, such as THF or ether, at 80 to 120° C. for 1 to 6 hr. The oxidation may be any commonly used oxidation, and a preferred example thereof is oxidation with Jones' reagent.

Then, a compound (4), wherein $R^5$ is as defined above in connection with the formula (I), is synthesized as follows. Specifically, the compound (2) and a compound (3) described in a literature (Liebigs Ann. Chem., 186–190, 1982) are subjected to Michael addition in the presence of an alkyllithium, such as methyllithium to give a coupling compound which is then cyclocondensed with a base to give the compound (4). In the compound (4), two methyl groups are sterically regulated to cis configuration. In the Michael addition, the amount of the alkyllithium used is preferably 1 to 3 equivalents, and solvents usable in this reaction include aprotic solvents, such as ether, THF, and dimethoxyethane, with dimethoxyethane being preferred. The reaction may be carried out at a temperature of −78 to 0° C. for 30 min to 6 hr. In the subsequent cyclocondensation, 1 to 3 equivalents of a metal alcoholate, such as sodium methoxide, is preferably used as the base. The reaction may be carried out at 0 to 100° C. for 30 min to 6 hr.

The compounds represented by the formula (I) are synthesized via synthesis route A or B depending upon $R^1$. Specifically, in the case of compounds wherein $R^1$ is a substituent introduced by a carbon-carbon bond, the compounds are synthesized via the synthesis route B, while the other compounds are synthesized via the synthesis route A.

Synthesis Route A

A compound (5), wherein $R^3$ and $R^5$ are as defined above in connection with the formula (I), may be synthesized as follows. Specifically, the compound (4) is regioselectively dehydrogenated to give a $\Delta^{1,4}$-diene form which is then subjected to a Michael addition reaction with an organocopper reagent to give a compound (5) with an alkyl group introduced thereinto. For the above dehydrogenation, 1 to 3 equivalents of DDQ is preferably used. The reaction may be carried out in a solvent, such as toluene, benzene, xylene, or dioxane, at a temperature of 30 to 150° C. for 5 to 24 hr. For the Michael addition reaction, the amount of the organocopper reagent used is preferably 3 to 10 equivalents. The reaction may be carried out in an aprotic solvent, such as ether or THF, at a temperature of −50 to ° C. for 15 to 20 min. For compounds wherein $R^3$ represents a hydrogen atom, this step is omitted, and steps after the compound (4) are carried out.

A compound (6), wherein $R^3$, $R^4$, and $R^5$ are as defined above in connection with the formula (I) and $R^6$ represents a hydrogen atom or $C_1$–$C_6$ lower alkyl, may be synthesized as follows. The compound (5) is condensed with a keto ester in the presence of a base and optionally a catalytic amount of zinc chloride by aldol condensation to give the compound (6). When $R^4$ in the compound (6) represents alkyl, organic bases commonly used in conventional aldol reactions may be used as the base. For example, use of 1 to 3 equivalents of lithium diisopropylamide is preferred. Further, addition of a catalytic amount of dried zinc chloride is preferred. The reaction may be carried out in a solvent, such as THF or ether, at a temperature of −78 to 0° C. for 30 min to 6 hr. On the other hand, when $R^4$ represents a hydrogen atom, preferred bases include water-soluble inorganic bases, such as sodium hydroxide and potassium hydroxide, with use of a large excess amount of water-soluble sodium hydroxide being more preferred. The reaction may be carried out in an alcohol solvent (preferably ethanol) at a temperature of 20 to 100° C. for 30 min to 6 hr.

A compound (7), wherein $R^3$, $R^4{}_1$ and $R^5$ are as defined above in connection with the formula (I), may be prepared by heating the compound (6) in the presence of an acid catalyst. The acid catalyst is preferably an organic acid, such as 0.1 to several equivalents of p-toluenesulfonic acid. The reaction may be carried out in a solvent, such as benzene or xylene, preferably toluene, at a temperature of 0 to 100° C. for 30 min to 6 hr.

Compounds represented by the formula (II) may be prepared by a reduction of the compound (7) with sodium borohydride. The hydroxyl group at the 6-position of the resultant compounds is generally of β configuration. Reducing agents usable herein include lithium borohydride and tetrabutylammonium borohydride. Among them, sodium borohydride is preferred. The amount of the reducing agent used is 1 to 5 equivalents. The reaction may be carried out in an alcohol solvent (preferably methanol) at a temperature of −10 to 50° C. for several min to 3 hr.

Conversion of the compound represented by the formula (II) to the compound represented by the formula (I) may be carried out as follows.

At the outset, introduction of a hydroxyl group into the 7-position of the compound represented by the formula (II) may be carried out by oxidation with an oxidizing agent (for example, selenium dioxide, DDQ, or manganese dioxide with a large excess amount of selenium dioxide being preferred) in a solvent (for example, dioxane, acetic acid, ethanol, t-butanol, or water with dioxane being preferred). In general, the hydroxyl group at the 7-position of the resultant compound is generally of β configuration. The reaction may be carried out at a temperature of 20 to 60° C. for one hr to several days.

The hydroxyl group at the 6- and 7-positions of the compound thus obtained may be reacted in the same manner as described above in connection with the reaction using substance PF1092C as a starting compound to give the compound represented by the formula (I).

Synthesis Route B

A compound (8), wherein $R^3$ and $R^5$ are as defined above in connection with the formula (I), may be prepared by deketalizing the compound (4) and then introducing a regioselective protective group into the enone. The deketalization may be carried out using an aqueous sodium perchlorate solution or an inorganic acid, such as hydrochloric acid or sulfuric acid, with use of 0.1 to 1.0 equivalent of an aqueous sodium perchlorate solution being preferred. The reaction may be carried out in a solvent (for example, methylene chloride, chloroform, benzene, or toluene) at a temperature of −25 to 25° C. for 1 to 5 hr. The protection of the enone may be generally carried out with a reagent used for the conventional acetalization, and use of 1 to 5 equivalents of 1,2-bis(trimethylsilyloxy)ethane is preferred. In the reaction, addition of a catalytic amount of trimethylsilyltrifluoromethane sulfonate is preferred. The reaction may be carried out in a solvent (for example, methylene chloride, chloroform or toluene with methylene chloride being preferred) at a temperature of −78 to 0° C. for 3 to 7 days.

A compound (9), wherein $R^1$, $R^3$, and $R^5$ are as defined above in connection with the formula (I), may be prepared by reacting the compound (8) with an alkyl halide in the presence of a base to alkylate the α position of the ketone and subsequently conducting a reduction and deprotection. Bases usable in the alkylation include those used in the conventional alkylation. The base is preferably lithium diisopropylamide, and the amount thereof is preferably 1 to 2 equivalents. The alkylation may be carried out in a solvent, such as THF or ether, at a temperature of −78 to 25° C. for 2 to 6 hr. The reduction may be carried out with a reducing agent, such as lithium borohydride, sodium borohydride, or tetrabutylammonium borohydride, and use of 1 to 5 equivalents of lithium borohydride is preferred. The reaction may be carried out in an alcohol solvent (preferably methanol) at a temperature of −10 to 50° C. for 6 to 14 hr. Acid catalysts usable in the subsequent deprotection include organic acids such as p-toluenesulfonic acid, and the amount thereof is preferably 0.1 to 1 equivalent. The reaction may be carried out in a solvent (for example, acetone, benzene, xylene, or toluene with acetone being preferred) at a temperature of 0 to 50° C. for 30 min to 2 hr.

A compound (10), wherein $R^3$, $R^4$, and $R^5$ are as described above in connection with the formula (I), $R^6$ represents a hydrogen atom or lower alkyl and $P^1$ represents a protective group for the hydroxyl group, may be prepared as follows. At the outset, the hydroxyl group of the compound (9) is protected. Protective groups usable herein include conventional protective groups used for the hydroxyl group, and β-methoxyethoxymethyl (MEM) is preferred with the amount thereof being preferably 5 to 10 equivalents. The reaction may be carried out in a solvent (for example, DMF or dioxane with DMF being preferred) at a temperature of 0 to 50° C. for 20 to 40 hr. Subsequently, the protected compound is condensed with α-keto ester by aldol condensation in the presence of a base and optionally a catalytic amount of zinc chloride to give the compound (10). Bases usable herein include organic bases used in conventional aldol reaction, and lithium diisopropylamide is preferred with the amount thereof being preferably 1 to 3 equivalents. The zinc chloride is preferably a catalytic amount of dried zinc chloride from the viewpoint of yield. The reaction may be carried out in a solvent, such as THF or ether, at a temperature of −78 to 0° C. for 30 min to 6 hr.

The resultant compound (10) may be heated in the presence of an acid catalyst to give the compound represented by the formula (I). Acid catalysts usable herein include organic acids such as p-toluenesulfonic acid with the amount thereof being preferably 0.1 to several equivalents. The reaction may be carried out in a solvent (for example, benzene, toluene, or xylene with benzene being preferred) at a temperature of 0 to 100° C. for 30 min to 6 hr. Thereafter, the protective group for the hydroxyl group at the 6-position is removed, and the hydroxyl group may be reacted in the same manner as described above in connection with the reaction using substance PF1092C as a starting compound to give the compound represented by the formula (I).

(h) Total Synthesis of Compounds Represented by Formula (I) (part 2)

According to still another embodiment of the present invention, total synthesis of substance PF1092C as described in the following scheme has been established, permitting total synthesis of the compounds represented by the formula (I). The synthesis will be described in the order of description of the scheme.

Scheme 2

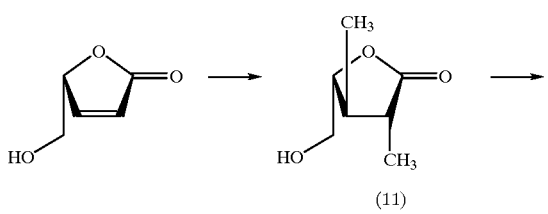

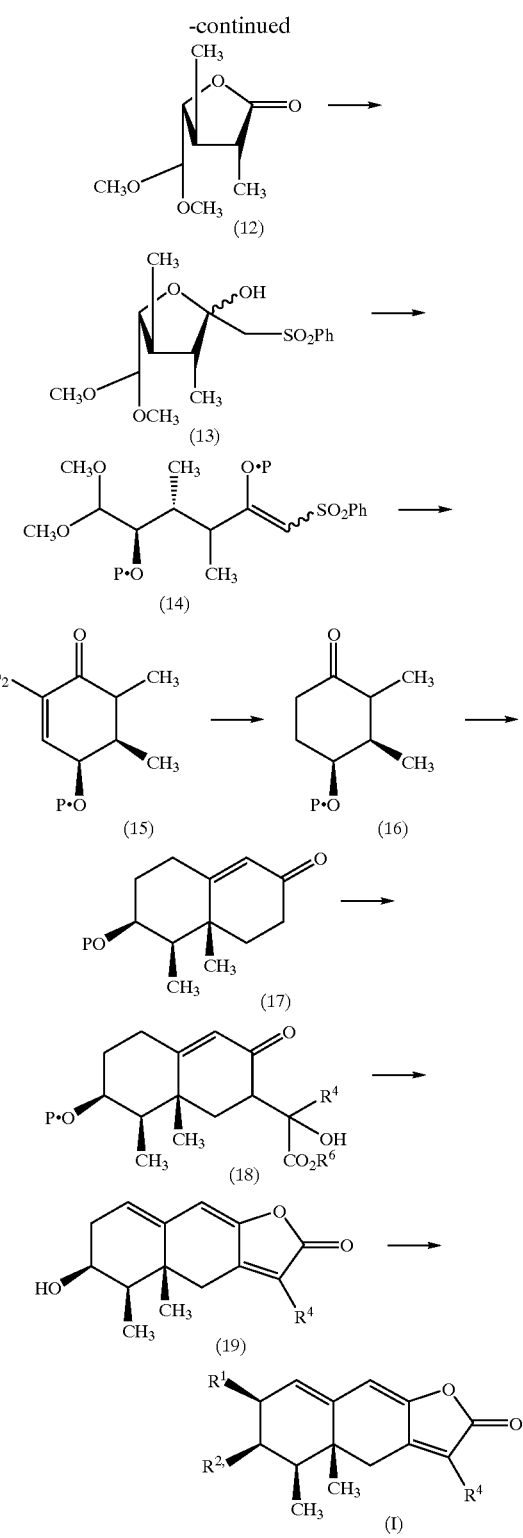

In the process represented by the above scheme, (R)-(+)-5-hydroxymethyl-2 (5)-furanone is used as a starting compound.

At the outset, the hydroxyl group at the 6-position of the starting compound is protective with a protective group (for example, trityl group), and the compound is then reacted with a copper reagent, such as methylcopper lithium, to introduce methyl into the 4-position. Thereafter, methyl iodide is added thereto in the presence of lithiumbistrimethylsilylamide to introduce a methyl group at the a position (3-position) of the carbonyl. The protective group is then removed by known means to give a compound (11). Subsequently, the hydroxyl group in the compound (11) is oxidized, for example, with dimethylsulfoxide to give an aldehyde which is then subjected to acetal protection using, for example, methyl orthoformate to give a compound (12).

The compound (12) is then reacted with benzenesulfonylmethyl in the presence of a base to give a benzenesulfonyl compound (13). Preferably, one to two equivalents of an organic base, such as n-butyllithium, is used as the base. The reaction may be carried out in a solvent (for example, THF or diethyl ether) at a temperature of −78 to 0° C. for 30 min to 6 hr.

A compound (14), wherein P represents a protective group for a hydroxyl group, may be prepared by protecting the hydroxyl group of the compound (13) with a protective group, such as t-butyldimethylsily and then conducting a ring-opening reaction in the presence of a base. Silylating agents usable herein include t-butyldimethylsilyl chloride and t-butyldimethylsilyltrifluoromethane sulfonate, and use of 1.5 to 5 equivalents of t-butyldimethylsilyltrifluoromethane sulfonate is preferred. Preferred bases include organic bases such as triethylamine and 2,6-lutidine and imidazole with 3 to 10 equivalents of 2,6-lutidine being preferred. The reaction may be carried out in a solvent (for example, THF, diethyl ether or methylene chloride with THF being preferred) at a temperature of 0 to 50° C. for 10 to 20 hr.

The compound (14) is then subjected to a ring-closing reaction with a Lewis acid to give a cyclohexenone (15) with two asymmetric centers. The Lewis acid is preferably tin tetrachloride with the amount thereof being preferably 1 to 2 equivalents. The reaction may be carried out in a solvent (for example, acetonitrile, benzene, toluene, or methylene chloride with methylene chloride being preferred) at a temperature of −78 to 0° C. for 1 to 5 hr.

The double bond of the compound (15) is reduced to give a compound (16). Preferred reducing agents include aluminum-mercury amalgam with the amount thereof being preferably 10 to 20 equivalents. The reaction may be carried out in a solvent (for example, diethyl ether or THF with diethyl ether being preferred) at a temperature of 0 to 25° C. for 1 to 5 hr.

The resultant compound (16) and 3-trimethylsilyl-3-buten-2-one may be subjected to Michael addition and cyclocondensation in the presence of a base to give a bicyclic compound (17) with two methyl groups being sterically regulated to cis configuration. An alkyllithium, such as methyllithium, is used as a reagent in the Michael addition, and use thereof in an amount of 1 to 3 equivalents is preferred. The reaction may be carried out in an aprotic solvent, such as diethyl ether, THF, or dimethoxyethane, preferably dimethoxyethane, at a temperature of −78 to 0° C. for 30 min to 6 hr. The subsequent cyclocondensation may be carried out in the presence of a base (for example, a metal alcoholate, such as sodium methoxide, with the amount thereof being preferably 1 to 3 equivalents) at a temperature of 0 to 100° C. for 30 min to 6 hr.

Subsequently, the compound (17) is condensed with α-keto ester by aldol condensation in the presence of a base and optionally a catalytic amount of zinc chloride to give a compound (18) wherein $R^4$ is as defined above in connection with the formula (I). Bases usable herein include those used in conventional aldol reaction, and use of 1 to 3 equivalents of lithiumditrimethylsilylamide is preferred. The zinc chloride is preferably a catalytic amount of dried zinc chloride from the viewpoint of yield. The reaction may be carried out in a solvent, such as THF or ether, at a temperature of −78 to 0° C. for 30 min to 6 hr.

The compound (18) may be heated under reflux in the presence of an acid catalyst to give a compound (19). Acid catalysts usable in the ring-closing reaction include organic acids, such as camphorsulfonic acid, with the amount thereof being preferably 0.1 to several equivalents. The reaction may be carried out in a solvent (for example, 1,4-dioxane, benzene, or toluene with 1,4-dioxane being preferred) at a temperature of 0 to 150° C. for 15 to 48 hr.

The introduction of a hydroxyl group into the 7-position of the compound (19) may be carried out by oxidation with an oxidizing agent (for example, selenium dioxide, DDQ, or manganese dioxide with a large excess amount of selenium dioxide being preferred) in a solvent (for example, 1,4-dioxane, acetic acid, ethanol, t-butanol, or water with 1,4-dioxane being preferred). In general, the hydroxyl group at the 7-position of the resultant compound is generally of β configuration. The reaction may be carried out at a temperature of 30 to 100° C. for one hr to several days.

The hydroxyl group at the 6- and 7-positions of the compound thus obtained may be reacted in the same manner as described above in connection with the reaction using substance PF1092C as a starting compound to give the compound represented by the formula (I).

(i) Resolution of Racemic Compounds

The compounds represented by the formula (I) according to the present invention may exist as the above various isomers, and racemic derivatives may be resoluted by optical resolution using a chiral column. Chiral columns usable herein include a polymer stationary phase column, a protein stationary phase column, and a cellulosic stationary phase column. A preferred mobile phase usable herein is phosphate buffer-acetonitrile for the protein stationary phase column and hexane-isopropanol for the cellulosic stationary phase column.

Substance PF1092

The starting material of the above process for the production of the compound of the formula (I) may be prepared by culturing strain PF 1092 described below.
1. Mycological Properties of Strain PF1092

(1)Cultural characteristics:

It forms a colony of 30 to 40 mm in diameter on Czapek yeast extract agar medium after culturing at 25° C. for 7 days. The colony is white and funiculose, and forms conidia scatteringly. Backside of the colony becomes light brown. It grows well on malt extract agar medium, and diameter of its colony reaches 40 to 45 mm after culturing at 25° C. for 7 days. The colony is white and funiculose, forms oonidia slightly and produces light brown extract. Backside of the colony becomes light mud yellow. At 37° C., its growth and formation of conidia are superfor to those at 25° C. on all media.

(2) Morphological characteristics:

Conidiophore stands straight almost vertically from aerial mycelium, is rough-surfaced and has a size of 30–70× 2.5–8.5 µm. Penicilli are monoverticillate. Four to eight phialides are formed on conidiophore, each being needle-like and having smooth to slightly rough surface and a size of 8–10×2.5–3.0 µm. Conidium is globose to subglobose, flat with slightly depressed sides, and has smooth surface and a size of 2.0–2.5 µm.

On the basis of the above mycological characteristics, this strain was identified as the genus Penicillium.

This strain has been deposited in National Institute of Bioscience and Human Technology Agency of Industrial Science and Technology, as international deposition number under Budapest Treaty; FERM BP-5350.

As can be found in other fungi, strain PF1092 is apt to change its properties. For example, not only strain PF1092 but also all of its mutant strains (spontaneous or induced mutants), zygotes and genetic recombinants can be used, provided that they can produce substances PF1092.

2. A Method of Culturing Substance PF1092 Producing Strain

The substance PF1092 producing strain is cultured using a medium containing nutrients which can be utilized by ordinary microorganisms. As the nutrient sources, known materials conventionally used for the culturing of fungi can be used. Examples of usable carboon sources include glucose, sucrose, starch syrup, dextrin, starch, glycerol, molasses, animal and plant oils and the like. Examples of usable nitrogen sources include soybean meal, wheat germ, corn steep liquor, cotton seed meal, meat extract, peptone, yeast extract, ammonium sulfate, sodium nitrate, urea and the like. In addition to these nutrients, it is effective to add inorganic salts which can release sodium, potassium, calcium, magnesium, cobalt, chlorine, phosphate, sulfate and the like ions as oocasion demands. Also, certain organic and inorganic substances which can assist the fungal growth and enhance the production of substances PF1092 may be added properly.

Preferably, the culturing may be carried out under aerobic conditions, particularly by static culturing using a rice medium or by submerged culturing. Suitable culturing temperature is 15 to 40° C., but the culturing is carried out at about 26 to 37° C. in most cases. Though it varies depending on the medium and culturing conditions employed, accumulation of produced substances PF1092 reaches its maximum generally atter 10 to 20 days of culturing in the case of static culturing using a rice medium or generally after 2 to 10 days of shaking or fermentor culturing. The culturing is completed when maximum accumulation of substances PF1092 is obtained, and the desired substance is isolated and purified from the culture broth.

3. Purrication of Substances PF1092

Substances PF1092 thus obtained by the present invention can be extracted and purified from the cultured mixture making use of its properties by usual separation means such as solvent extraction, ion exchange resin method, absorption or partition chromatography; gel filtration, dialysis, precipitation and the like, alone or in an appropriate combination. For example, substances PF1092 can be extracted with acetone-water or ethyl acetate after culturing using a rice medium. In order to further purity substances PF1092, a chromatography may be carried out using an adsorbent such as silica gel (for example, Wakogel C-200 manutactured by Wato Pure Chemical Industries), alumina or the like or Sephadex LH-20 (manutactured by Pharmacia), Toyo Pearl HW-40SF (manufactured by Tosoh) or the like.

By carrying out such techniques alone or in an optional combination, highly purried substance PF1092A, substance PF1092B and substance PF1092C are obtained. Physicochemical properties and chemical structures of the thus obtained substances PF1092A, PF1092B and PF1092C are as follows.

1. Physico-chemical Properties and Chemical Structure of Substance PF1092A:

(1) Color and shape: colorless needle crystals.

(2) Molecular formula: $C_{17}H_{20}O_5$.

(3) Mass spectrum (FD-MS): m/z 304 (M)$^+$.

(4) Specific rotation: $[\alpha]_D$=−10.86° (c 0.5, CHCl$_3$).

(5) Ultraviolet ray absorption spectrum λmax: 322 (17,500) nm(ε) (in methanol).

(6) Infrared absorption spectrum: measured in KBr tablet (see FIG. 1).

Figure 2:
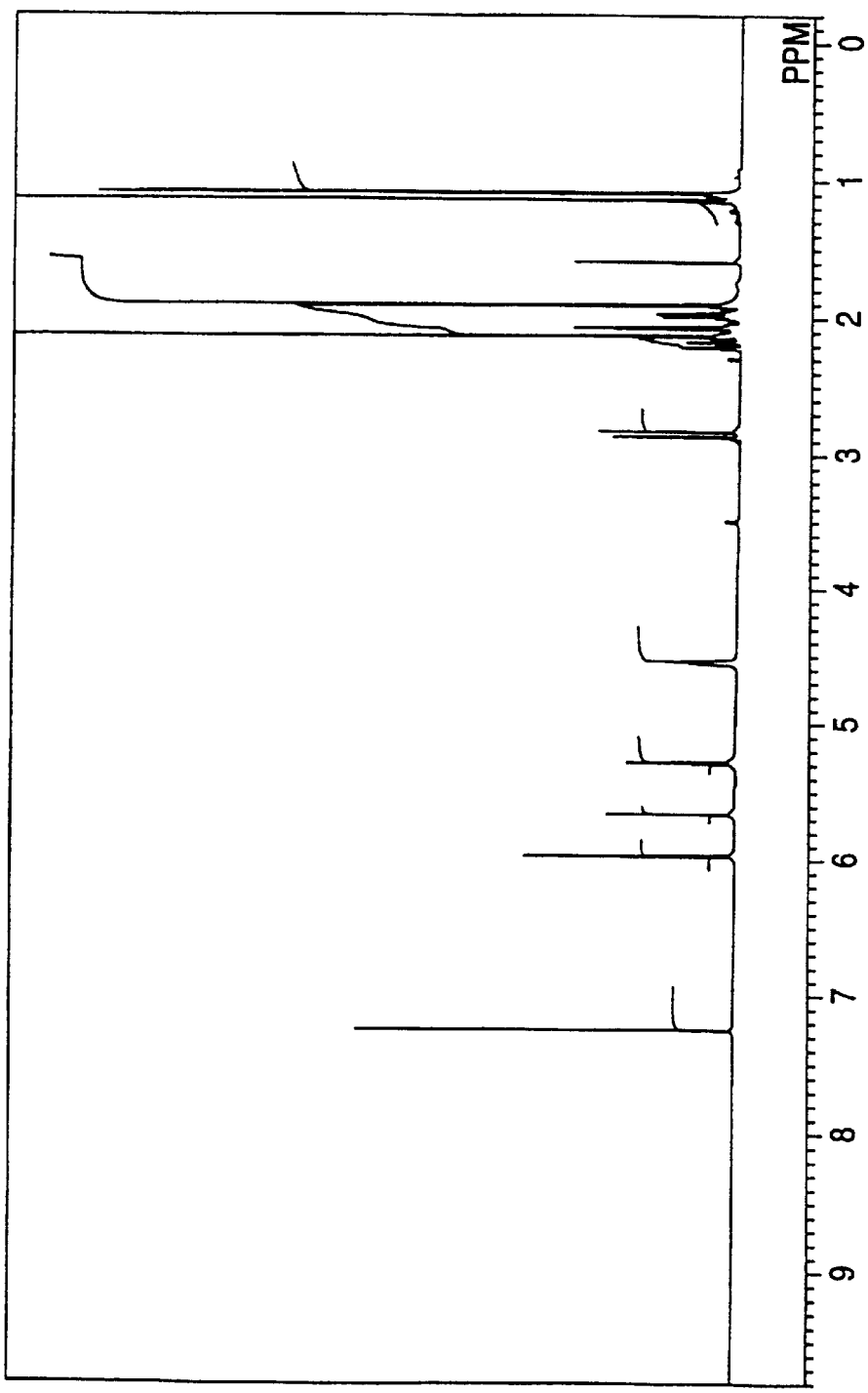
FIG. 2 is a graph showing 400 MHz $^1$H NMR spectrum of substance PF1092A in $CDCl_3$ solution.
Figure 3:
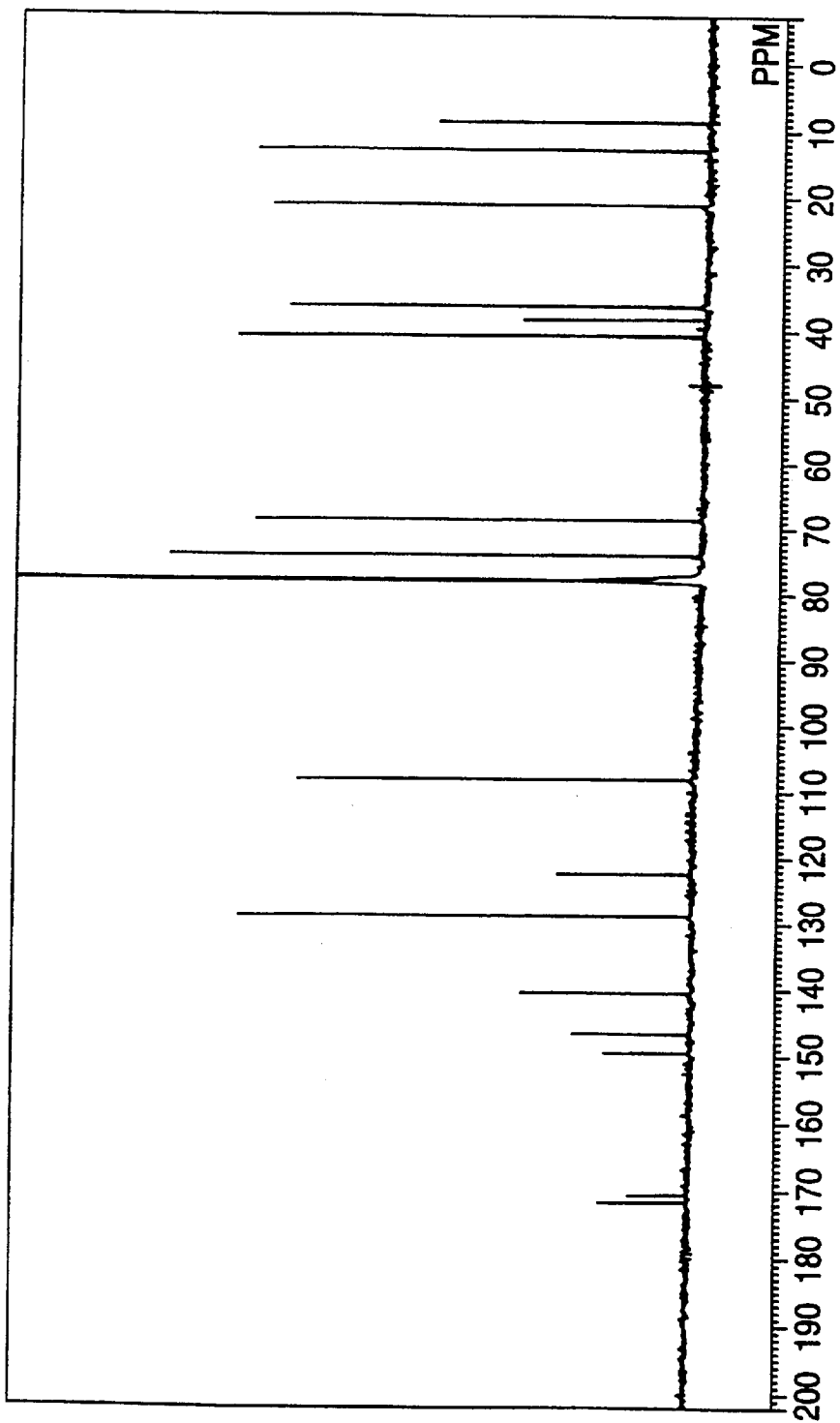
FIG. 3 is a graph showing 100 MHz $^{13}$C NMR spectrum of substance PF1092A in $CDCl_3$ solution.

(7) $^1$HNMR Spectrum: measured in CDCl$_3$ solution (see FIG. 2) (PPm): 5.97 (1H), 5.66 (1H), 5.28 (1H), 4.53 (1), 2.83 (1H), 2.19 (3H), 2.18 (1H), 2.05 (OH), 1.97 (1H), 1.91 (3H), 1.15 (3H), 1.10 (8H).

Figure 8:
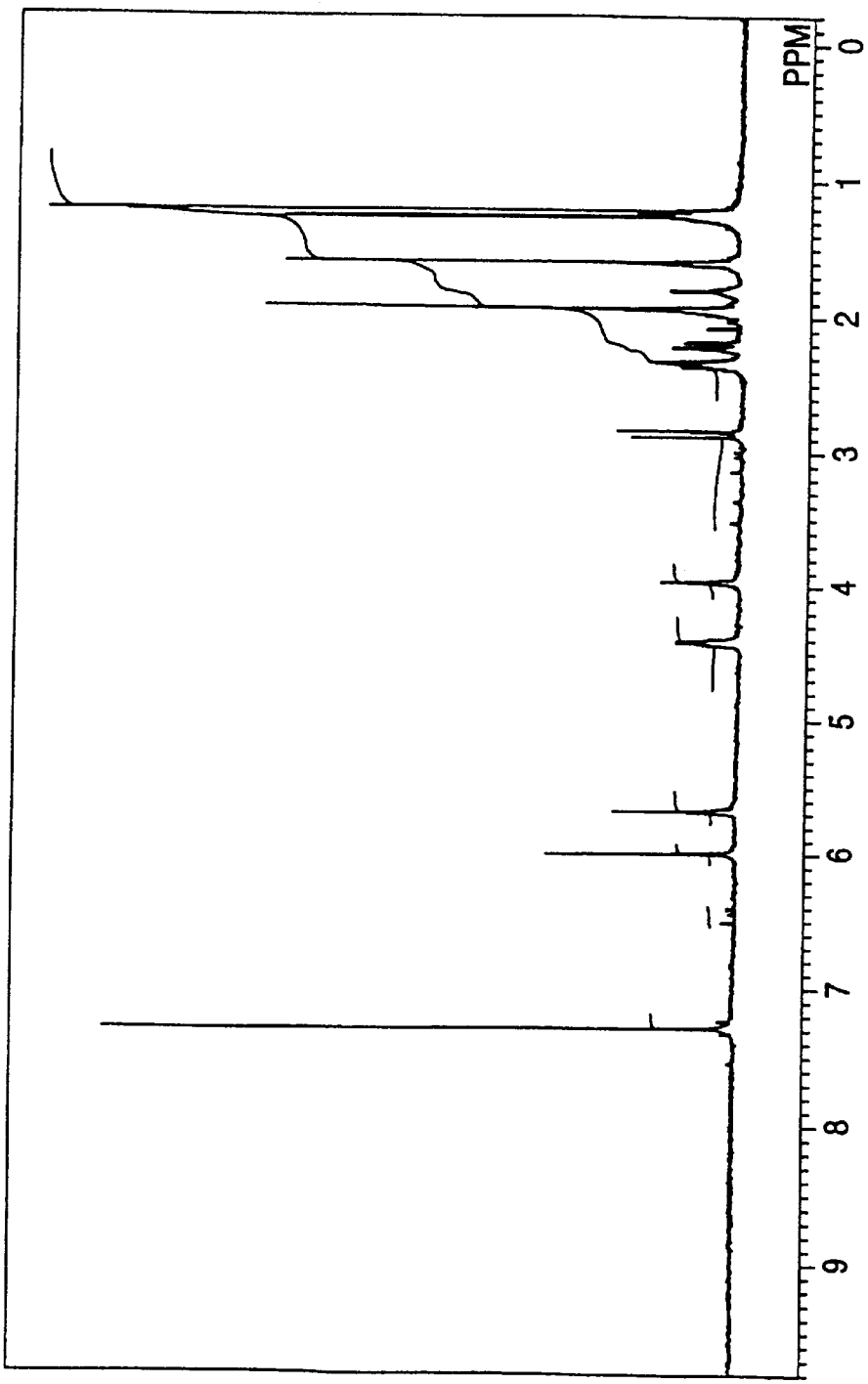
FIG. 8 is a graph showing 400 MHz $^1$H NMR spectrum of substance PF1092C in $CDCl_3$ solution.
Figure 9:
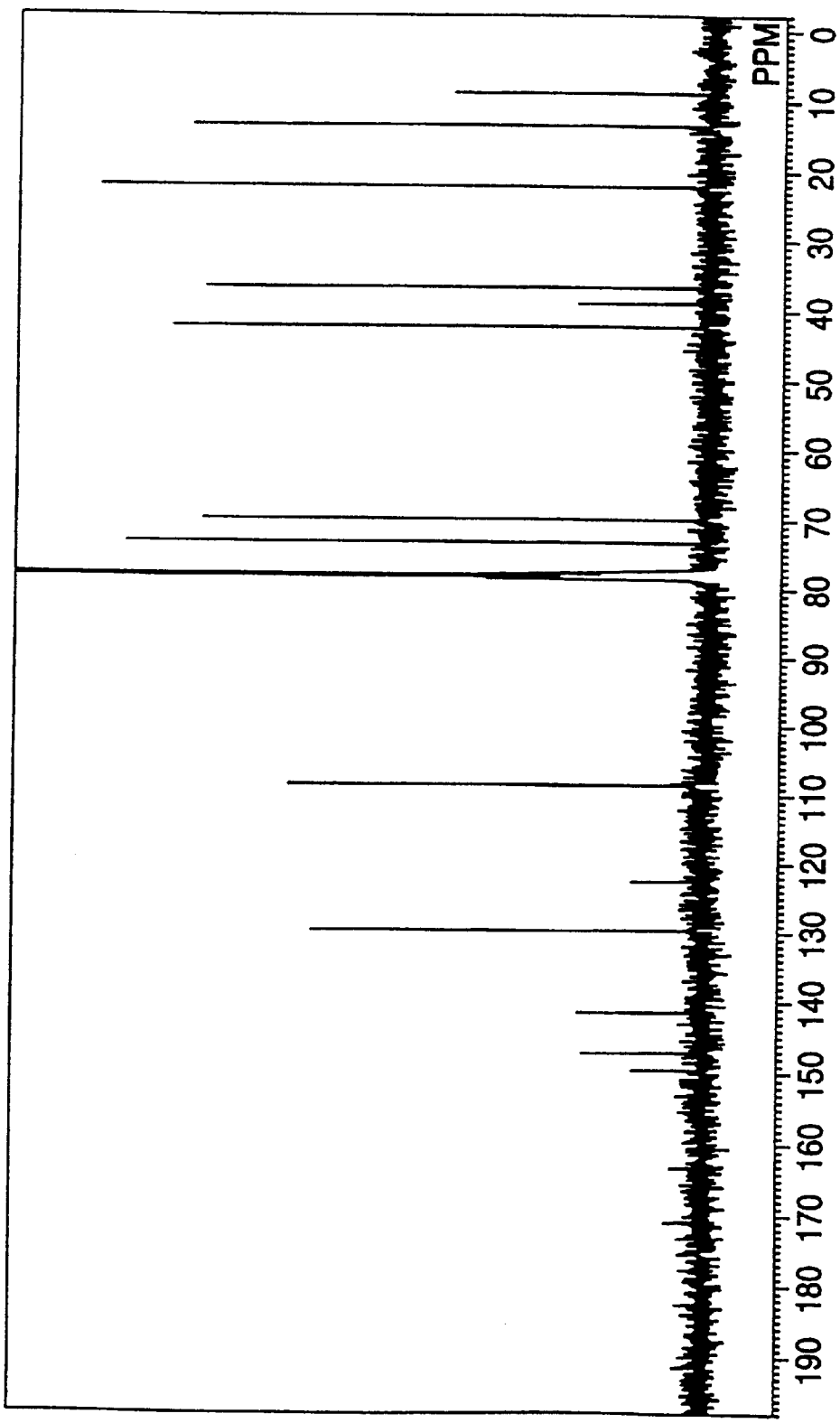
FIG. 9 is a graph showing 100 MHz $^{13}$C NMR spectrum of substance PF1092C in CDCl3 solution.

(8) $^{13}$C NMR Spectrum: measured in CDCl$_3$ solution (see FIG. 8) (PPm): 171.8 (s), 170.9 (s), 149.3 (s), 146.3 (s), 140.4 (s), 128.7 (d), 122.3 (s), 107.7 (d), 73.6 (d), 68.2 (d), 40.2 (d), 37.8 (s), 35.6 (t), 21.0 (q), 20.9 (q), 12.7 (q), 8.6 (q).

(9) Solubility: soluble in chloroform, acetone, ethyl acetate, methanol and dimethyl sulioxide, and insoluble in water and hexane.

(10) Basic, acidic or neutral: neutral substance.

(11) Rf Value by silica gel thin layer chromatography (TLC): 0.25 in hexane-ethyl acetate (1:1)developing solvent.

Based on the above physico-chemical properties and X-ray crystallographic analysis, the chemical structure of the substance PF1092A was determined as the compound of the forumula (I) wherein R$^1$ is OH, R$^2$ is CH$_3$COO—, R$^3$ and R$^5$ are H, and R$^4$ is CH$_3$.

2. Physico-chemical Properties and Chemical Structure of Substance PF1092B:

(1) Color and shape: colorless needle crystals.

(2) Molecular formula: $C_{17}H_{20}O_5$.

(3) Mass spectrum (FD-MS): m/z 304 (M)$^+$.

(4) Specifc rotation: $[\alpha]_D^{24}$=−110.22° (c 0.5, CHCl$_3$).

(5) Ultraviolet ray absorption spectrum λmax: 320 (15,100) nm(ε) (in methanol).

Figure 4:
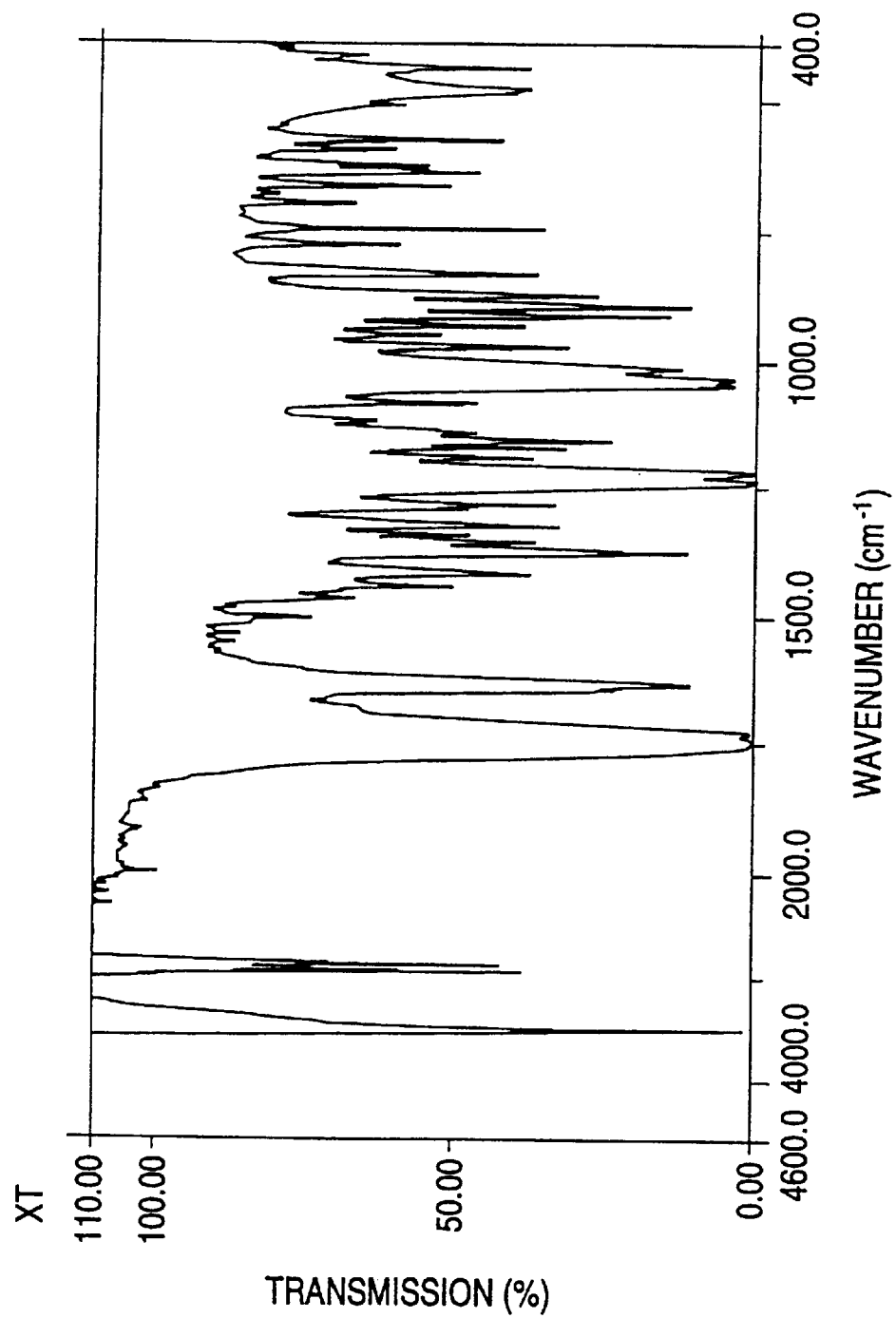
FIG. 4 is a graph showing infrared absorption spectrum of substance PF1092B in KBr tablet.

(6) Infrared absorption spectrum: measured in KBr tablet (see FIG. 4).

Figure 5:
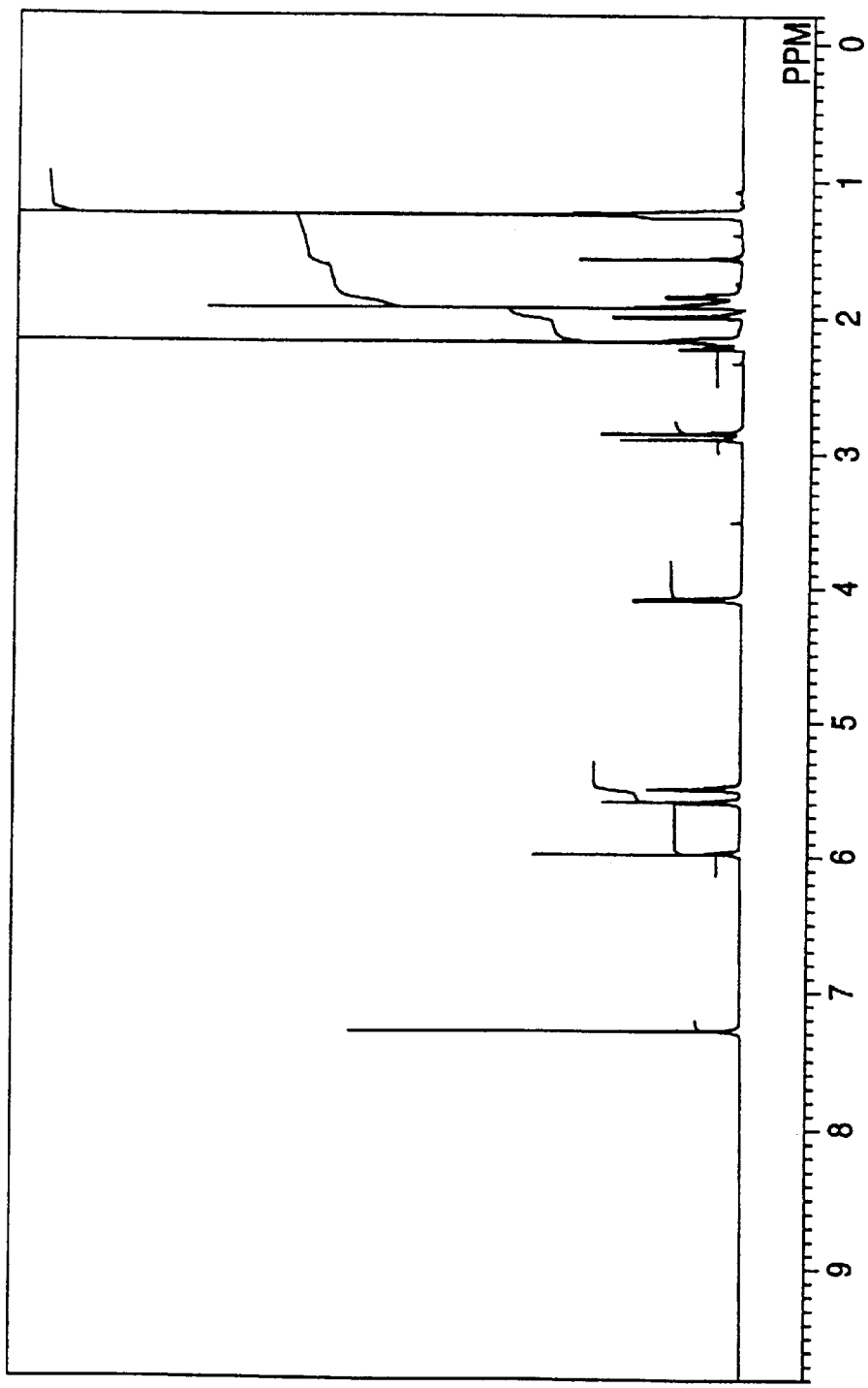
FIG. 5 is a graph showing 400 MHz $^1$H NMR spectrum of substance PF1092B in $CDCl_3$ solution.

(7) $^1$H NMR Spectrum: measured in CDCl$_3$ solution (see FIG. 5) (PPm): 5.95 (1H), 5.57 (1H), 5.46 (1), 4.05 (1H), 2.84 (1H), 2.18 (1H), 2.15 (3H), 1.97 (OH), 1.91 (3H), 1.83 (1H), 1.23 (3H), 1.22 (3H)

Figure 6:
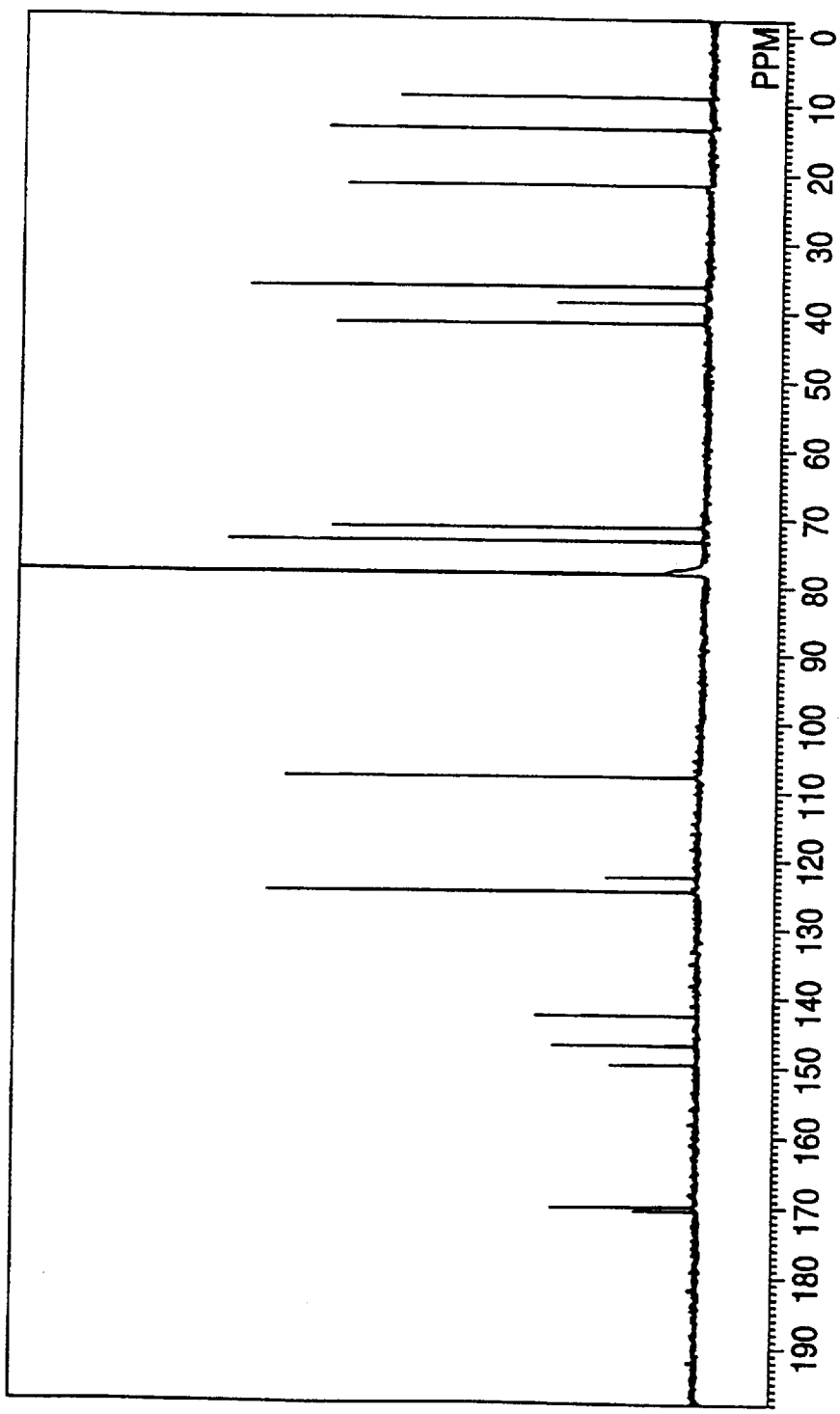
FIG. 6 is a graph showing 100 MHz $^{13}$C NMR spectrum of substance PF1092B in $CDCl_3$ solution.

(8) $^{13}$C NMR Spectrum: measured in CDCl$_3$ solution (see FIG. 6) (PPm): 170.9 (s), 170.2 (s), 149.5 (s), 146.7 (s), 142.4 (s), 124.5 (d), 122.4 (s), 107.4 (d), 72.5 (d), 70.5 (d), 41.0 (d), 38.1 (s), 35.8 (t), 21.4 (q), 21.2 (q), 12.8 (q), 8.6 (q).

(9) Solubility: soluble in chloroform, acetone, ethyl acetate, methanol and dimethyl sulioxide, and insoluble in water and hexane.

(10) Basic, acidic or neutral: neutral substance.

(11) Rf Value by silica gel thin layer chromatography (TLC): 0.42 in hexane-ethyl acetate (1:1) developing solvent.

Based on the above physico-chemical properties and X-ray crystallographic analysis, the chemical structure of the substance PF1092A was determined as the compound of the forumula (I) wherein R$^1$ is CH$_3$COO—, R$^2$ is OH, R$^3$ and R$^5$ are H, and R$^4$ is CH$_3$.

3. Physico-chemical Properties and Chemical Structure of Substance PF1092C:

(1) Color and shape: colorless needle crystals.

(2) Molecular formula: $C_{15}H_{18}O_4$.

(3) Mass spectrum (FD-MS): m/z 262 (M)$^+$.

(4) Specific rotation: $[\alpha]_D^{24}$=−96.36° (c 0.5, CHCl$_3$).

(5) Ultraviolet ray absorption spectrum λmax: 324 (14,900) nm(ε) (in methanol).

Figure 7:
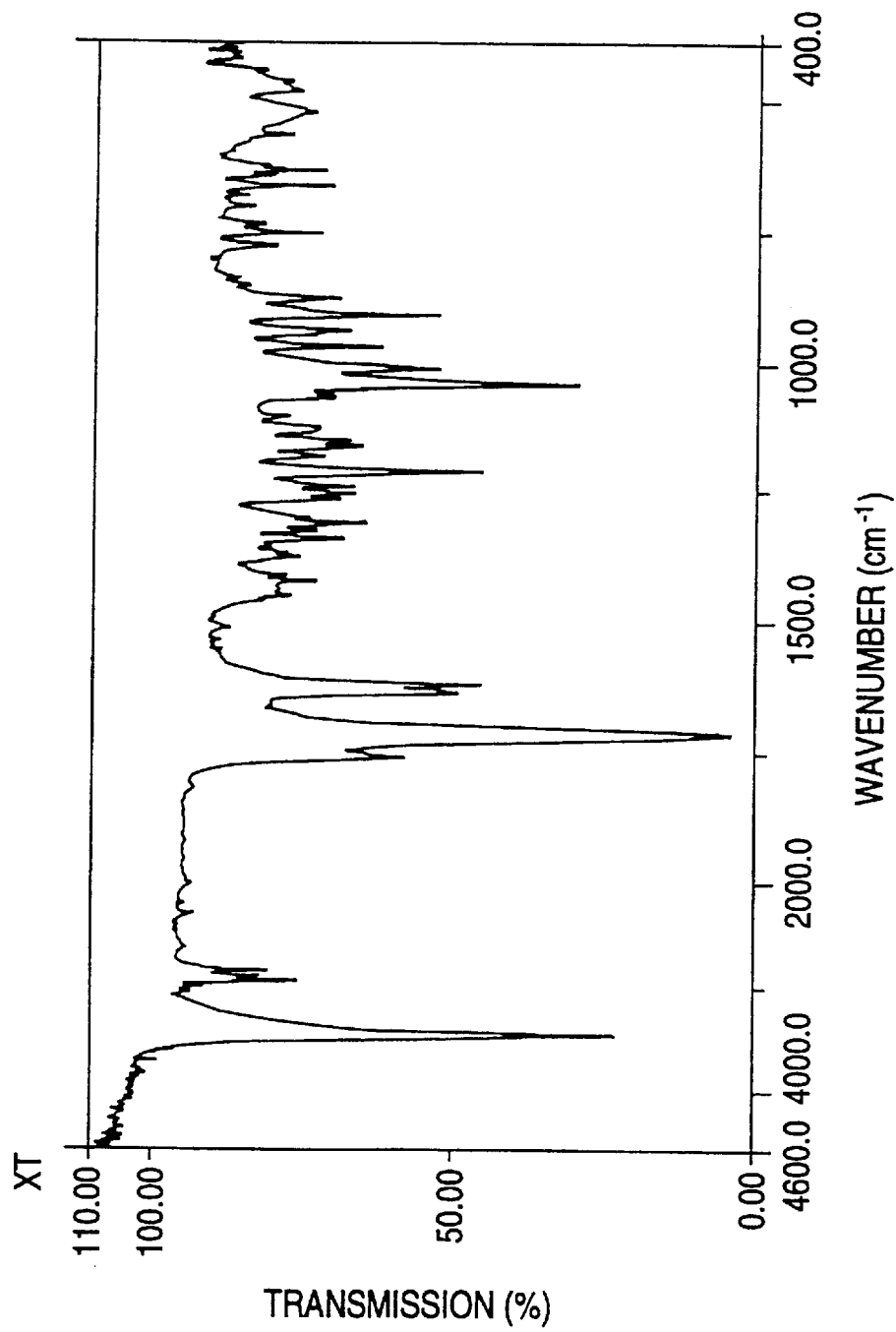
FIG. 7 is a graph showing infrared absorption spectrum of substance PF1092C in KBr tablet.

(6) Infrared absorption spectrum: measured in KBr tablet (see FIG. 7).

(7) $^1$H NMR Spectrum: measured in CDCl3 solution (see FIG. 8) (ppm): 5.96 (1H), 5.64 (1H), 4.37 (1H), 3.93 (1H), 2.83 (1H), 2.22 (OH), 2.20 (OH), 2.17 (1H), 1.91 (3H), 1.24 (3H), 1.20 (3H).

(8) $^{13}$C NMR Spectrum: measured in CDCl$_3$ (ppm): 171.0 (s), 149.3 (s), 146.7 (s), 141.0 (s), 129.1 (d), 122.1 (s), 107.8 (d), 72.4 (d), 69.0 (d), 40.3 (d), 37.9 (s), 35.8 (t), 21.5 (q), 13.0 (q), 8.5 (q).

(9) Solubility: soluble in chloroform, acetone, ethyl acetate, methanol and dimethyl sultoxide, and insoluble in water and hexane.

(10) Basic, acidic or neutral: neutral substance

(11) Rf Value by silica gel thin layer chromatography (TLC): 0.20 in hexane-ethyl acetate (1:1) dveloping solvent.

Based on the above physico-chemical properties and X-ray crystallographic analysis, the chemical structure of the substance PF1092A was determined as the compound of the forumula (I) wherein $R^1$ and $R^2$ are OH, $R^3$ and $R^5$ are H, and $R^4$ is $CH_3$.

EXAMPLES

The present invention will be described in more detail with reference to the following examples, though it is not limited to these examples only.

Example A1

(4aR,5R,6R,7S)-6-Hydroxy-7-propionyloxy-4a,5,6, 7-tetrahydro-3,4a,5-trimethylnaphtho[2,3-b]furan-2 (4H)-one Substance PF1092C (15 mg, 0.06 mmol) was dissolved in methylene chloride (0.3 ml). Diisopropylethylamine (25 μl, 0.14 mmol) and propionyl chloride (11 μl, 0.13 mmol) were added to the solution under ice cooling, and the mixture was stirred under ice cooling for 30 min. The temperature was raised to 25° C., and the mixture was then stirred for additional 17 hr. Water was added to the reaction solution, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by preparative TLC (hexane:ethyl acetate=1:1) to prepare the title compound (8.2 mg, 45%).

$^1$H NMR (CDCl$_3$) δ 1.19 (t, J=7.5 Hz, 3H), 1.24 (s, 3H), 1.25 (d, J=7.0 Hz, 3H), 1.86 (dq, J=7.0, 1.7 Hz, 1H), 1.92 (d, J=1.7 Hz, 3H), 2.20 (br d, J=16.3 Hz, 1H), 2.44 (q, J=7.5 Hz, 2H), 2.86 (d, J=16.3 Hz, 1H), 4.06 (m, 1H), 5.49 (m, 1H), 5.58 (br s, 1H), 5.97 (s, 1H); MS (EI) m/z 318 (M)$^+$.

Example A2

(4aR,5R,6R,7S)-7-Hydroxy-6-propionyloxy-4a,5,6, 7-tetrahydro-3,4a,5-trimethylnaphtho[2,3-b]furan-2 (4H)-one Substance PF1092C (9.9 mg, 0.04 mmol) was dissolved in methylene chloride (0.2 ml). To the solution were added 4-dimethylaminopyridiene (4.5 mg, 0.04 mmol) and propionyl chloride (8 μl, 0.09 mmol) under ice cooling, and the mixture was stirred under ice cooling for 30 min. The temperature was raised to 25° C., and the mixture was then stirred for additional 22 hr. Water was added to the reaction mixture, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by preparative TLC (hexane:ethyl acetate=1:1) to give the title compound (4.9 mg, 41%).

$^1$H NMR (CDCl$_3$) δ 1.12 (d, J=7.1 Hz, 3H), 1.18 (d, J=0.6 Hz, 3H), 1.18 (t, J=7.6 Hz, 3H), 1.93 (d, J=1.8 Hz, 3H), 2.01 (dq, J=7.1, 1.6 Hz, 1H), 2.21 (br d, J=16.4 Hz, 1H), 2.43, 2.43 (each q, J=7.6 Hz, 2H), 2.85 (d, J=16.4 Hz, 1H), 4.56 (m, 1H), 5.31 (ddd, J=5.1, 1.6, 1.6 Hz, 1H), 5.68 (br s, 1H), 6.00 (s, 1H); MS (EI) m/z 318 (M)$^+$.

Example A3

(4aR,5R,6R,7S)-6-(2-Furancarbonyl)oxy-7-hydroxy-4a,5,6,7-tetrahydro-3,4a,5-trimethylnaphtho[2,3-b] furan-2(4H)-one (1) Substance PF1092C (19 mg, 0.07 mmol) was dissolved in anhydrous DMF (0.4 ml). Imidazole (50 mg, 0.73 mmol) and t-butyldimethylsilyl chloride (65 mg, 0.43 mmol) were added to the solution, and the mixture was stirred at 25° C. for 7 hr. Water was added to the reaction mixture, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by preparative TLC (toluene:ethyl acetate=10:1) to prepare a corresponding 7-0-(t-butyldimethylsilyl) derivative (23 mg, 85%). (2) The compound (21 mg, 0.06 mmol) prepared in the above step (1) was dissolved in methylene chloride (0.45 ml). To the solution were added 4-dimethylaminopyridiene (34 mg, 0.27 mmol) and 2-furoyl chloride (24 μl, 0.24 mmol) under ice cooling, and the mixture was stirred under ice cooling for 30 min. The temperature was raised to 25° C., and the mixture was then stirred for additional 22 hr. Water was added to the reaction mixture, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by preparative TLC (toluene:ethyl acetate=20:1) to prepare a corresponding 7-0-(t-butyldimethylsilyl)-6-0-(2-furoyl) derivative (23 mg, 89%).

(3) The compound (18 mg, 0.04 mmol) prepared in the above step (2) was dissolved in anhydrous THF (0.5 ml). To the solution was added a 1.0 M tetrabutylammonium fluoride-THF solution (47 μl, 0.47 mmol) under ice cooling, and the mixture was stirred under ice cooling for 30 min. Water was added to the reaction mixture, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by preparative TLC (hexane:ethyl acetate=1:1) to prepare the title compound (5.9 mg, 42%).

$^1$H NMR (CDCl$_3$) δ 1.18 (d, J=7.1 Hz, 3H), 1.28 (s, 3H), 1.94 (d, J=1.6 Hz, 3H), 2.10 (dq, J=7.1, 1.7 Hz, 1H), 2.25 (br d, J=16.1 Hz, 1H), 2.89 (d, J=16.1 Hz, 1H), 4.63 (m, 1H), 5.52 (ddd, J=5.0, 1.7, 1.7 Hz, 1H), 5.73 (br s, 1H), 6.03 (s, 1H), 6.53 (dd, J=3.6, 1.6 Hz, 1H), 7.20 (br d, J=3.6 Hz, 1H), 7.60 (m, 1H); MS (EI) m/z 356 (M)$^+$.

Example A4

(4aR,5R,6R,7S)-6,7-Dipropionyloxy-4a,5,6,7-tetrahydro-3,4a,5-trimethylnaphtho[2,3-b]furan-2(4H)-one Substance PF1092C (16 mg, 0.06 mmol) was dissolved in methylene chloride (0.35 ml). To the solution were added 4-dimethylaminopyridiene (38 mg, 0.31 mmol) and propionyl chloride (24 μl, 0.28 mmol) under ice cooling, and the mixture was stirred under ice cooling for 30 min. The temperature was raised to 25° C., and the mixture was then stirred for additional 18 hr. Water was added to the reaction mixture, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by preparative TLC (toluene:ethyl acetate=5:1) to give the title compound (20 mg, 85%).

$^1$H NMR (CDCl$_3$) δ 1.10 (d, J=7.1 Hz, 3H), 1.14 (t, J=7.6 Hz, 3H), 1.17 (t, J=7.6 Hz, 3H), 1.21 (d, J=0.9 Hz, 3H), 1.94 (d, J=1.7 Hz, 3H), 2.06 (dq, J=7.1, 1.8 Hz, 1H), 2.24 (br d, J=16.2 Hz, 1H), 2.30, 2.31 (each q, J=7.6 Hz, 2H), 2.39 (q, J=7.6 Hz, 2H), 2.87 (d, J=16.2 Hz, 1H), 5.41 (m, 1H), 5.58 (br s, 1H), 5.64 (m, 1H), 5.99 (s, 1H); MS (SIMS) m/z 375 (M+H)$^+$.

Example A5

Substance PF1092C (30 mg, 0.11 mmol) was dissolved in methylene chloride (0.6 ml). To the solution were added diisopropylethylamine (100 μl, 0.57 mmol) and propionic anhydride (294 μl, 2.29 mmol) under ice cooling, and the mixture was stirred under ice cooling for 30 min. The temperature was raised to 25° C., and the mixture was then stirred for additional 15 hr. Water was added to the reaction mixture, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by preparative TLC (hexane:ethyl acetate=1:1) to give the compound of Example A1 (19 mg, 52%), the compound of Example A2 (6.0 mg, 16%), and the compound of Example A4 (3.9 mg, 9%).

Example A6a (4aR,5R,6R,7S)-6-Hydroxy-7-(n-propyl)carbamoyloxy-4a,5,6,7-tetrahydro-3,4a,5-trimethylnaphtho[2,3-b ]furan-2(4H)-one Substance PF1092C (18 mg, 0.07 mmol) was dissolved in anhydrous DMF (0.4 ml). n-Propyl isocyanate (325 μl, 3.47 mmol) was added to the solution, and the mixture was stirred at 100° C. for 4 hr. Water was added to the reaction mixture, followed by extraction with ethyl acetate. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by preparative TLC (hexane:ethyl acetate=1:2) to prepare the title compound (9.1 mg, 38%).

$^1$H NMR (CDCl$_3$) δ 0.95 (t, J=7.3 Hz, 3H), 1.24 (s, 3H), 1.25 (d, J=7.3 Hz, 3H), 1.56 (seq, J=7.3 Hz, 2H), 1.86 (dq, J=7.3, 1.8 Hz, 1H), 1.93 (d, J=1.8 Hz, 3H), 2.21 (br d, J=16.0 Hz, 1H), 2.86 (d, J=16.0 Hz, 1H), 3.19 (m, 2H), 4.09 (m, 1H), 4.86 (m, 1H), 5.40 (m, 1H), 5.62 (s, 1H), 5.97 (s, 1H); MS (EI) m/z 347 (M)$^+$.

Example A6b (4aR,5R,6R,7S)-7-Hydroxy-6-(n-propyl)carbamoyloxy-4a,5,6,7-tetrahydro-3,4a,5-trimethylnaphtho[2,3-b]furan-2(4H)-one In Example A6a, the title compound (2.0 mg, 8%), together with the compound described in Example A6a, was obtained. $^1$H NMR (CDCl$_3$) δ 0.93 (t, J=7.4 Hz, 3H), 1.21 (d, J=7.2 Hz, 3H), 1.22 (s, 3H), 1.55 (m, 2H), 1.93 (d, J=1.5 Hz, 3H), 1.97 (br q, J=7.2 Hz, 1H), 2.19 (br d, J=16.9 Hz, 1H), 2.85 (d, J=16.9 Hz, 1H), 3.18 (m, 2H), 4.54 (m, 1H), 4.79 (m, 1H), 5.12 (m, 1H), 5.66 (br s, 1H), 5.98 (s, 1H); MS (EI) m/z 347 (M)$^+$.

Example A6c (4aR,5R,6R,7S)-6,7-di[(n-propyl)carbamoyloxy]-4a,5,6,7-tetrahydro-3,4a, 5-trimethylnaphtho[2,3-b]furan-2(4H)-one In Example A6a, the title compound (4.3 mg, 14%), together with the compound described in Example A6a and the compound described in Example A6b, was obtained. $^1$H NMR (CDCl$_3$) δ 0.93 (t, J=7.3 Hz, 3H), 0.93 (t, J=7.7 Hz, 3H), 1.14 (d, J=6.4 Hz, 3H), 1.17 (s, 3H), 1.53 (m, 4H), 1.93 (d, J=1.3 Hz, 3H), 2.02 (br q, J=6.4 Hz, 1H), 2.23 (br d, J=16.2 Hz, 1H), 2.86 (d, J=16.2 Hz, 1H), 3.15 (m, 4H), 5.31 (m, 1H), 5.51 (m, 1H), 5.66 (br s, 1H), 5.98 (s, 1H), 6.20 (m, 2H); MS (SIMS) m/z 455 (M+Na)$^+$.

Example A7

(4aR,5R,6R,7S)-7-Benzyloxy-6-hydroxy-4a,5,6,7-tetrahydro-3,4a,5-trimethylnaphtho[2,3-b]furan-2(4H)-one Substance PF1092C (9.7 mg, 0.04 mmol) was dissolved in toluene (0.2 ml). To the solution were added 60% sodium hydride (31 mg, 0.78 mmol) and benzyl bromide (132 μl, 1.11 mmol) under ice cooling, and the mixture was stirred under ice cooling for 30 min. The temperature was raised to 25° C., and the mixture was then stirred for additional 2 days. Water was added to the reaction solution, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by column chromatography on silica gel (chloroform:methanol=50:1) to give the title compound (5.3 mg, 41%).

$^1$H NMR (CDCl$_3$) δ 1.24 (s, 3H), 1.70 (br q, J=7.2 Hz, 1H), 1.77 (d, J=7.2 Hz, 3H), 1.92 (d, J=1.8 Hz, 3H), 2.15 (br d, J=16.3 Hz, 1H), 2.85 (d, J=16.3 Hz, 1H), 4.06 (m, 1H), 4.15 (m, 1H), 4.67 (d, J=11.8 Hz, 1H), 4.73 (d, J=11.8 Hz, 1H), 5.70 (s, 1H), 5.97 (s, 1H), 7.30–7.40 (m, 5H); MS (FD) m/z 352 (M)$^+$.

Example A8

(4aR,5R,6R,7S)-6-Benzoyloxy-7-methoxymethoxy-4a,5,6,7-tetrahydro-3,4a,5-trimethylnaphtho[2,3-b]furan-2(4H)-one (1) Substance PF1092C (50 mg, 0.19 mmol) was dissolved in methylene chloride (1.0 ml). To the solution were added diisopropylethylamine (40 μl, 0.23 mmol) and methoxymethyl chloride (17 μl, 0.22 mmol) under ice cooling, and the mixture was stirred under ice cooling for 30 min. The temperature was raised to 25° C., and the mixture was stirred for additional 15 hr. Water was added to the reaction mixture, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by preparative TLC (chloroform:methanol=50:1) to prepare a corresponding 7-0-methoxymethyl derivative (24 mg, 42%).

(2) The compound (20 mg, 0.07 mmol) prepared in the above step (1) was dissolved in methylene chloride (0.4 ml). To the solution were added 4-dimethylaminopyridiene (12 mg, 0.12 mmol) and benzoyl chloride (9 μl, 0.09 mmol) under ice cooling, and the mixture was stirred under ice cooling for 30 min. The temperature was then raised to 25° C., and the mixture was stirred for additional 22 hr. Water was added to the reaction solution, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by preparative TLC (toluene:ethyl acetate=5:1) to give the title compound (13 mg, 49%).

$^1$H NMR (CDCl$_3$) δ 1.18 (d, J=7.1 Hz, 3H), 1.28 (br s, 3H), 1.94 (d, J=1.7 Hz, 3H), 2.10 (dq, J=7.1, 1.8 Hz, 1H), 2.26 (br d, J=16.3 Hz, 1H), 2.90 (d, J=16.3 Hz, 1H), 3.36 (s, 3H), 4.54 (d, J=7.0 Hz, 1H), 4.57 (m, 1H), 4.81 (d, J=7.0 Hz, 1H), 5.71 (ddd, J=4.8, 1.8, 1.8 Hz, 1H), 5.76 (br s, 1H), 6.07 (s, 1H), 7.45 (m, 2H), 7.57 (m, 1H), 8.02 (m, 2H); MS (EI) m/z 410 (M)$^+$.

Example A9

(4aR,5R,6R,7S)-7-Hydroxy-6-(2-tetrahydropyranyloxy)-4a, 5,6,7-tetrahydro-3,4a,5-trimethylnaphtho[2,3-b]furan-2(4H)-one Substance PF1092C (8.9 mg, 0.03 mmol) was dissolved in methylene chloride (0.2 ml). p-Toluenesulfonic acid monohydrate (21 mg, 0.11 mmol) and 3,4-dihydro-2H-pyran (15 μl, 0.16 mmol) were added to the solution, and the mixture was stirred at 25° C. for 30 min. Water was added to the reaction mixture, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by preparative TLC (chloroform:methanol=40:1) to give the title compound (isomer mixture, 4.2 mg, 36%).

$^1$H NMR (CDCl$_3$) δ 1.18 (d, J=0.5 Hz, 3H), 1.29 (d, J=7.1 Hz, 3H), 1.46–1.73 (m, 6H), 1.91 (dq, J=7.1, 3.1 Hz, 1H), 1.94 (d, J=2.1 Hz, 3H), 2.22 (br d, J=16.4 Hz, 1H), 2.84 (d, J=16.4 Hz, 1H), 3.67 (t, J=6.2 Hz, 2H), 4.15 (dd, J=6.9, 3.1 Hz, 1H), 4.59 (dd, J=6.9, 3.8 Hz, 1H), 4.92 (t, J=4.7 Hz, 1H), 5.75 (d, J=3.8 Hz, 1H), 5.96 (s, 1H); MS (EI) m/z 346 (M)$^+$.

$^1$H NMR (CDCl$_3$) δ 1.16 (d, J=0.8 Hz, 3H), 1.29 (d, J=7.2 Hz, 3H), 1.46–1.73 (m, 6H), 1.84 (dq, J=7.2, 2.3 Hz, 1H), 1.94 (d, J=2.1 Hz, 3H), 2.21 (br d, J=16.2 Hz, 1H), 2.87 (d, J=16.2 Hz, 1H), 3.65 (t, J=6.4 Hz, 2H), 4.18 (dd, J=6.0, 2.3 Hz, 1H), 4.80 (dd, J=6.0, 3.3 Hz, 1H), 4.97 (t, J=4.7 Hz, 1H), 5.67 (d, J=3.3 Hz, 1H), 5.96 (s, 1H); MS (EI) m/z 346 (M)$^+$.

Example A10

(4aR,5R,6R,7R)-7-Methoxy-6-propionyloxy-4a,5,6,7-tetrahydro-3,4a,5-trimethylnaphtho[2,3-b]furan-2(4H)-one (1) Substance PF1092C (200 mg, 0.76 mmol) was dissolved in methylene chloride (4.0 ml). Diisopropylethylamine (237 μl, 1.36 mmol) and methanesulfonyl chloride (88 μl, 1.14 mmol) were added to the solution at −15° C., and the mixture was stirred at the same temperature for 30 min. Methanol (153 μl, 3.78 mmol) was then added thereto, the temperature was raised to 25° C., and the mixture was then stirred for additional 45 min. Water was added to the reaction solution, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by column chromatography on silica gel (hexane:ethyl acetate=1:1) to prepare a corresponding 7α-methoxy derivative (110 mg, 52%).

(2) The compound (11 mg, 0.04 mmol) prepared in the above step (1) was dissolved in methylene chloride (0.25 ml). To the solution was added 4-dimethylaminopyridiene (25 mg, 0.21 mmol) and propionyl chloride (16 μl, 0.16 mmol) under ice cooling, and the mixture was stirred under ice cooling for 30 min. The temperature was raised to 25° C., and the mixture was then stirred for additional 3 hr. Water was added to the reaction mixture, followed by extraction with chloroform. The organic layer was washed with a 5% aqueous potassium hydrogensulfate solution and a saturated aqueous sodium hydrogencarbonate solution and dried over anhydrous sodium sulfate, and the solvent was removed by distillation under reduced pressure. The residue was purified by preparative TLC (toluene:ethyl acetate=4:1) to prepare the title compound (5.7 mg, 42%).

$^1$H NMR (CDCl$_3$) δ 1.12 (d, J=7.1 Hz, 3H), 1.14 (s, 3H), 1.16 (t, J=7.5 Hz, 3H), 1.93 (d, J=1.7 Hz, 3H), 2.10 (dq, J=7.1, 2.8 Hz, 1H), 2.25 (br d, J=16.4 Hz, 1H), 2.36 (q, J=7.5 Hz, 2H), 2.86 (d, J=16.4 Hz, 1H), 3.52 (s, 3H), 3.61 (dd, J=4.7, 1.4 Hz, 1H), 5.11 (ddd, J=2.8, 1.4, 1.4 Hz, 1H), 5.84 (br d, J=4.7 Hz, 1H), 6.00 (s, 1H); MS (FAB) m/z 333 (M+H)$^+$.

Example A11a (4aR,5R,6R,7S)-6-Acetylamino-7-hydroxy-4a,5,6,7-tetrahydro-3,4a,5-trimethylnaphtho[2,3-b]furan-2(4H)-one Substance PF1092C (102 mg, 0.39 mmol) was dissolved in anhydrous acetonitrile (4.0 ml). To the solution was added 2-acetoxyisobutylyl bromide (0.51 ml, 3.49 mmol), and the mixture was stirred at 25° C. for 30 min. Water was added to the reaction solution, followed by extraction with ethyl acetate. The organic layer was washed with saturated saline and a saturated aqueous sodium bicarbonate solution and dried over anhydrous sodium sulfate, and the solvent was removed by distillation under reduced pressure. The residue was purified by preparative TLC (hexane:ethyl acetate=1:4) to give a corresponding 2'-methyloxazoline derivative (54 mg, 49%).

The compound (54 mg, 0.19 mmol) prepared just above was dissolved in pyridine (1.9 ml), water (0.48 ml) and p-toluenesulfonic acid monohydrate (31 mg, 0.17 mmol) were added to the solution, and the mixture was stirred at 100° C. for 1.5 hr. Water was added to the reaction solution, followed by extraction with chloroform. The organic layer was washed with a 5% aqueous potassium hydrogensulfate solution and a saturated aqueous sodium bicarbonate solution and dried over anhydrous sodium sulfate, and the solvent was removed by distillation under reduced pressure. The residue was purified by preparative TLC (methylene chloride:methanol=10:1) to give the title compound (6.4 mg, 11%).

$^1$H NMR (CDCl$_3$) δ 1.12 (s, 3H), 1.16 (d, J=7.1 Hz, 3H), 1.93 (d, J=1.7 Hz, 3H), 2.01 (dq, J=7.1, 2.8 Hz, 1H), 2.07 (s, 3H), 2.20 (br d, J=16.3 Hz, 1H), 2.87 (d, J=16.3 Hz, 1H), 4.45 (m, 1H), 4.64 (m, 1H), 5.51 (br d, J=9.5 Hz, 1H), 5.69 (br s, 1H), 6.00 (s, 1H); MS (FAB) m/z 302 (M−H)$^+$.

Example A11b (4aR,5R,6R,7R)-6-Acetylamino-7-hydroxy-4a,5,6,7-tetrahydro-3,4a,5-trimethylnaphtho[2,3-b]furan-2(4H)-one In Example A11a, the title compound (4.8 mg, 8%), together with the compound described in Example A11a, was obtained.

$^1$H NMR (CDCl$_3$) δ 1.09 (s, 3H), 1.13 (d, J=7.2 Hz, 3H), 1.94 (d, J=1.7 Hz, 3H), 2.03 (s, 3H), 2.28 (dq, J=7.2, 4.0 Hz, 1H), 2.32 (br d, J=16.5 Hz, 1H), 2.86 (d, J=16.5 Hz, 1H), 4.14–4.20 (m, 2H), 5.49 (m, 1H), 5.88 (br d, J=4.7 Hz, 1H), 6.02 (s, 1H); MS (FAB) m/z 302 (M−H)$^+$.

Example A12

(4aR,5R,6R,7S)-6-Chloroacetoxy-7-hydroxy-4a,5,6,7-tetrahydro-3,4a,5-trimethylnaphtho[2,3-b]furan-2(4H)-one The title compound (10 mg, 40%) was prepared in the same manner as in Example A2, except that substance PF1092C (19 mg, 0.07 mmol), 4-dimethylaminopyridine (9.0 mg, 0.07 mmol), and chloroacetyl chloride (14 μl, 0.18 mmol) were stirred at 25° C. for 19 hr and the purification was performed by preparative TLC (chloroform:methanol=40:1).

$^1$H NMR (CDCl$_3$) δ 1.15 (d, J=7.2 Hz, 3H), 1.18 (s, 3H), 1.93 (d, J=1.4 Hz, 3H), 2.05 (dq, J=7.2, 1.8 Hz, 1H), 2.22 (br d, J=16.2 Hz, 1H), 2.86 (d, J=16.2 Hz, 1H), 4.15 (s, 2H), 4.59 (m, 1H), 5.38 (m, 1H), 5.67 (br s, 1H), 6.00 (s, 1H); MS (EI) m/z 338 (M)$^+$.

Example A13

(4aR,5R,6R,7S)-7-Hydroxy-6-phenylacetoxy-4a,5,6,7-tetrahydro-3,4a,5-trimethylnaphtho[2,3-b]furan-2(4H)-one The title compound (9.4 mg, 34%) was prepared in the same manner as in Example A5, except that substance PF1092C (19 mg, 0.07 mmol), diisopropylethylamine (32 μl, 0.18 mmol), and phenylacetyl chloride (24 μl, 0.18 mmol) were stirred at 25° C. for 16 hr and the purification was performed by preparative TLC (hexane:ethyl acetate=1:1).

$^1$H NMR (CDCl$_3$) δ 0.97 (d, J=0.8 Hz, 3H), 1.00 (d, J=7.2 Hz, 3H), 1.90 (d, J=1.9 Hz, 3H), 1.95 (dq, J=7.2, 1.8 Hz, 1H), 2.16 (br d, J=16.3 Hz, H), 2.79 (d, J=16.3 Hz, 1H), 3.70 (s, 1H), 3.71 (s, 1H), 4.49 (m, 1H), 5.28 (ddd, J=5.1, 1.8, 1.8 Hz, 1H), 5.62 (br s, 1H), 5.96 (s, 1H), 7.28 (m, 5H); MS (SIMS) m/z 381 (M+H)$^+$.

Example A14

(4aR,5R,6R,7S)-6-(2-Furancarbonyl)oxy-7-propionyloxy-4a,5,6,7-tetrahydro-3,4a,5-trimethylnaphtho[2,3-b]furan-2(4H)-one The title compound (70 mg, 90%) was prepared in the same manner as in Example A3, except that the compound (60 mg, 0.19 mmol) prepared in Example A1,4-dimethylaminopyridine (103 mg, 0.84 mmol), and 2-furoyl chloride (74 μl, 0.75 mmol) were stirred at 25° C. for 30 min and the purification was performed by column chromatography on silica gel (toluene:ethyl acetate=10:1).

$^1$H NMR (CDCl$_3$) δ 1.07 (t, J=7.5 Hz, 3H), 1.17 (d, J=7.1 Hz, 3H), 1.32 (s, 3H), 1.95 (d, J=1.5 Hz, 3H), 2.16 (dq, J=7.1, 1.8 Hz, 1H), 2.26 (q, J=7.5 Hz, 2H), 2.28 (br d, J=16.7 Hz, 1H), 2.91 (d, J=16.7 Hz, 1H), 5.59 (ddd, J=4.8, 1.8, 1.8 Hz, 1H), 5.62 (br s, 1H), 5.73 (m, 1H), 6.03 (s, 1H), 6.53 (dd, J=3.5, 1.7 Hz, 1H), 7.17 (br d, J=3.5, 0.8 Hz, 1H), 7.60 (m, 1H); MS (FAB) m/z 413 (M+H)$^+$.

Example A15

(4aR,5R,6R,7S)-7-Cyclopropylcarbonyloxy-6-propionyloxy-4a,5,6,7-tetrahydro-3,4a,5-trimethylnaphtho[2,3-b]furan-2(4H)-one The title compound (70 mg, 96%) was prepared in the same manner as in Example A3, except that the compound (60 mg, 0.19 mmol) prepared in Example A2, anhydrous pyridine (151 μl, 1.87 mmol), and cyclopropanecarbonyl chloride (68 μl, 0.75 mmol) were stirred at 25° C. for 30 min and the purification was performed by column chromatography on silica gel (toluene:ethyl acetate=20:1).

$^1$H NMR (CDCl$_3$) δ 0.89 (m, 2H), 1.02 (m, 2H), 1.10 (d, J=7.1 Hz, 3H), 1.19 (t, J=7.6 Hz, 3H), 1.20 (s, 3H), 1.55 (m, 1H), 1.93 (d, J=1.5 Hz, 3H), 2.05 (dq, J=7.1, 2.1 Hz, 1H), 2.23 (br d, J=16.2 Hz, 1H), 2.40 (q, J=7.6 Hz, 2H), 2.87 (d, J=16.2 Hz, 1H), 5.43 (m, 1H), 5.59 (m, 1H), 5.60 (br s, 1H), 5.99 (s, 1H); MS (TSI) m/z 387 (M+H)$^+$.

Example A16

(4aR,5R,6R,7S)-7-Hydroxy-6-(2-methylpropionyl)oxy-4a,5,6,7-tetrahydro-3,4a,5-trimethylnaphtho[2,3-b]furan-2(4H)-one The title compound (3.8 mg, 32%) was prepared in the same manner as in Example A5, except that substance PF1092C (9.3 mg, 0.04 mmol), diisopropylethylamine (61 μl, 0.35 mmol), and isobutylyl chloride (37 μl, 0.35 mmol) were stirred at 25° C. for 19 hr and the purification was performed by preparative TLC (chloroform:methanol=100:1).

$^1$H NMR (CDCl$_3$) δ 1.12 (d, J=7.2 Hz, 3H), 1.18 (s, 3H), 1.23, 1.23 (each d, J=6.9 Hz, 6H), 1.93 (d, J=1.8 Hz, 3H), 2.02 (dq, J=7.2, 2.1 Hz, 1H), 2.22 (br d, J=16.0 Hz, 1H), 2.66 (sep, J=6.9 Hz, 1H), 2.86 (d, J=16.0 Hz, 1H), 4.57 (m, 1H), 5.30 (m, 1H), 5.68 (br s, 1H), 6.00 (s, 1H); MS (EI) m/z 332 (M)$^+$.

Example A17

(4aR,5R,6R,7S)-6-Cyclopropylcarbonyloxy-7-hydroxy-4a,5,6,7-tetrahydro-3,4a,5-trimethylnaphtho[2,3-b]furan-2(4H)-one The procedure of Examples A3 (1) and (2) was repeated, except that 7-0-(t-butyldimethylsilyl) derivative of PF1092C (37 mg, 0.10 mmol), 4-dimethylaminopyridine (59 mg, 0.49 mmol), and cyclopropanecarbonyl chloride (40 μl, 0.44 mmol) were stirred at 25° C. for 17 hr and the purification was performed by preparative TLC (toluene:ethyl acetate=20:1). Thus, a corresponding 7-0-(t-butyldimethylsilyl)-6-0-cyclopropylcarbonyl derivative (40 mg, 93%) was prepared.

Further, the procedure of Example A3 (3) was repeated, except that the compound (40 mg, 0.09 mmol) prepared just above and a 1.0 M solution of tetrabutylammonium fluoride in THF (100 μl, 0.10 mmol) were stirred at 25° C. for 2 hr and the purification was performed by preparative TLC (hexane:ethyl acetate=1:1). Thus, the title compound (15 mg, 51%) was prepared.

$^1$H NMR (CDCl$_3$) δ 0.93 (m, 2H), 1.05 (m, 2H), 1.13 (d, J=7.1 Hz, 3H), 1.20 (s, 3H), 1.65 (m, 1H), 1.93 (d, J=1.7 Hz, 3H), 2.00 (dq, J=7.1, 1.8 Hz, 1H), 2.21 (br d, J=16.0 Hz, 1H), 2.81 (d, J=16.0 Hz, 1H), 4.55 (m, 1H), 5.30 (ddd, J=5.0, 1.8, 1.8 Hz, 1H), 5.69 (br s, 1H), 6.00 (s, 1H); MS (EI) m/z 330 (M)$^+$.

Example A18

(4aR,5R,6R,7S)-7-Cyclohexylcarbonyloxy-6-hydroxy-4a,5,6,7-tetrahydro-3,4a,5-trimethylnaphtho[2,3-b]furan-2(4H)-one The title compound (5.2 mg, 41%) was prepared in the same manner as in Example A1, except that substance PF1092C (8.9 mg, 0.03 mmol), diisopropylethylamine (15 μl, 0.09 mmol), and cyclohexanecarbonyl chloride (10 μl, 0.07 mmol) were stirred at 25° C. for 5 hr and the purification was performed by preparative TLC (toluene:ethyl acetate=8:1).

$^1$H NMR (CDCl$_3$) δ 1.24 (br s, 3H), 1.25 (d, J=7.3 Hz, 3H), 1.28–2.00 (m, 10H), 1.86 (dq, J=7.3, 1.8 Hz, 1H), 1.93 (d, J=1.6 Hz, 3H), 2.21 (br d, J=16.4 Hz, 1H), 2.41 (m, 1H), 2.87 (d, J=16.4 Hz, 1H), 4.05 (m, 1H), 5.48 (m, 1H), 5.56 (br s, 1H), 5.97 (s, 1H); MS (EI) m/z 372 (M)$^+$.

Example A19

(4aR,5R,6R,7S)-6-Cyclohexylcarbonyloxy-7-hydroxy-4a,5,6,7-tetrahydro-3,4a,5-trimethylnaphtho[2,3-b]furan-2(4H)-one The title compound (6.2 mg, 48%) was prepared in the same manner as in Example A2, except that substance PF1092C (9.0 mg, 0.03 mmol), 4-dimethylaminopyridine (4.4 mg, 0.04 mmol), and cyclohexanecarbonyl chloride (11 μl, 0.08 mmol) were stirred at 25° C. for 6 hr and the purification was performed by preparative TLC (toluene ethyl acetate=8:1).

$^1$H NMR (CDCl$_3$) δ 1.11 (d, J=7.1 Hz, 3H), 1.19 (br s, 3H), 1.22–1.96 (m, 10H), 1.93 (d, J=1.7 Hz, 3H), 2.01 (dq, J=7.1, 1.9 Hz, 1H), 2.21 (br d, J=16.3 Hz, 1H), 2.39 (m, 1H), 2.85 (d, J=16.3 Hz, 1H), 4.55 (m, 1H), 5.30 (ddd, J=5.2, 1.9, 1.9 Hz, 1H), 5.68 (br s, 1H), 6.00 (s, 1H); MS (EI) m/z 372 (M)$^+$.

Example A20

(4aR,5R,6R,7S)-6-Cinnamoyloxy-7-hydroxy-4a,5,6,7-tetrahydro-3,4a,5-trimethylnaphtho[2,3-b]furan-2(4H)-one The procedure of Examples A3 (1) and (2) was repeated, except that 7-0-(t-butyldimethylsilyl) derivative of PF1092C (30 mg, 0.08 mmol), 4-dimethylaminopyridine (50 mg, 0.41 mmol), and cinnamoyl chloride (120 mg, 0.72 mmol) were stirred at 25° C. for 2 days and the purification was performed by preparative TLC (hexane:ethyl acetate=4:1). Thus, a corresponding 7-0-(t-butyldimethylsilyl)-6-0-cinnamonyl derivative (22 mg, 54%) was prepared.

Further, the procedure of Example A3 (3) was repeated, except that the compound (22 mg, 0.04 mmol) prepared just above and a 1.0 M solution of tetrabutylammonium fluoride in THF (47 μl, 0.05 mmol) were stirred at 25° C. for 2.5 hr and the purification was performed by preparative TLC (hexane:ethyl acetate=1:1). Thus, the title compound (8.6 mg, 52%) was prepared.

$^1$H NMR (CDCl$_3$) δ 1.17 (d, J=7.1 Hz, 3H), 1.26 (s, 3H), 1.94 (d, J=1.7 Hz, 3H), 2.07 (dq, J=7.1, 1.8 Hz, 1H), 2.24 (br d, J=16.5 Hz, 1H), 2.88 (d, J=16.5 Hz, 1H), 4.62 (m, 1H), 5.47 (ddd, J=5.1, 1.8, 1.8 Hz, 1H), 5.73 (br s, 1H), 6.03 (s, 1H), 6.47 (d, J=16.0 Hz, 1H), 7.40 (m, 3H), 7.53 (m, 2H), 7.74 (d, J=16.0 Hz, 1H); MS (TSPI) m/z 393 (M+H)$^+$.

Example A21

(4aR,5R,6R,7S)-6-Benzoyloxy-7-hydroxy-4a,5,6,7-tetrahydro-3,4a,5-trimethylnaphtho[2,3-b]furan-2(4H)-one The title compound (25 mg, 74%) was prepared in the same manner as in Example A5, except that substance PF1092C (24 mg, 0.09 mmol), diisopropylethylamine (64 μl, 0.37 mmol), and benzoic anhydride (202 mg, 0.89 mmol) were stirred at 25° C. for 20 hr and the purification was performed by preparative TLC (hexane:ethyl acetate=1

$^1$H NMR (CDCl$_3$) δ 1.19 (d, J=7.2 Hz, 3H), 1.30 (s, 3H), 1 94 (d, J=1.7 Hz, 3H), 2.14 (dq, J=7.2, 1.8 Hz, 1H), 2.26 (br d, J=16.2 Hz, 1H), 2.90 (d, J=16.2 Hz, 1H), 4.66 (m, 1H), 5.61 (ddd, J=5.1, 1.8, 1.8 Hz, 1H), 5.75 (br s, 1H), 6.05 (s, 1H), 7.46 (m, 2H), 7.59 (m, 1H), 8.03 (m, 2H); MS (SIMS) m/z 367 (M+H)$^+$.

Example A22

(4aR,5R,6R,7S)-6-Hydroxy-7-(4-nitrobenzoyl)oxy-4a,5,6,7-tetrahydro-3,4a,5-trimethylnaphtho[2,3-b]furan-2(4H)-one The title compound (3.8 mg, 24%) was prepared in the same manner as in Example A1, except that substance PF1092C (10 mg, 0.04 mmol), diisopropylethylamine (10 μl, 0.06 mmol), and 4-nitrobenzoyl chloride (9.1 mg, 0.05 mmol) were stirred at 25° C. for 22 hr and the purification was performed by preparative TLC (toluene:ethyl acetate=4:1).

$^1$H NMR (CDCl$_3$) δ 1.29 (br s, 3H), 1.30 (d, J=7.1 Hz, 3H), 1.95 (d, J=1.8 Hz, 3H), 1.95 (dq, J=7.1, 1.7 Hz, 1H), 2.26 (br d, J=16.4 Hz, 1H), 2.91 (d, J=16.4 Hz, 1H), 4.24 (m, 1H), 5.71 (br s, 1H), 5.78 (m, 1H), 6.02 (s, 1H), 8.30 (m, 4H); MS (EI) m/z 411 (M)$^+$.

Example A23

(4aR,5R,6R,7S)-7-Hydroxy-6-(4-nitrobenzoyl)oxy-4a,5,6,7-tetrahydro-3,4a,5-trimethylnaphtho[2,3-b]furan-2(4H)-one The title compound (2.1 mg, 22%) was prepared in the same manner as in Example A2, except that substance PF1092C (9.7 mg, 0.04 mmol), 4-dimethylaminopyridine (4.5 mg, 0.04 mmol), and 4-nitrobenzoyl chloride (8.4 mg, 0.05 mmol) were stirred at 25° C. for 22 hr and the purification was performed by preparative TLC (toluene:ethyl acetate=4:1).

$^1$H NMR (CDCl$_3$) δ 1.29 (br s, 3H), 1.70 (d, J=7.2 Hz, 3H), 1.95 (d, J=1.7 Hz, 3H), 2.17 (dq, J=7.2, 1.9 Hz, 1H), 2.28 (br d, J=16.4 Hz, 1H), 2.91 (d, J=16.4 Hz, 1H), 4.71 (m, 1H), 5.63 (ddd, J=5.1, 1.9, 1.9 Hz, 1H), 5.74 (br s, 1H), 6.05 (s, 1H), 8.18 (m, 2H), 8.31 (m, 2H); MS (EI) m/z 411 (M)$^+$.

Example A24

(4aR,5R,6R,7S)-6,7-Di[(2-furancarbonyl)oxy]-4a,5,6,7-tetrahydro-3,4a,5-trimethylnaphtho[2,3-b]furan-2(4H)-one The title compound (20 mg, 83%) was prepared in the same manner as in Example A4, except that substance PF1092C (14 mg, 0.05 mmol), 4-dimethylaminopyridine (35 mg, 0.28 mmol), and 2-furoyl chloride (24 μl, 0.24 mmol) were stirred at 25° C. for 4 hr and the purification was performed by preparative TLC (toluene:ethyl acetate=4:1).

$^1$H NMR (CDCl$_3$) δ 1.20 (d, J=7.1 Hz, 3H), 1.35 (s, 3H), 1.95 (d, J=1.7 Hz, 3H), 2.21 (dq, J=7.1, 1.8 Hz, 1H), 2.30 (br d, J=16.2 Hz, 1H), 2.93 (d, J=16.2 Hz, 1H), 5.69 (ddd, J=4.8, 1.8, 1.8 Hz, 1H), 5.73 (m, 1H), 5.91 (m, 1H), 6.04 (s, 1H), 6.42 (dd, J=3.5, 1.8 Hz, 1H), 6.53 (dd, J=3.4, 1.7 Hz, 1H), 6.93 (br d, J=3.5 Hz, 1H), 7.18 (br d, J=3.4 Hz, 1H), 7.50 (m, 1H), 7.60 (m, 1H); MS (ESI) m/z 468 (M+NH$_4$)$^+$, 473 (M+Na)$^+$.

Example A25

(4aR,5R,6R,7S)-7-Hydroxy-6-(4-methyl-5-thiazolylcarbonyl)oxy-4a,5,6,7-tetrahydro-3,4a,5-trimethylnaphtho[2,3-b]furan-2(4H)-one The procedure of Examples A3 (1) and (2) was repeated, except that 7-0-(t-butyldimethylsilyl) derivative of PF1092C (40 mg, 0.11 mmol), 4-dimethylaminopyridine (130 mg, 1.07 mmol), and 4-methyl-5-thiazole)carbonyl chloride hydrochloride (99 mg, 0.50 mmol) were stirred at 25° C. for 8 hr and the purification was performed by column chromatography on silica gel (hexane:ethyl acetate=5:1). Thus, a corresponding 7-0-(t-butyldimethylsilyl)-6-0-(4-methyl-5-thiazolyl)carbonyl derivative (45 mg, 85%) was prepared.

Further, the procedure of Example A3 (3) was repeated, except that the above compound (36 mg, 0.07 mmol) and a 1.0 M solution of tetrabutylammonium fluoride in THF (78 μl, 0.08 mmol) were stirred under ice cooling for 30 min and the purification was performed by preparative TLC (hexane:ethyl acetate=1:2). Thus, the title compound (10 mg, 37%) was prepared.

$^1$H NMR (CDCl$_3$) δ 1.19 (d, J=7.2 Hz, 3H), 1.25 (s, 3H), 1.94 (d, J=1.9 Hz, 3H), 2.10 (dq, J=7.2, 1.9 Hz, 1H), 2.24 (br d, J=16.3 Hz, 1H), 2.80 (s, 3H), 2.88 (d, J=16.3 Hz, 1H), 4.64 (m, 1H), 5.50 (ddd, J=5.1, 1.9, 1.9 Hz, 1H), 5.71 (br s, 1H), 6.02 (s, 1H), 8.78 (s, 1H); MS (ESI) m/z 388 (M+H)$^+$.

Example A26

(4aR,5R,6R,7S)-6-(1-Benzothiophen-2-ylcarbonyl)oxy-7-hydroxy-4a,5,6,7-tetrahydro-3,4a,5-trimethylnaphtho[2,3-b]furan- 2(4H)-one The procedure of Examples A3 (1) and (2) was repeated, except that 7-0-(t-butyldimethylsilyl) derivative of PF1092C (42 mg, 0.11 mmol), 4-dimethylaminopyridine (69 mg, 0.57 mmol), and 1-benzothiophene-2-carbonyl chloride (102 mg, 0.52 mmol) were stirred at 25° C. for 22 hr and the purification was performed by preparative TLC (toluene:ethyl acetate=20: 1). Thus, a corresponding 6-0-(1-benzothiophen-2-ylcarbonyl)-7-0-(t-butyldimethylsilyl) derivative (56 mg, 95%) was prepared.

Further, the procedure of Example A3 (3) was repeated, except that the above compound (56 mg, 0.11 mmol) and hydrogen fluoride-pyridine complex (0.13 ml) were stirred at 25° C. for 3 hr and the purification was performed by preparative TLC (toluene:ethyl acetate=3:1). Thus, the title compound (36 mg, 82%) was prepared.

$^1$H NMR (CDCl$_3$) δ 1.21 (d, J=7.1 Hz, 3H), 1.33 (s, 3H), 1.94 (d, J=1.7 Hz, 3H), 2.11 (dq, J=7.1, 1.8 Hz, 1H), 2.23 (br d, J=16.3 Hz, 1H), 2.89 (d, J=16.3 Hz, 1H), 4.65 (m, 1H), 5.56 (ddd, J=5.1, 1.8, 1.8 Hz, 1H), 5.73 (br s, 1H), 6.03 (s, 1H), 7.44 (m, 2H), 7.86 (m, 2H), 8.07 (s, 1H); MS (TSI) m/z 423 (M+H)$^+$.

Example A27

(4aR,5R,6R,7S)-6-Hydroxy-7-methylcarbamoyloxy-4a,5,6,7-tetrahydro-3,4a,5-trimethylnaphtho[2,3-b]furan-2(4H)-one The title compound (3.1 mg, 15%) was prepared in the same manner as in Example A6a, except that substance PF1092C (17 mg, 0.06 mmol) and methyl isocyanate (19 μl, 0.32 mmol) were stirred at 35° C. for 9 hr and the purification was performed by preparative TLC (hexane:ethyl acetate=1:1).

$^1$H NMR (CDCl$_3$) δ 1.24 (br s, 3H), 1.25 (d, J=7.1 Hz, 3H), 1.86 (dq, J=7.1, 1.7 Hz, 1H), 1.93 (d, J=1.7 Hz, 3H), 2.21 (br d, J=16.2 Hz, 1H), 2.85 (d, J=4.9 Hz, 3H), 2.86 (d, J=16.2 Hz, 1H), 4.09 (m, 1H), 4.79 (m, 1H), 5.41 (m, 1H), 5.61 (br s, 1H), 5.97 (s, 3H); MS (FD) m/z 319 (M)$^+$.

Example A28

(4aR,5R,6R,7S)-6,7-Di(phenylcarbamoyloxy)-4a,5,6,7-tetrahydro-3,4a,5-trimethylnaphtho[2,3-b]furan-2(4H)-one The title compound (40 mg, 33%) was prepared in the same manner as in Example A6a, except that substance PF1092C (63 mg, 0.24 mmol), 4-dimethylaminopyridine (3.5 mg, 0.03 mmol), and phenyl isocyanate (260 μl, 2.39 mmol) were stirred at 25° C. for 2 hr and the purification was performed by column chromatography on silica gel (toluene:ethyl acetate=10:1).

$^1$H NMR (CDCl$_3$) δ 1.20 (d, J=7.0 Hz, 3H), 1.21 (s, 3H), 1.94 (br s, 3H), 2.10 (dq, J=7.0, 1.7 Hz, 1H), 2.25 (br d, J=16.2 Hz, 1H), 2.89 (d, J=16.2 Hz 1H), 5.46 (ddd, J=4.7, 1.7, 1.7 Hz, 1H), 5.67 (m, 1H), 5.72 (br s, 1H), 6.00 (s, 1H), 6.70 (br s, 1H), 6.86 (br s, 1H), 7.07 (m, 2H), 7.28 (m, 8H), 7.41 (m, 2H); MS (FD) m/z 500 (M)$^+$.

Example A29

(4aR,5R,6R,7S)-6,7-Dimethoxy-4a,5,6,7-tetrahydro-3,4a,5-trimethylnaphtho[2,3-b]furan-2(4H)-one The title compound (268 mg, 24%) was prepared in the same manner as in Example A7, except that substance PF1092C (1.0 g, 3.83 mmol), 60% sodium hydride (264 mg, 6.61 mmol), and methyl iodide (4.1 ml, 65.9 mmol) in DMF were stirred at 25° C. for 1.5 hr and the purification was performed by column chromatography on silica gel (toluene:ethyl acetate=20:1).

$^1$H NMR (CDCl$_3$) δ 1.18 (s, 3H), 1.21 (d, J=7.1 Hz, 3H), 1.91 (d, J=1.9 Hz, 3H), 1.75 (dq, J=7.1, 1.7 Hz, 1H), 2.14 (br d,J=16.3 Hz, 1H), 2.83 (d, J=16.3 Hz, 1H), 3.51 (s, 3H), 3.58 (m, 1H), 3.59 (s, 3H), 3.98 (m, 1H), 5.78 (br s, 1H), 5.98 (s, 1H); MS (TSI) m/z 291 (M+H)$^+$.

Example A30

(4aR,5R,6R,7S)-6-Acetoxy-7-methoxy-4a,5,6,7-tetrahydro-3,4a, 5-trimethylnaphtho[2,3-b]furan-2 (4H)-one The procedure of Example A29 was repeated, except that substance PF1092C (19 mg, 0.07 mmol), 60% sodium hydride (4.5 mg, 0.11 mmol), and methyl iodide (36 μl, 0.57 mmol) were stirred at −15° C. for 1 hr and the purification was performed by preparative TLC (hexane:ethyl acetate=1:1). Thus, a corresponding 7-0-methyl derivative (9.0 mg, 47%) was obtained.

Further, the procedure of Example A8 was repeated, except that the compound (9.0 mg, 0.03 mmol) prepared just above, 4-dimethylaminopyridine (21 mg, 0.17 mmol), and acetyl chloride (10 µl, 0.14 mmol) were stirred at 25° C. for 3 hr and the purification was performed by preparative TLC (toluene:ethyl acetate=4:1). Thus, the title compound (8.0 mg, 78%) was obtained.

$^1$H NMR (CDCl$_3$) δ 1.11 (d, J=7.2 Hz, 3H), 1.16 (s, 3H), 1.92 (d, J=1.7 Hz, 3H), 1.95 (dq, J=7.2, 1.7 Hz, 1H), 2.12 (s, 3H), 2.20 (br d, J=16.4 Hz, 1H), 2.85 (d, J=16.4 Hz, 1H), 3.42 (s, 3H), 3.99 (m, 1H), 5.49 (ddd, J=4.6, 1.7, 1.7 Hz, 1H), 5.71 (br s, 1H), 5.99 (s, 1H); MS (ESI) m/z 319 (M+H)$^+$.

Example A31

(4aR,5R,6R,7S)-6-(2-Furancarbonyl)oxy-7-methoxy-4a,5,6,7-tetrahydro-3,4a,5-trimethylnaphtho[2,3-b]furan-2(4H)-one The title compound (17 mg, 91%) was prepared in the same manner as in Example A30, except that a 7-0-methyl derivative of substance PF1092C (14 mg, 0.05 mmol), 4-dimethylaminopyridine (32 mg, 0.26 mmol), and 2-furoyl chloride (23 µl, 0.23 mmol) were stirred at 25° C. for 14 hr and the purification was performed by preparative TLC (hexane:ethyl acetate=1:1).

$^1$H NMR (CDCl$_3$) δ 1.16 (d, J=7.1 Hz, 3H), 1.26 (d, J=0.8 Hz, 3H), 1.93 (d, J=1.7 Hz, 3H), 2.05 (dq, J=7.1, 1.7 Hz, 1H), 2.24 (br d, J=16.2 Hz, 1H), 2.88 (d, J=16.2 Hz, 1H), 3.44 (s, 3H), 4.07 (m, 1H), 5.70 (ddd, J=4.7, 1.7, 1.7 Hz, 1H), 5.75 (br s, 1H), 6.03 (s, 1H), 6.50 (dd, J=3.5, 1.8 Hz, 1H), 7.15 (dd, J=3.5, 0.8 Hz, 1H), 7.58 (dd, J=1.8, 0.8 Hz, 1H); MS (FAB) m/z 371 (M+H)$^+$.

Example A32

(4aR,5R,6R,7S)-7-Methoxy-6-(2-thiophenecarbonyl)oxy-4a,5,6,7-tetrahydro-3,4a,5-trimethylnaphtho[2,3-b]furan-2(4H)-one The title compound (7.7 mg, 73%) was prepared in the same manner as in Example A30, except that a 7-0-methyl derivative of substance PF1092C (7.5 mg, 0.03 mmol), 4-dimethylaminopyridine (17 mg, 0.14 mmol), and 2-thenoyl chloride (13 µl, 0.12 mmol) were stirred at 25° C. for 15 hr and the purification was performed by preparative TLC (hexane:ethyl acetate=1:1).

$^1$H NMR (CDCl$_3$) δ 1.18 (d, J=7.1 Hz, 3H), 1.28 (s, 3H), 1.94 (d, J=1.8 Hz, 3H), 2.06 (dq, J=7.1, 1.8 Hz, 1H), 2.25 (br d, J=16.2 Hz, 1H), 2.89 (d, J=16.2 Hz, 1H), 3.44 (s, 3H), 4.08 (ddd, J=4.7, 1.8, 1.8 Hz, 1H), 5.70 (m, 1H), 5.76 (br s, 1H), 6.05 (s, 1H), 7.11 (dd, J=5.0, 3.7 Hz, 1H), 7.57 (dd, J=5.0, 1.1 Hz, 1H), 7.80 (dd, J=3.7, 1.1 Hz, 1H); MS (FAB) m/z 387 (M+H)$^+$.

Example A33

(4aR,5R,6R,7S)-6-Acetoxy-7-(n-propyl)oxy-4a,5,6,7-tetrahydro-3,4a,5-trimethylnaphtho[2,3-b]furan-2(4H)-one The procedure of Example A29 was repeated, except that substance PF1092C (200 mg, 0.76 mmol), 60% sodium hydride (80 mg, 2.0 mmol) and n-propyl iodide (1.0 ml, 10.3 mmol) were stirred at 0° C. for 10 min and the purification was performed by column chromatography on silica gel (hexane:ethyl acetate=6:1). Thus, a corresponding 7-0-(n-propyl) derivative (87 mg, 37%) was prepared.

Further, the procedure of Example A30 was repeated, except that the compound (33 mg, 0.11 mmol) prepared just above, anhydrous pyridine (44 µl, 0.54 mmol), and acetyl chloride (35 µl, 0.49 mmol) were stirred at 25° C. for 8.5 hr and the purification was performed by preparative TLC (toluene:ethyl acetate=4:1). Thus, the title compound (30 mg, 79%) was obtained.

$^1$H NMR (CDCl$_3$) δ 0.90 (t, J=6.9 Hz, 3H), 1.10 (d, J=7.2 Hz, 3H), 1.15 (d, J=0.8 Hz, 3H), 1.55 (seq, J=6.9 Hz, 2H), 1.91 (d, J=1.4 Hz, 3H), 1.94 (dq, J=7.2, 1.7 Hz, 1H), 2.10 (s, 3H), 2.18 (br d, J=17.1 Hz, 1H), 2.84 (d, J=17.1 Hz, 1H), 3.38 (q, J=6.9 Hz, 1H), 3.58 (q, J=6.9 Hz, 1H), 4.06 (m, 1H), 5.47 (ddd, J=4.8, 1.7, 1.7 Hz, 1H), 5.70 (br s, 1H), 5.98 (s, 1H); MS (TSI) m/z 347 (M+H)$^+$.

Example A34

(4aR,5R,6R,7S)-6-Ethoxycarbonyloxy-7-methoxy-4a,5,6,7-tetrahydro-3,4a,5-trimethylnaphtho[2,3-b]furan-2(4H)-one The title compound (5.0 mg, 41%) was prepared in the same manner as in Example A30, except that a 7-0-methyl derivative of substance PF1092C (9.7 mg, 0.04 mmol), 4-dimethylaminopyridine (22 mg, 0.18 mmol), and ethoxycarbonyl chloride (15 µl, 0.16 mmol) were stirred at 25° C. for 19 hr and the purification was performed by preparative TLC (toluene:ethyl acetate=4:1).

$^1$H NMR (CDCl$_3$) δ 1.18 (d, J=0.8 Hz, 3H), 1.18 (d, J=7.1 Hz, 3H), 1.31 (t, J=7.1 Hz, 3H), 1.86 (d, J=1.9 Hz, 3H), 1.94 (dq, J=7.1, 1.7 Hz, 1H), 2.20 (br d, J=16.3 Hz, 1H), 2.86 (d, J=16.3 Hz, 1H), 3.46 (s, 3H), 4.00 (m, 1H), 4.21, 4.22 (each q, J=7.1 Hz, 2H), 5.26 (ddd, J=4.6, 1.7, 1.7 Hz, 1H), 5.73 (br s, 1H), 5.99 (s, 1H); MS (EI) m/z 348 (M)$^+$.

Example A35

(4aR,5R,6R,7S)-7-Methoxy-6-phenoxycarbonyloxy-4a,5,6,7-tetrahydro-3,4a,5-trimethylnaphtho[2,3-b]furan-2(4H)-one The title compound (6.7 mg, 60%) was prepared in the same manner as in Example A30, except that a 7-0-methyl derivative of substance PF1092C (7.8 mg, 0.03 mmol), 4-dimethylaminopyridine (37 mg, 0.31 mmol), and phenoxycarbonyl chloride (32 µl, 0.26 mmol) were stirred at 25° C. for 18 hr and the purification was performed by preparative TLC (toluene:ethyl acetate=4:1).

$^1$H NMR (CDCl$_3$) δ 1.13 (s, 3H), 1.24 (d, J=7.1 Hz, 3H), 1.93 (d, J=1.7 Hz, 3H), 2.00 (dq, J=7.1, 1.8 Hz, 1H), 2.21 (br d, J=16.2 Hz, 1H), 2.88 (d, J=16.2 Hz, 1H), 3.51 (s, 3H), 4.05 (m, 1H), 5.34 (ddd, J=4.6, 1.8, 1.8 Hz, 1H), 5.75 (br s, 1H), 6.00 (s, 1H), 7.17–7.41 (m, 3H), 7.38 (m, 2H); MS (EI) m/z 396 (M)$^+$.

Example A36

(4aR,5R,6R,7S)-6-Methoxymethoxy-7-propionyloxy-4a,5,6,7-tetrahydro-3,4a,5-trimethylnaphtho[2,3-b]furan-2(4H)-one The procedure of Example A8 (1) was repeated, except that substance PF1092C (202 mg, 0.77 mmol), diisopropylethylamine (160 µl, 0.92 mmol) and methoxymethyl chloride (64 µl, 0.84 mmol) were stirred at 25° C. for 23 hr and the purification was performed by column chromatography on silica gel (toluene:ethyl acetate=6:1). Thus, a corresponding 6-0-methoxymethyl derivative (35 mg, 18%) was prepared.

Further, the procedure of Example A8 (2) was repeated, except that the compound (18 mg, 0.06 mmol) prepared just above, 4-dimethylaminopyridine (19 mg, 0.15 mmol) and propionyl chloride (11 µl, 0.14 mmol) were stirred at 25° C. for 4 hr and the purification was performed by preparative TLC (toluene:ethyl acetate=5:1). Thus, the title compound (16 mg, 77%) was obtained.

$^1$H NMR (CDCl$_3$) δ 1.18 (t, J=7.6 Hz, 3H), 1.21 (d, J=7.1 Hz, 3H), 1.22 (s, 3H), 1.91 (dq, J=7.1, 1.7 Hz, 1H), 1.92 (d, J=1.7 Hz, 3H), 2.20 (br d, J=16.3 Hz, 1H), 2.41, 2.42 (each q, J=7.6 Hz, 2H), 2.87 (d, J=16.3 Hz, 1H), 3.42 (s, 3H), 3.96 (m, 1H), 4.66 (d, J=6.8 Hz, 1H), 4.70 (d, J=6.8 Hz, 1H), 5.51 (m, 1H), 5.60 (br s, 1H), 5.97 (s, 1H); MS (FD) m/z 362 (M)$^+$.

Example A37

(4aR,5R,6R,7S)-7-Benzoyloxy-6-methoxymethoxy-4a,5,6,7-tetrahydro-3,4a,5-trimethylnaphtho[2,3-b]furan-2(4H)-one The title compound (4.8 mg, 42%) was prepared in the same manner as in Example A36, except that a 6-0-methoxymethyl derivative of substance PF1092C (8.6 mg, 0.03 mmol), 4-dimethylaminopyridine (22 mg, 0.18 mmol), and benzoyl chloride (17 µl, 0.15 mmol) were stirred at 25° C. for 18 hr and the purification was performed by preparative TLC (toluene:ethyl acetate=5:1).

$^1$H NMR (CDCl$_3$) δ 1.25 (d, J=7.1 Hz, 3H), 1.27 (s, 3H), 1.94 (d, J=1.4 Hz, 3H), 2.00 (dq, J=7.1, 1.5 Hz, 1H), 2.25 (br d, J=16.1 Hz, 1H), 2.89 (d, J=16.1 Hz, 1H), 3.32 (s, 3H), 4.10 (m, 1H), 4.68 (d, J=6.8 Hz, 1H), 4.73 (d, J=6.8 Hz, 1H), 5.74 (br s, 1H), 5.75 (m, 1H), 6.02 (s, 1H), 7.46 (m, 2H), 7.60 (m, 1H), 8.10 (m, 2H); MS (SIMS) m/z 411 (M+H)$^+$.

Example A38

(4aR,5R,6R,7S)-6-Benzoyloxy-7-(2-methoxyethoxymethoxy)-4a,5,6,7-tetrahydro-3,4a,5-trimethylnaphtho[2,3-b]furan-2(4H)-one The procedure of Example A8 (1) and (2) was repeated, except that substance PF1092C (116 mg, 0.44 mmol), diisopropylethylamine (115 µl, 0.66 mmol) and (2-methoxyethoxy)methyl chloride (76 µl, 0.67 mmol) were stirred at 25° C. for 23 hr and the purification was performed by column chromatography on silica gel (hexane:ethyl acetate=1:1). Thus, a corresponding 7-0-(2-methoxyethoxy) methyl derivative (74 mg, 48%) was prepared.

Further, the procedure of Example A8 (3) was repeated, except that the compound (44 mg, 0.13 mmol) prepared just above, 4-dimethylaminopyridine (53 mg, 0.44 mmol) and benzoyl chloride (36 µl, 0.31 mmol) were stirred at 25° C. for 24 hr and the purification was performed by preparative TLC (toluene:ethyl acetate=5:1). Thus, the title compound (22 mg, 38%) was obtained.

$^1$H NMR (CDCl$_3$) δ 1.16 (d, J=7.1 Hz, 3H), 1.27 (s, 3H), 1.94 (d, J=1.6 Hz, 3H), 2.10 (dq, J=7.1, 1.8 Hz, 1H), 2.26 (br d, J=16.0 Hz, 1H), 2.89 (d, J=16.0 Hz, 1H), 3.39 (s, 3H), 3.55 (m, 2H), 3.64 (m, 1H), 3.77 (m, 1H), 4.62 (m, 1H), 4.65 (d, J=7.2 Hz, 1H), 4.88 (d, J=7.2 Hz, 1H), 5.69 (ddd, J=4.8, 1.8, 1.8 Hz, 1H), 5.77 (br s, 1H), 6.06 (s, 1H), 7.44 (m, 2H), 7.56 (m, 1H), 8.01 (m, 2H); MS (FD) m/z 454 (M)$^+$.

Example A39

(4aR,5R,6R,7R)-6-(2-Furancarbonyl)oxy-7-methoxy-4a,5,6,7-tetrahydro-3,4a,5-trimethylnaphtho[2,3-b]furan-2(4H)-one The title compound (7.9 mg, 59%) was prepared in the same manner as in Example A10, except that a 7α-methoxy derivative of substance PF1092C (10 mg, 0.04 mmol), 4-dimethylaminopyridine (24 mg, 0.19 mmol), and 2-furoyl chloride (16 µl, 0.16 mmol) were stirred at 25° C. for 6 hr and the purification was performed by preparative TLC (toluene:ethyl acetate=4:1).

$^1$H NMR (CDCl$_3$) δ 1.18 (d, J=7.2 Hz, 3H), 1.25 (s, 3H), 1.95 (d, J=2.0 Hz, 3H), 2.20 (dq, J=7.2, 2.7 Hz, 1H), 2.28 (br d, J=16.3 Hz, 1H), 2.90 (d, J=16.3 Hz, 1H), 3.57 (s, 3H), 3.75 (dd, J=4.8, 1.4 Hz, 1H), 5.32 (ddd, J=2.7, 1.4, 1.4 Hz, 1H), 5.87 (br d, J=4.8 Hz, 1H), 6.03 (s, 1H), 6.52 (dd, J=3.5, 1.8 Hz, 1H), 7.14 (dd, J=3.5, 0.8 Hz, 1H), 7.60 (dd, J=1.8, 0.8 Hz, 1H); MS (ESI) m/z 371 (M+H)$^+$.

Example A40

(4aR,5R,6R,7R)-7-Ethoxy-6-(2-furancarbonyl)oxy-4a,5,6,7-tetrahydro-3,4a, 5-trimethylnaphtho[2,3-b]furan-2(4H)-one The procedure of Example A10 (1) was repeated, except that substance PF1092C (26 mg, 0.10 mmol), diisopropylethylamine (31 µl, 0.18 mmol), and methanesulfonyl chloride (10 µl, 0.13 mmol) were stirred at −15° C. for 30 min, ethanol (29 µl, 0.49 mmol) was added thereto, the temperature was raised to 25° C., and the mixture was stirred at that temperature for 45 min, and the purification was performed by column chromatography on silica gel (hexane:ethyl acetate=1:1). Thus, a corresponding 7a-ethoxy derivative (12 mg, 41%) was prepared.

The procedure of Example A10 (2) was repeated, except that the compound prepared just above (10 mg, 0.03 mmol), 4-dimethylaminopyridine (30 mg, 0.25 mmol), and 2-furoyl chloride (20 µl, 0.20 mmol) were stirred at 25° C. for 4 hr and the purification was performed by preparative TLC (toluene:ethyl acetate=4:1). Thus, the title compound (10 mg, 78%) was prepared.

$^1$H NMR (CDCl$_3$) δ 1.18 (d, J=7.1 Hz, 3H), 1.25 (t, J=7.0 Hz, 3H), 1.25 (s, 3H), 1.95 (d, J=1.7 Hz, 3H), 2.23 (dq, J=2.6, 7.1 Hz, 1H), 2.30 (br d, J=16.1 Hz, 1H), 2.89 (d, J=16.1 Hz, 1H), 3.69 (dq, J=9.5, 7.0 Hz, 1H), 3.84 (dd, J=4.9, 1.2 Hz, 1H), 3.92 (dq, J=9.5, 7.0 Hz, 1H), 5.30 (m, 1H), 5.85 (br d, J=4.9 Hz, 1H), 6.02 (s, 1H), 6.52 (dd, J=3.6, 1.7 Hz, 1H), 7.13 (br d, J=3.6 Hz, 1H), 7.60 (m, 1H); MS (ESI) m/z 385 (M+H)$^+$.

Example A41

(4aR,5R,6R,7R)-7-Ethoxy-6-(2-thiophencarbonyl)oxy-4a,5,6,7-tetrahydro-3,4a,5-trimethylnaphtho[2,3-b]furan-2(4H)-one The title compound (14 mg, 86%) was prepared in the same manner as in Example A40, except that a 7α-ethoxy derivative of substance PF1092C (12 mg, 0.04 mmol), 4-dimethylaminopyridine (35 mg, 0.28 mmol), and 2-thenoyl chloride (26 µl, 0.24 mmol) were stirred at 25° C. for 2 hr and the purification was performed by preparative TLC (toluene:ethyl acetate=4:1).

$^1$H NMR (CDCl$_3$) δ 1.20 (d, J=7.1 Hz, 3H), 1.26 (t, J=7.0 Hz, 3H), 1.28 (s, 3H), 1.95 (d, J=1.9 Hz, 3H), 2.23 (dq, J=7.0, 2.7 Hz, 1H), 2.31 (br d, J=16.2 Hz, 1H), 2.90 (d, J=16.2 Hz, 1H), 3.70 (dq, J=9.4, 7.0 Hz, 1H), 3.88 (dd, J=4.7, 1.3 Hz, 1H), 3.94 (dq, J=9.4, 7.0 Hz, 1H), 5.28 (ddd, J=2.7, 1.3, 1.3 Hz, 1H), 5.86 (br d, J=4.7 Hz, 1H), 6.03 (s, 1H), 7.13 (dd, J=5.0, 3.8 Hz, 1H), 7.58 (dd, J=5.0, 1.3 Hz, 1H), 7.79 (dd, J=3.8, 1.3 Hz, 1H); MS (ESI) m/z 401 (M+H)$^+$.

Example A42

(4aR,5R,6R,7R)-6,7-Dimethoxy-4a,5,6,7-tetrahydro-3,4a,5-trimethylnaphtho[2,3-b]furan-2(4H)-one The title compound (3.9 mg, 11%) was prepared in the same manner as in Example A29, except that a 7α-methoxy derivative of substance PF1092C (35 mg, 0.13 mmol), 60% sodium hydride (14 mg, 0.34 mmol) and methyl iodide (159 pl, 2.55 mmol) were stirred at −30° C. for 2 hr and the purification was performed by preparative TLC (hexane ethyl acetate=2:1).

$^1$H NMR (CDCl$_3$) δ 1.10 (s, 3H), 1.19 (d, J=7.1 Hz, 3H), 1.92 (d, J=1.9 Hz, 3H), 1.92 (dq, J=7.1, 3.0 Hz, 1H), 2.20 (br d, J=16.4 Hz, 1H), 2.84 (d, J=16.4 Hz, 1H), 3.31 (ddd, J=3.0, 1.5, 1.5 Hz, 1H), 3.42 (s, 3H), 3.46 (s, 3H), 3.75 (dd, J=5.0, 1.5 Hz, 1H), 5.90 (br d, J=5.0 Hz, 1H), 5.99 (s, 1H); MS (FAB) m/z 291 (M+H)$^+$.

Example A43

(4aR,5R,6R,7R)-7-Methoxy-6-methylsulfonyloxy-4a,5,6,7-tetrahydro-3,4a,5-trimethylnaphtho[2,3-b]furan-2(4H)-one The title compound (22 mg, 82%) was prepared in the same manner as in Example A10, except that a 7α-methoxy derivative of substance PF1092C (21 mg, 0.07 mmol), 4-dimethylaminopyridine (15 mg, 0.12 mmol), methanesulfonyl chloride (25 μl, 0.32 mmol) and triethylamine (48 μl, 0.34 mmol) were stirred at 25° C. for 2 days and the purification was performed by preparative TLC (hexane:ethyl acetate=1:1).

$^1$H NMR (CDCl$_3$) δ 1.09 (br s, 3H), 1.24 (d, J=7.1 Hz, 3H), 1.93 (d, J=1.8 Hz, 3H), 2.15 (dq, J=7.1, 2.6 Hz, 1H), 2.24 (br d, J=16.3 Hz, 1H), 2.86 (d, J=16.3 Hz, 1H), 3.07 (s, 3H), 3.50 (s, 3H), 3.98 (dd, J=4.8, 1.7 Hz, 1H), 4.86 (m, 1H), 5.86 (br d, J=4.8 Hz, 1H), 6.00 (s, 1H); MS (ESI) m/z 355 (M+H)$^+$.

Example A44

(4aR,5R,6R,7R)-7-Acetoxy-6-(2-furancarbonyl)oxy-4a,5,6,7-tetrahydro-3,4a,5-trimethylnaphtho[2,3-b]furan-2(4H)-one The procedure of Example A10 (1) was repeated, except that substance PF1092C (21 mg, 0.08 mmol), diisopropylethylamine (17 μl, 0.10 mmol), and methanesulfonyl chloride (8 μl, 0.10 mmol) were stirred at −15° C. for 10 min, potassium acetate (16 mg, 0.16 mmol) and an anhydrous acetonitrile solution (52 μl) containing 18-crown-6 (1.1 mg, catalytic amount) were then added thereto, the mixture was stirred at 25° C. for 5 hr, and the purification was performed by preparative TLC (methylene chloride:methanol=30:1). Thus, a corresponding 7α-acetoxy derivative (11 mg, 44%) was prepared.

The procedure of Example A10 (2) was repeated, except that the above compound (11 mg, 0.04 mmol), 4-dimethylaminopyridine (21 mg, 0.17 mmol), and 2-furoyl chloride (14 μl, 0.14 mmol) were stirred at 25° C. for 4 hr and the purification was performed by preparative TLC (hexane:ethyl acetate=3:2). Thus, the title compound (9.7 mg, 67%) was prepared.

$^1$H NMR (CDCl$_3$) δ 1.18 (d, J=7.1 Hz, 3H), 1.25 (s, 3H), 1.96 (d, J=1.8 Hz, 3H), 2.09 (s, 3H), 2.21 (dq, J=7.1, 2.8 Hz, 1H), 2.32 (br d, J=16.3 Hz, 1H), 2.92 (d, J=16.3 Hz, 1H), 5.27 (dd, J=4.8, 1.5 Hz, 1H), 5.31 (m, 1H), 5.88 (br d, J=4.8 Hz, 1H), 6.03 (s, 1H), 6.52 (dd, J=3.5, 1.7 Hz, 1H), 7.15 (br d, J=3.5 Hz, 1H), 7.60 (m, 1H); MS (FAB) m/z 399 (M+H)$^+$.

Example A45

(4aR,5R,6R,7R)-7-Hydroxy-6-(2-thiophencarbonyl)oxy-4a,5,6,7-tetrahydro-3, 4a, 5-trimethylnaphtho[2,3-b]furan-2(4H)-one The procedure of Example A10 was repeated, except that substance PF1092C (50 mg, 0.19 mmol), diisopropylethylamine (43 μl, 0.25 mmol), and methanesulfonyl chloride (18 μl, 0.23 mmol) were stirred at −15° C. for 10 min, silica gel (250 mg) was then added thereto, the mixture was stirred at 25° C. for one hr, and the purification was performed by column chromatography on silica gel (hexane:ethyl acetate=1:2). Thus, a corresponding 7α-hydroxy derivative (18 mg, 36%) was prepared.

The procedure of Example A3 (1) was repeated, except that the above compound (18 mg, 0.07 mmol), imidazole (12 mg, 0.08 mmol), and t-butyldimethylsilyl chloride (12 mg, 0.08 mmol) were stirred at 25° C. for one hr and the purification was performed by preparative TLC (toluene ethyl acetate=5:1). Thus, a corresponding 7α-(t-butyldimethylsilyl)oxy derivative (23 mg, 88%) was prepared.

Subsequently, the procedure of Example A3 (2) was repeated, except that the compound (23 mg, 0.06 mmol) prepared just above, 4-dimethylaminopyridine (34 mg, 0.28 mmol), and 2-thenoyl chloride (29 μl, 0.27 mmol) were stirred at 25° C. for 18 hr and the purification was performed by column chromatography on silica gel (hexane ethyl acetate=5:1). Thus, a corresponding 7α-(t-butyldimethylsilyl)oxy-3β-(2-thenoyl)oxide derivative (19 mg, 64%) was prepared.

Further, the procedure of Example A3 (3) was repeated, except that the compound (19 mg, 0.04 mmol) prepared just above and a 1.0 M solution of tetrabutylammonium fluoride in THF (46 μl, 0.05 mmol) were stirred under ice cooling for one hr and the purification was performed by preparative TLC (hexane:ethyl acetate=1:2). Thus, the title compound (6.1 mg, 42%) was prepared.

$^1$H NMR (CDCl$_3$) δ 1.21 (d, J=7.2 Hz, 3H), 1.27 (br s, 3H), 1.96 (d, J=1.7 Hz, 3H), 2.28 (dq, J=7.2, 3.0 Hz, 1H), 2.31 (br d, J=16.5 Hz, 1H), 2.92 (d, J=16.5 Hz, 1H), 4.33 (m, 1H), 5.15 (ddd, J=3.0, 1.5, 1.5 Hz, 1H), 5.88 (br d, J=4.9 Hz, 1H), 6.04 (s, 1H), 7.13 (dd, J=5.0, 3.8 Hz, 1H), 7.59 (dd, J=5.0, 1.2 Hz, 1H), 7.80 (dd, J=3.8, 1.2 Hz, 1H); MS (EI) m/z 372 (M)$^+$.

Example A46

(4aR,5R,6R,7R)-6-Acetylamino-7-methoxy-4a,5,6,7-tetrahydro-3,4a,5-trimethylnaphtho[2,3-b]furan-2(4H)-one The title compound (3.0 mg, 20%) was prepared in the same manner as in Example A11, except that a 2′-methyloxazoline derivative of substance PF1092C (14 mg, 0.05 mmol) and methanesulfonic acid (20 μl, 0.01 mmol) were stirred in methanol at 25° C. for 3.5 hr and the purification was performed by preparative TLC (methylene chloride methanol=20:1).

$^1$H NMR (CDCl$_3$) δ 1.09 (d, J=0.9 Hz, 3H), 1.13 (d, J=7.2 Hz, 3H), 1.93 (d, J=1.9 Hz, 3H), 2.02 (s, 3H), 2.20 (dq, J=7.2, 3.7 Hz, 1H), 2.26 (br d, J=15.9 Hz, 1H), 2.87 (d, J=15.9 Hz, 1H), 3.49 (s, 3H), 3.60 (dd, J=5.1, 1.8 Hz, 1H), 4.37 (m, 1H), 5.39 (br d, J=8.2 Hz, 1H), 5.88 (br d, J=5.1 Hz, 1H), 6.01 (s, 1H); MS (ESI) m/z 318 (M+H)$^+$.

Reference Example 1

Synthesis of compound (7) (Liebigs Ann. Chem., 186, 1982 and Chem. Pharm. Bull., 28, 3265, 1980)

Compound (3) (4.42 g, 17.5 mmol) was dissolved in ethylene glycol dimethyl ether (17 ml) under an argon gas stream, a 2 M solution of methyllithium in THF (20 ml, 40 mmol) was added at 25° C. to the solution, and the mixture was stirred for 2 hr. The reaction solution was cooled to −78° C., a solution of compound (2) (in the structural formula, $R^5$=H) (3.2 g) in ethylene glycol dimethyl ether (15 ml) was added to the cooled reaction mixture, followed by stirring for 2 hr. Thereafter, the temperature of the reaction solution was raised to 25° C., a 0.3 M solution of sodium methoxide in methanol (60 ml, 18 mmol) was added thereto, and the mixture was stirred at that temperature for 30 min. Water was added to the reaction solution, followed by extraction with ethyl acetate. The organic layer was washed with saturated saline and then dried over magnesium sulfate, and the solvent was removed by distillation under reduced pressure. The residue was purified by column chromatography on silica gel (hexane:ethyl acetate=4:1) to give compound (4) (in the structural formula, $R^5$=H) (2.5 g, 65%).

A solution of the above compound (4) (500 mg, 2.1 mmol) dissolved in THF (10 ml) was added to a mixed solution composed of a 2 M solution of lithium diisopropylamide in THF (1.2 ml, 2.4 mmol) and THF (3.0 ml) at −78° C. under an argon gas stream, and the mixture was stirred for one hr. Subsequently, a saturated solution of zinc chloride in THF (3 ml) and methyl pyruvate (650 mg, 12.7 mmol) were added thereto, and the mixture was stirred at room temperature for 30 min. A saturated aqueous ammonium chloride solution was added to the reaction solution, followed by extraction with ethyl acetate. The organic layer was washed with saturated saline and dried over magnesium sulfate, and the solvent was removed by distillation under reduced pressure. The residue was purified by column chromatography on silica gel (hexane ethyl acetate=1:1) to give compound (6) (in the structural formula, $R^3$=H, $R^4$=$CH_3$, $R^5$=H, and $R^6$=$CH_3$) (670 mg, 94%).

The compound (6) (600 mg, 1.7 mmol) prepared just above was dissolved in benzene (50 ml), p-toluenesulfonic acid (220 mg, 0.9 mmol) was added to the solution, and the mixture was heated under reflux for 1.5 hr. The reaction solution was cooled, and a saturated aqueous sodium bicarbonate solution was added thereto, followed by extraction with methylene chloride. The organic layer was washed with saturated saline and dried over magnesium sulfate, and the solvent was removed by distillation under reduced pressure. The residue was purified by column chromatography on silica gel (hexane:ethyl acetate=4:1) to give compound (7) (in the structural formula, $R^3$=H, $R^4$=$CH_3$, and $R^5$=H) (174 mg, 42%).

Example B1

(1) Method A (4aR*,5R*,6S*)-6-Hydroxy-4a,5,6,7-tetrahydro-3, 4a,5-trimethylnaphtho[2,3-b]furan-2(4H)-one Compound (7) (in the structural formula, $R^3$=H, $R^4$=$CH_3$, and $R^5$=H) (100 mg, 0.4 mmol) was dissolved in methanol (25 ml), sodium borohydride (7 mg, 0.18 mmol) was added at 25° C., and the mixture was stirred for 10 min. A saturated aqueous ammonium chloride solution was added to the reaction solution, followed by extraction with methylene chloride. The organic layer was washed with saturated saline and dried over magnesium sulfate, and the solvent was removed by distillation under reduced pressure. The residue was purified by column chromatography on silica gel (hexane:ethyl acetate=2:1) to give the title compound (63 mg, 60%).

$^1$H NMR (CDCl$_3$) δ 1.16 (d, J=0.9 Hz, 3H), 1.19 (d, J=7.2 Hz, 3H), 1.74 (dq, J=7.2, 2.5 Hz, 1H), 1.89 (d, J=1.4 Hz, 3H), 2.18 (d, J=16.3 Hz, 1H), 2.40 (dd, J=20.0, 4.7 Hz, 1H), 2.57 (br ddd, J=20.0, 3.6 Hz, 1H), 2.82 (d, J=16.3 Hz, 1H), 4.02 (m, 1H), 5.74 (m, 1H), 5.97 (s, 1H); MS (EI) m/z 246 (M)$^+$.

(2) Method B (4aR,5R,6S)-6-Hydroxy-4a,5,6,7-tetrahydro-3,4a,5-trimethylnaphtho[2,3-b]furan-2(4H)-one Substance PF1092C (500 mg, 1.90 mmol) was dissolved in benzene (50 ml), p-toluenesulfonic acid (250 mg, 1.32 mmol) was added to the solution, and the mixture was stirred at 50° C. for 30 min. A saturated aqueous sodium bicarbonate solution was added to the reaction solution, followed by extraction with methylene chloride. The organic layer was washed with saturated saline and dried over magnesium sulfate, and the solvent was removed by distillation under reduced pressure. The residue was purified by column chromatography on silica gel (hexane:ethyl acetate=1:1) to give compound (7) (in the structural formula, $R^3$=H, $R^4$=$CH_3$, and $R^5$=H) (260 mg, 56%).

The compound (7) (in the structural formula, $R^3$=H, $R^4$=$CH_3$, and $R^5$=H) was dissolved in methanol (15 ml), sodium borohydride (80.5 mg, 2.17 mmol) was added, and the mixture was stirred for 10 min. A saturated aqueous ammonium chloride solution was added to the reaction solution, followed by extraction with methylene chloride. The organic layer was washed with saturated saline and dried over magnesium sulfate, and the solvent was removed by distillation under reduced pressure. The residue was purified by column chromatography on silica gel (hexane:ethyl acetate=1:1) to give the title compound (160 mg, 61%).

Example B2

(4aR*,5R*,6S*)-6-Acetoxy-4a,5,6,7-tetrahydro-3,4a, 5-trimethylnaphtho[2,3-b]furan-2(4H)-one The compound prepared in Example B1 (in the general formula (II), $R^3$=H, $R^4$=$CH_3$, and $R^5$=H) (50 mg, 0.20 mmol) was dissolved in pyridine (5 ml), acetyl chloride (80 mg, 0.70 mmol) was added thereto, and the mixture was stirred at 25° C. for one hr. A 15% aqueous potassium hydrogensulfate solution was added to the reaction solution, followed by extraction with methylene chloride. The organic layer was washed with saturated saline and dried over magnesium sulfate, and the solvent was removed by distillation under reduced pressure. The residue was purified by column chromatography on silica gel (hexane:ethyl acetate= 3:1) to give the title compound (55 mg, 80%).

$^1$H NMR (CDCl$_3$) δ 1.08 (d, J=7.2 Hz, 3H), 1.14 (d, J=0.9 Hz, 3H), 1.89 (dq, J=7.2, 2.5 Hz, 1H), 1.90 (d, J=1.4 Hz, 3H), 2.04 (s, 3H), 2.19 (d, J=16.3 Hz, 1H), 2.38 (dd, J=20.0, 4.7 Hz, 1H), 2.58 (br ddd, J=20.0, 3.6 Hz, 1H), 2.84 (d, J=16.3 Hz, 1H), 5.12 (m, 1H), 5.70 (m, 1H), 5.96 (s, 1H); MS (EI) m/z 288 (M)$^+$.

Example B3

(1) Method A (4aR*,5R*,6S*)-6-Propionyloxy-4a,5,6,7-tetrahydro-3,4a,5-trimethylnaphtho[2,3-b]furan-2 (4H)-one The title compound was prepared in the same manner as in Example B2, except that the compound prepared in Example B1 was reacted with propionyl chloride.

$^1$H NMR (CDCl$_3$) δ 1.08 (d, J=7.2 Hz, 3H), 1.13 (t, J=7.5 Hz, 3H), 1.14 (s, 3H), 1.90 (dq, J=7.2, 2.5 Hz, 1H), 1.91 (d,

J=1.4 Hz, 3H), 2.21 (d, J=16.3 Hz, 1H), 2.33 (q, J=7.5 Hz, 2H), 2.38 (dd, J=20.0, 4.7 Hz, 1H), 2.59 (br ddd, J=20.0, 3.6 Hz, 1H), 2.84 (d, J=16.3 Hz, 1H), 5.14 (m, 1H), 5.70 (m, 1H), 5.97 (s, 1H); MS (EI) m/z 302(M)$^+$.

(2) Method B (4aR,5R,6S)-6-Propionyloxy-4a,5,6,7-tetrahydro-3, 4a,5-trimethylnaphtho[2,3-b]furan-2(4H)-one The title compound was prepared in the same manner as in Example B2, except that the compound prepared in Example B1 (2) Method B was reacted with propionyl chloride.

Example B4

(4aR*,5R*,6S*)-6-Butyryloxy-4a,5,6,7-tetrahydro-3, 4a,5-trimethylnaphtho[2,3-b]furan-2(4H)-one The title compound was prepared in the same manner as in Example B2, except that the compound prepared in Example B1 was reacted with butyryl chloride.

$^1$H NMR (CDCl$_3$) 60.93 (t, J=7.2 Hz, 3H), 1.08 (d, J=7.2 Hz, 3H), 1.14 (d, J=0.9 Hz, 3H), 1.64 (seq, J=7.2 Hz, 2H), 1.90 (dq, J=7.2, 2.5 Hz, 1H), 1.90 (d, J=1.4 Hz, 3H), 2.21 (d, J=16.3 Hz, 1H), 2.28 (t, J=7.2 Hz, 2H), 2.37 (dd, J=20.0, 4.7 Hz, 1H), 2.59 (br ddd, J=20.0, 3.6 Hz, 1H), 2.84 (d, J=16.3 Hz, 1H), 5.14 (m, 1H), 5.70 (br t, 1H), 5.97 (s, 1H); MS (EI) m/z 316(M)$^+$.

Example B5

(4aR*,5R*,6S*)-6-(2-Methyl)propionyloxy-4a, 5,6, 7-tetrahydro-3,4a,5-trimethylnaphtho[2,3-b]furan-2 (4H)-one The title compound was prepared in the same manner as in Example B2, except that the compound prepared in Example B1 was reacted with isobutyryl chloride.

$^1$H NMR (CDCl$_3$) δ 1.08 (d, J=7.1 Hz, 3H), 1.14 (d, J=7.2 Hz, 3H), 1.15 (d, J=0.9 Hz, 3H), 1.16 (d, J=7.1 Hz, 3H), 1.90 (d, J=1.4 Hz, 3H), 1.90 (dq, J=7.2, 2.5 Hz, 1H), 2.21 (d, J=16.3 Hz, 1H), 2.34 (dd, J=20.0, 4.7 Hz, 1H), 2.53 (sep, J=7.1 Hz, 1H), 2.59 (br dd, J=20.0, 3.6 Hz, 1H), 2.84 (d, J=16.3 Hz, 1H), 5.12 (m, 1H), 5.70 (br t, 1H), 5.97 (s, 1H); MS (EI) m/z 316(M)$^+$.

Example B6

(4aR*,5R*,6S*)-6-(3-Methyl)butyryloxy-4a,5,6,7-tetrahydro-3,4a,5-trimethylnaphtho[2,3-b]furan-2 (4H)-one The title compound was prepared in the same manner as in Example B2, except that the compound prepared in Example B1 was reacted with isovaleryl chloride.

$^1$H NMR (CDCl$_3$) δ 0.93 (d, J=6.5 Hz, 6H), 1.08 (d, J=7.2 Hz, 3H), 1.14 (s, 3H), 1.90 (d, J=1.4 Hz, 3H), 1.90 (dq, J=7.2, 2.5 Hz, 1H), 2.09 (m, 1H), 2.18 (d, J=6.5 Hz, 2H), 2.21 (d, J=16.3 Hz, 1H), 2.37 (dd, J=20.0, 4.7 Hz, 1H), 2.59 (br ddd, J=20.0, 3.6 Hz, 1H), 2.84 (d, J=16.3 Hz, 1H), 5.13 (m, 1H), 5.70 (br t, 1H), 5.97 (s, 1H); MS (EI) m/z 330 (M)$^+$.

Example B7

(4aR*,5R*,6S*)-6-Benzoyloxy-4a,5,6,7-tetrahydro-3,4a,5-trimethylnaphtho[2,3-b]furan-2(4H)-one The title compound was prepared in the same manner as in Example B2, except that the compound prepared in Example B1 was reacted with benzoyl chloride.

$^1$H NMR (CDCl$_3$) δ 1.17 (d, J=7.2 Hz, 3H), 1.30 (s, 3H), 1.92 (d, J=1.4 Hz, 3H), 2.03 (dq, J=7.2, 2.5 Hz, 1H), 2.27 (d, J=16.3 Hz, 1H), 2.54 (dd, J=20.0, 4.7 Hz, 1H), 2.73 (br ddd, J=20.0, 3.6 Hz, 1H), 2.89 (d, J=16.3 Hz, 1H), 5.41 (m, 1H), 5.75 (br t, 1H), 6.00 (s, 1H), 7.40–8.11 (m, 5H); MS (EI) m/z 350(M)$^+$.

Example B8

(1) Method A (4aR*,5R*,6S*)-6-(2-Furoyl)oxy-4a,5,6,7-tetrahydro-3,4a,5-trimethylnaphtho[2,3-b]furan-2 (4H)-one The title compound was prepared in the same manner as in Example B2, except that the compound prepared in Example B1 was reacted with 2-furoyl chloride.

$^1$H NMR (CDCl$_3$) δ 1.16 (d, J=7.2 Hz, 3H), 1.27 (s, 3H), 1.93 (d, J=1.7 Hz, 3H), 2.00 (dq, J=7.2, 2.5 Hz, 1H), 2.26 (d, J=16.4, 1H), 2.54 (br dd, J=20.8, 5.0 Hz, 1H), 2.69 (br ddd, 1H), 2.88 (d, J=16.4 Hz, 1H), 5.38 (br t, 1H), 5.74 (br t, 1H), 5.96 (s, 1H), 6.50 (dd, J=3.3, 1.7 Hz, 1H), 7.11 (dd, J=3.3, 0.8 Hz, 1H), 7.57 (dd, J=1.7, 0.8 Hz, 1H); MS(EI) m/z 340 (M)$^+$.

(2) Method B (4aR,5R,6S)-6-(2-Furoyl)oxy-4a,5,6,7-tetrahydro-3, 4a,5-trimethylnaphtho[2,3-b]furan-2(4H)-one The title compound was prepared in the same manner as in Example B2, except that the compound prepared in Example B1 (2) Method B was reacted with 2-furoyl chloride.

Example B9

(4aR*,5R*,6S*)-4a,5,6,7-Tetrahydro-6-(2-thenoyl) oxy-3,4a,5-trimethylnaphtho[2,3-b]furan-2(4H)-one The title compound was prepared in the same manner as in Example B2, except that the compound prepared in Example B1 was reacted with 2-thenoyl chloride.

$^1$H NMR (CDCl$_3$) δ 1.16 (d, J=7.2 Hz, 3H), 1.27 (s, 3H), 1.92 (d, J=1.4 Hz, 3H), 2.03 (dq, J=7.2, 2.5 Hz, 1H), 2.25 (d, J=16.3 Hz, 1H), 2.54 (dd, J=20.0, 4.7 Hz, 1H), 2.69 (br ddd, J=20.0, 3.6 Hz, 1H), 2.87 (d, J=16.3 Hz, 1H), 5.33 (m, 1H), 5.73 (br t, 1H), 5.99 (s, 1H), 7.09 (dd, J=5.0, 3.7 Hz, 1H), 7.54 (dd, J=1.3, 5.0 Hz, 1H), 7.76 (dd, J=3.7, 1.3 Hz, 1H); MS (FAB) m/z 357(M+H)$^+$.

Example B10

(6'R*,7'R*)-Spiro[1,3-dioxolane-2,8'-(2',6',7'-trimethylbicyclo[4,4,0]deca-1'-en-3'-one)]

Compound (3) (400 mg, 1.6 mmol) was dissolved in ethylene glycol dimethyl ether (10 ml) under an argon gas stream, a 1 M solution of methyllithium in diethyl ether (2 ml, 2 mmol) was added to the solution, and the mixture was stirred at 25° C. for 2 hr. The reaction mixture was cooled to −78° C., a solution of compound (2) (in the structural formula, R$^5$=CH$_3$) (250 mg, 1.6 mmol) in ethylene glycol dimethyl ether (5 ml) was added to the cooled reaction mixture, followed by stirring for 2 hr. Thereafter, the temperature of the reaction solution was raised to 25° C., a 0.3 M solution of sodium methoxide in methanol (6 ml, 2 mmol) was added thereto, and the mixture was stirred at room temperature for 30 min. Water (20 ml) was added to the reaction solution, followed by extraction with ethyl acetate.

The organic layer was washed with saturated saline and then dried over magnesium sulfate, and the solvent was removed by distillation under reduced pressure. The residue was purified by column chromatography on silica gel (hexane:ethyl acetate=5:1) to give the title compound (230 mg, 59%).

$^1$H NMR (CDCl$_3$) δ 0.92 (d, J=6.9 Hz, 3H), 1.22 (s, 3H), 1.50 (ddd, J=17.4, 14.5, 4.1 Hz, 1H), 1.68 (br ddd, J=19.1, 13.9, 5.1 Hz, 1H), 1.75 (q, J=6.9 Hz, 1H), 1.80 (br s, 3H), 1.95–2.06 (m, 2H), 2.30–2.50 (m, 3H), 2.71 (dd, J=14.5, 3.7 Hz, 1H), 3.84–4.09 (m, 4H); MS (ESI) m/z 2 51(M+H)$^+$.

Example B11

(4'S*,6'R*,7'R*)-Spiro[1,3-dioxolane-2,8'-[4'-(1"-hydroxy-1"-methoxycarbonyl)ethyl-2',6',7'-trimethylbicyclo[4,4,0]deca-1'-en-3'-one]]

A 2 M solution of lithium diisopropylamide in THF (0.5 ml, 1.0 mmol) was added to anhydrous THF (1 ml) at −78° C. under an argon gas stream, a THF solution (2 ml) containing the compound prepared in Example B10 (200 mg, 0.8 mmol) was added thereto, and the mixture was stirred for one hr. Subsequently, a saturated solution of zinc chloride in THF (1 ml) and an anhydrous THF solution (2 ml) containing methyl pyruvate (105 mg, 1.0 mmol) were successively added, and the mixture was stirred at −78° C. for one hr. The temperature of the reaction solution was raised to −40° C., and the reaction solution was stirred for additional one hr. A saturated aqueous ammonium chloride solution was added thereto, followed by extraction with methylene chloride. The organic layer was washed with saturated saline and dried over magnesium sulfate, and the solvent was removed by distillation under reduced pressure. The residue was purified by column chromatography on silica gel (hexane:ethyl acetate=3:1) to give the title compound (6) (in the structural formula, R$^3$=H, R$^4$=CH$_3$, R$^5$=CH$_3$, and R$^6$=CH3) (166 mg, 59%).

$^1$H NMR (CDCl$_3$) δ 0.92–0.96 (d×2, J=6.9 Hz, 3H), 1.24–1.30 (s×2, 3H), 1.45 (s, 3H), 1.70–1.82 (m, 1H), 1.80 (s, 3H), 1.90–2.74 (m, 7H), 3.70–3.80 (s, 3H), 3.85–4.13 (m, 4H), 4.75 (br s, 1H); MS (ESI) m/z 353(M+H)$^+$.

Example B12

(4aR*,5R*)-4a,7-Dihydro-3,4a ,5,9-tetramethylnaphtho[2,3-b]furan-2,6 (4H,5H)-dione The compound prepared in Example B11 (520 mg, 4.7 mmol) was dissolved in benzene (30 ml), p-toluenesulfonic acid (150 mg, 2.4 mmol) was added to the solution, and the mixture was heated under reflux for 4 hr. The reaction mixture was cooled, and a saturated aqueous sodium bicarbonate solution was added thereto, followed by extraction with ethyl acetate. The organic layer was washed with saturated saline and dried over magnesium sulfate, and the solvent was removed by distillation under reduced pressure. The residue was purified by column chromatography on silica gel (hexane:ethyl acetate=4:1) to give the title compound (173 mg, 45%).

$^1$H NMR (CDCl$_3$) δ 0.89 (s, 3H), 1.16 (d, J=6.8 Hz, 3H), 1.93 (s, 3H), 2.04 (s, 3H), 2.52 (d, J=16.3 Hz, 1H), 2.78 (d, J=16.3 Hz, 1H), 2.84 (q, J=6.8 Hz, 1H), 3.03 (dd, J=23.3, 4.2 Hz, 1H), 3.20 (dd, J=23.3, 4.2 Hz, 1H), 5.96 (br dd, 1H); MS (ESI) m/z 259(M+H)$^+$.

Example B13

(4aR*,5R*,6S*)-6-Hydroxy-4a,5,6,7-tetrahydro-3,4a,5,9-tetramethylnaphtho[2,3-b]furan-2(4H)-one The compound prepared in Example B12 (170 mg, 0.7 mmol) was dissolved in methanol (5 ml), sodium borohydride (15 mg, 0.6 mmol) was added thereto, and the mixture was stirred at 25° C. for 30 min. A saturated aqueous ammonium chloride solution was added to the reaction solution, followed by extraction with ethyl acetate. The organic layer was washed with saturated saline and dried over magnesium sulfate, and the solvent was removed by distillation under reduced pressure. The residue was purified by column chromatography on silica gel (hexane:ethyl acetate=4:1) to give the title compound (87 mg, 51%).

$^1$H NMR (CDCl$_3$) δ 1.14 (s, 3H), 1.21 (d, J=7.2 Hz, 3H), 1.77 (dq, J=7.2, 2.5 Hz, 1H), 1.89 (s, 3H), 2.01 (s, 3H), 2.19 (d, J=16.1 Hz, 1H), 2.46 (br dd, J=19.7, 4.2 Hz, 1H), 2.60 (ddd, J=19.7, 5.0, 3.2 Hz, 1H), 2.81 (d, J=16.1 Hz, 1H), 4.02 (br s, 1H), 5.89 (br dd, 1H); MS (EI) m/z 260 (M)$^+$.

Example B14

(4aR*,5R*,6S*)-6-Acetoxy-4a,5,6,7-tetrahydro-3,4a,5,9-tetramethylnaphtho[2,3-b]furan-2(4H)-one The compound prepared in Example B13 (8.0 mg, 0.03 mmol) was dissolved in methylene chloride (1.0 ml), 4-dimethylaminopyridine (15.0 mg, 0.12 mmol) and acetyl chloride (10.0 mg, 0.15 mmol) were added thereto, and the mixture was stirred at 25° C. for 7 hr. Water was added to the reaction solution, followed by extraction with methylene chloride. The organic layer was washed with saturated saline and dried over magnesium sulfate, and the solvent was removed by distillation under reduced pressure. The residue was purified by preparative TLC (hexane:ethyl acetate=4:1) to give the title compound (5.7 mg, 50%).

$^1$H NMR (CDCl$_3$) δ 1.10 (d, J=7.2 Hz, 3H), 1.10 (d, J=0.8 Hz, 3H), 1.90 (dq, J=7.2, 2.5 Hz, 1H), 2.02 (s, 3H), 2.06 (s, 3H), 2.07 (s, 3H), 2.20 (d, J=16.7 Hz, 1H), 2.45 (br dd, J=20.6, 5.0 Hz, 1H), 2.60 (ddd, J=20.6, 5.0, 3.3 Hz, 1H), 2.83 (d, J=16.7 Hz, 1H), 5.13 (br d, J=5.7 Hz, 1H), 5.85 (br dd, 1H); MS (ESI) m/z 303(M+H)$^+$.

Example B15

(4aR*,5R*,6S*)-6-Propionyloxy-4a,5,6,7-tetrahydro-3,4a,5,9-tetramethylnaphtho[2,3-b]furan-2(4H)-one The title compound was prepared in the same manner as in Example B14, except that the compound prepared in Example B13 was reacted with propionyl chloride.

$^1$H NMR (CDCl$_3$) δ 1.10 (d, J=7.2 Hz, 3H), 1.11 (d, J=0.6 Hz, 3H), 1.15 (t, J=7.6 Hz, 3H), 1.90 (dq, J=7.2, 2.5 Hz, 1H), 1.90 (s, 3H), 2.01 (s, 3H), 2.21 (d, J=16.1 Hz, 1H), 2.34 (q, J=7.6 Hz, 2H), 2.44 (br dd, J=20.1, 5.1 Hz, 1H), 2.62 (ddd, J=20.1, 5.4, 3.1 Hz, 1H), 2.83 (d, J=16.1 Hz, 1H), 5.15 (br dd, 1H), 5.85 (br dd, 1H); MS (ESI) m/z 317(M+H)$^+$.

Example B16

(4aR*,5R*,6S*)-6-Benzoyloxy-4a,5,6,7-tetrahydro-3,4a,5,9-tetramethylnaphtho[2,3-b]furan-2(4H)-one The compound prepared in Example B13 (8.0 mg, 0.03 mmol) was dissolved in pyridine (1.0 ml), benzoyl chloride (25.0 mg, 0.18 mmol) was added thereto, and the mixture was stirred at 25° C. for 2.5 hr. A 15% aqueous potassium hydrogensulfate solution was added to the reaction solution, followed by extraction with ethyl acetate. The organic layer was washed with saturated saline and dried over magnesium sulfate, and the solvent was removed by distillation under reduced pressure. The residue was purified by preparative TLC (hexane:ethyl acetate=4:1) to give the title compound (5.7 mg, 50%).

¹H NMR (CDCl₃) δ 1.19 (d, J=7.2 Hz, 3H), 1.27 (d, J=0.8 Hz, 3H), 1.92 (s, 3H), 2.03 (s, 3H), 2.05 (dq, J=7.2, 2.5 Hz, 1H), 2.27 (d, J=16.3 Hz, 1H), 2.60 (br dd, J=20.5, 4.4 Hz, 1H), 2.75 (ddd, J=20.5, 5.5, 3.3 Hz, 1H), 2.88 (d, J=16.3 Hz, 1H), 5.41 (br t, 1H), 5.89 (br t, 1H), 7.43–8.13 (m, 5H); MS (ESI) m/z 365(M+H)⁺.

Example B17

(4aR*,5R*,6S*)-6-(2-Furoyl)oxy-4a,5,6,7-tetrahydro-3,4a,5,9-tetramethylnaphtho[2,3-b]furan-2(4H)-one The title compound was prepared in the same manner as in Example B16, except that the compound prepared in Example B13 was reacted with 2-furoyl chloride.

¹H NMR (CDCl₃) δ 1.17 (d, J=6.9 Hz, 3H), 1.23 (s, 3H), 1.92 (s, 3H), 2.01 (dq, J=7.2, 2.5 Hz, 1H), 2.03 (s, 3H), 2.25 (d, J=16.2 Hz, 1H), 2.59 (br dd, J=20.5, 3.7 Hz, 1H), 2.71 (ddd, J=20.5, 5.4, 3.3 Hz, 1H), 2.87 (d, J=16.2 Hz, 1H), 5.36 (br dd, 1H), 5.87 (br dd, 1H), 6.50 (br dd, J=3.5, 1.8 Hz, 1H), 7.12 (dd, J=3.5, 0.8 Hz, 1H), 7.58 (dd, J=1.5, 0.8 Hz, 1H); MS (ESI) m/z 355 (M+H)⁺.

Example B18

(4'S*,6'R*,7'R*)-Spiro[1,3-dioxolane-2,8'-[6',7'-dimethyl-4'-(1-hydroxy-1"-methoxycarbonyl)propylbicyclo[4,4,0]deca-1'-en-3'-one]]

A 2 M solution of lithium diisopropylamide in THF (1.9 ml, 3.8 mmol) was added to anhydrous THF (1 ml) at −78° C. under an argon gas stream, a THF solution (2 ml) containing the compound (4) (in the structural formula, R⁵=H) (420 mg, 1.7 mmol) was added thereto, and the mixture was stirred for one hr. Subsequently, a saturated solution of zinc chloride in THF (2.5 ml) and an anhydrous THF solution (2 ml) containing methyl 2-oxobutyrate (420 mg, 3.6 mmol) were successively added, and the mixture was stirred at −78° C. for one hr. The temperature of the reaction solution was raised to −40° C., and the reaction solution was stirred for additional one hr. A saturated aqueous ammonium chloride solution was added thereto, followed by extraction with methylene chloride. The organic layer was washed with saturated saline and dried over magnesium sulfate, and the solvent was removed by distillation under reduced pressure. The residue was purified by column chromatography on silica gel (hexane:ethyl acetate=3:1) to give the title compound (6) (in the structural formula, R³=H, R⁴=CH₃CH₂, R⁵=H, and R⁶=CH₃) (290 mg, 46%).

¹H NMR (CDCl₃) δ 0.95 (d, J=6.7 Hz, 3H), 0.96 (t, J=7.5 Hz, 3H), 1.27 (s, 3H), 1.81 (dq, J=7.4, 2.5 Hz, 1H), 1.83 (q, J=7.4 Hz, 2H), 1.90–2.74 (m, 7H), 3.73 (s, 3H), 3.80–4.09 (m, 4H), 4.62 (s, 1H), 5.73 (d, J=1.7 Hz, 1H); MS (SIMS) m/z 353(M+H)⁺.

Example B19

(4aR*,5R*)-4a,7-Dihydro-3-ethyl-4a,5-dimethylnaphtho[2,3-b]furan-2,6 (4H,5H)-dione The compound prepared in Example B18 (290 mg, 0.8 mmol) was dissolved in benzene (20 ml), p-toluenesulfonic acid (90 mg, 0.3 mmol) was added to the solution, and the mixture was heated under reflux for 2 hr. The reaction mixture was cooled, diluted with ethyl acetate (20 ml), washed with a saturated aqueous sodium bicarbonate solution and saturated saline in that order, and dried over magnesium sulfate, and the solvent was removed by distillation under reduced pressure. The residue was purified by column chromatography on silica gel (hexane:ethyl acetate=4:1) to give the title compound (163 mg, 77%).

¹H NMR (CDCl₃) δ 0.92 (s, 3H), 1.15 (t, J=7.7 Hz, 3H), 1.15 (d, J=7.6 Hz, 3H), 2.39 (m, 2H), 2.55 (d, J=16.4 Hz, 1H), 2.81 (q, J=7.6 Hz, 1H), 2.83 (d, J=16.4 Hz, 1H), 3.02 (dd, J=23.4, 3.9 Hz, 1H), 3.16 (dd, J=23.6, 4.1 Hz, 1H), 5.84 (m, 1H), 6.03 (s, 1H).

Example B20

(4aR*,5R*,6S*)-4a,5-Dimethyl-3-ethyl-6-hydroxy-4a,5,6,7-tetrahydronaphtho[2,3-b]furan-2(4H)-one The compound prepared in Example B19 (163 mg, 0.6 mmol) was dissolved in methanol (5.0 ml), sodium borohydride (6.0 mg, 0.19 mmol) was added thereto, and the mixture was stirred at 25° C. for 30 min. A saturated aqueous ammonium chloride solution was added to the reaction solution, followed by extraction with ethyl acetate. The organic layer was washed with saturated saline and dried over magnesium sulfate, and the solvent was removed by distillation under reduced pressure. The residue was purified by column chromatography on silica gel (hexane:ethyl acetate=4:1) to give the title compound (78 mg, 48%).

¹H NMR (CDCl₃) δ 1.13 (t, J=7.6 Hz, 3H), 1.18 (d, J=0.8 Hz, 3H), 1.20 (d, J=7.2 Hz, 3H), 1.75 (dq, J=7.2, 2.5 Hz, 1H), 2.21 (d, J=16.3 Hz, 1H), 2.34, 2.36 (each br dq, J=7.6 Hz, 2H), 2.40 (br dd, 1H), 2.59 (m, 1H), 2.86 (d, J=16.3 Hz, 1H), 4.03 (br s, 1H), 5.76 (br t, 1H), 5.99 (s, 1H); MS (ESI) m/z 261(M+H)⁺.

Example B21

(4aR*,5R*,6S*)-6-Acetoxy-4a,5-dimethyl-3-ethyl-4a,5,6,7-tetrahydronaphtho[2,3-b]furan-2(4H)-one The compound prepared in Example B20 (10.0 mg, 0.04 mmol) was dissolved in methylene chloride (1.0 ml), 4-dimethylaminopyridine (15.0 mg, 0.12 mmol) and acetyl chloride (12.0 mg, 0.20 mmol) were added thereto, and the mixture was stirred at 25° C. for 20 hr. Water was added to the reaction solution, followed by extraction with methylene chloride. The organic layer was washed with saturated saline and dried over magnesium sulfate, and the solvent was removed by distillation under reduced pressure. The residue was purified by preparative TLC (hexane:ethyl acetate=4:1) to give the title compound (9.1 mg, 78%).

¹H NMR (CDCl₃) δ 1.10 (d, J=7.2 Hz, 3H), 1.13 (t, J=7.6 Hz, 3H), 1.15 (s, 3H), 1.90 (dq, J=7.2, 2.5 Hz, 1H), 2.06 (s, 3H), 2.23 (d, J=16.1 Hz, 1H), 2.33–2.39 (m, 1H), 2.35, 2.37 (each br dq, J=7.6 Hz, 2H), 2.59 (ddd, J=20.5, 7.5, 3.1 Hz, 1H), 2.88 (d, J=16.1 Hz, 1H), 5.14 (m, 1H), 5.72 (br t, 1H), 5.98 (s, 1H); MS (ESI) m/z 303 (M+H)⁺.

Example B22

(4aR*,5R*,6S*)-4a,5-Dimethyl-3-ethyl-6-propionyloxy-4a,5,6,7-tetrahydronaphtho[2,3-b]furan-2(4H)-one The title compound was prepared in the same manner as in Example B21, except that the compound prepared in Example B20 was reacted with propionyl chloride.

¹H NMR (CDCl₃) δ 1.10 (d, J=7.2 Hz, 3H), 1.13 (t, J=7.7 Hz, 3H), 1.14 (t, J=7.7 Hz, 3H), 1.15 (s, 3H), 1.91 (dq, J=7.2, 2.6 Hz, 1H), 2.34 (d, J=16.2 Hz, 1H), 2.35–2.36 (m, 4H), 2.40 (br dd, 1H), 2.57–2.64 (m, 1H), 2.88 (d, J=16.2 Hz,

1H), 5.15–5.17 (m, 1H), 5.72 (br t, 1H), 5.99 (s, 1H); MS (ESI) m/z 317 (M+H)$^+$.

Example B23

(4aR*,5R*,6S*)-6-Benzoyloxy-4a,5-dimethyl-3-ethyl-4a,5,6,7-tetrahydronaphtho[2,3-b]furan-2(4H)-one The compound prepared in Example B20 (10.0 mg, 0.04 mmol) was dissolved in pyridine (1.0 ml), benzoyl chloride (16.0 mg, 0.12 mmol) was added thereto, and the mixture was stirred at 25° C. for 2 hr. A 15% aqueous potassium hydrogensulfate solution was added to the reaction solution, followed by extraction with ethyl acetate. The organic layer was washed with saturated saline and dried over magnesium sulfate, and the solvent was removed by distillation under reduced pressure. The residue was purified by preparative TLC (hexane:ethyl acetate=4:1) to give the title compound (4.7 mg, 34%).

$^1$H NMR (CDCl$_3$) δ 1.16 (t, J=7.8 Hz, 3H), 1.19 (d, J=7.5 Hz, 3H), 1.32 (s, 3H), 2.05 (dq, J=7.5, 2.5 Hz, 1H), 2.31 (d, J=16.1 Hz, 1H), 2.37, 2.39 (each br q, J=7.8 Hz, 2H), 2.56 (br dd, J=20.8, 5.3 Hz, 1H), 2.73 (br ddd, 1H), 2.94 (d, J=16.1 Hz, 1H), 5.43 (br t, 1H), 5.77 (br t , 1H), 6.02 (s, 1H), 7.43–8.06 (m, 5H); MS (ESI) m/z 365(M+H)$^+$.

Example B24

(4aR*,5R*,6S*)-4a,5-Dimethyl-3-ethyl-6-(2-furoyl)oxy-4a,5,6,7-tetrahydronaphtho[2,3-b]furan-2(4H)-one The title compound was prepared in the same manner as in Example B23, except that the compound prepared in Example B20 was reacted with 2-furoyl chloride.

$^1$H NMR (CDCl$_3$) δ 1.14 (t, J=7.5 Hz, 3H), 1.16 (d, J=7.2 Hz, 3H), 1.28 (s, 3H), 2.00 (dq, J=7.2, 2.5 Hz, 1H), 2.28 (d, J=16.1 Hz, 1H), 2.37, 2.38 (each br q, J=7.5 Hz, 2H), 2.54 (dd, J=21.0, 5.2 Hz, 1H), 2.69 (br dd, 1H), 2.92 (d, J=16.1 Hz, 1H), 5.38 (br s, 1H), 5.75 (t, J=3.9 Hz, 1H), 6.01 (s, 1H), 6.50 (dd, J=3.6, 0.8 Hz, 1H), 7.12 (d, J=3.6 Hz, 1H), 7.58 (t, J=0.8 Hz, 1H); MS (ESI) m/z 355 (M+H)$^+$.

Example B25

(4'S*,6'R*,7'R*)-Spiro[1,3-dioxolane-2,8'-[6',7 '-dimethyl-4'-(1"-hydroxy-1"-methoxycarbonyl)methylbicyclo[4,4,0]deca-1'-ene-3'-one]]

The compound (4) (in the structural formula, R$^5$=H) (800 mg, 3.4 mmol) was dissolved in ethanol (10 ml), a 1 N aqueous sodium hydroxide solution (30 ml, 3 mmol) was added to the solution, and a previously prepared 1.2 M aqueous glyoxalic acid solution (10 ml, 12 mmol) was added thereto, and the mixture was stirred at 50° C. for 3 hr. The reaction solution was diluted with water, washed with ethyl acetate, and the water layer was adjusted to pH 2.5 and then extracted with methylene chloride. On the other hand, the organic layer was dried over magnesium sulfate, and the solvent was removed by distillation under reduced pressure. The residue was dissolved in a mixed solution of benzene (12 ml) and methanol (4 ml), and a 2 M solution of trimethylsilyldiazomethane in hexane (2.5 ml, 5 mmol) was dropwise added thereto at 25° C. The solvent was then removed by distillation under reduced pressure to give the title compound (6) (in the structural formula, R$^3$=H, R$^4$=H, R$^5$=H, and R$^6$=CH$_3$).

$^1$H NMR (CDCl$_3$) δ 0.85–0.93 (d×2, J=6.9 Hz, 3H), 1.26–1.31 (s×2, 3H), 1.51–1.59 (dt×2, 1H), 1.74 (dd, J=13.0, 4.7 Hz, 1H), 1.79 (d, J=6.9 Hz, 1H), 1.93 (br t, 2H), 2.22–2.30 (m, 1H), 2.58–2.68 (m, 1H), 2.80–2.94 (m, 2H), 3.82 (s×2, 3H), 3.84–4.13 (m, 4H), 4.94–4.96 (m, 1H), 5.80–5.81 (s×2, 1H); MS (ESI) m/z 325(M+H)$^+$.

Example B26

(4aR*,5R*,6S*)-4a,5-Dimethyl-6-hydroxy-4a,5,6,7-tetrahydronaphtho[2,3-b]furan-2(4H)-one The compound prepared in Example B25 (450 mg) was dissolved in benzene (10 ml), p-toluenesulfonic acid (20 mg, 0.10 mmol) was added to the solution, and the mixture was stirred at 60° C. for one hr. The reaction mixture was cooled, and a saturated aqueous sodium bicarbonate solution was added thereto, followed by extraction with methylene chloride. The organic layer was washed with saturated saline and dried over magnesium sulfate, and the solvent was removed by distillation under reduced pressure. The residue was dissolved in methanol (6 ml), sodium borohydride (40 mg, 1.3 mmol) was added thereto, and the mixture was stirred at 25° C. for 10 min. A saturated aqueous ammonium chloride solution was added to the reaction solution, followed by extraction with methylene chloride. The organic layer was washed with saturated saline and dried over magnesium sulfate, and the solvent was removed by distillation under reduced pressure. The residue was purified by column chromatography on silica gel (hexane:ethyl acetate=1:1) to give the title compound (39.8 mg, 5%).

$^1$H NMR (CDCl$_3$) δ 1.19 (d, J=7.3 Hz, 3H), 1.21 (s, 3H), 1.75 (dq, J=7.3, 2.5 Hz, 1H), 2.34 (br d, J=16.4 Hz, 1H), 2.44 (br dd, J=20.8, 5.3 Hz, 1H), 2.60 (ddd, J=20.8, 7.3, 3.6 Hz, 1H), 2.94 (d, J=16.4 Hz, 1H), 4.04 (br s, 1H), 5.83 (br s×2, 2H), 6.09 (s, 1H); MS (ESI) m/z 233(M+H)$^+$.

Example B27

(4aR*,5R*,6S*)-6-Acetoxy-4a,5-dimethyl-4a,5,6,7-tetrahydronaphtho [2,3-b]furan-2(4H)-one The compound prepared in Example B26 (8.0 mg, 0.03 mmol) was dissolved in methylene chloride (1.0 ml), 4-dimethylaminopyridine (15.0 mg, 0.12 mmol) and acetyl chloride (10.0 mg, 0.15 mmol) were added thereto, and the mixture was stirred at 25° C. for 7 hr. Water was added to the reaction solution, followed by extraction with methylene chloride. The organic layer was washed with saturated saline and dried over magnesium sulfate, and the solvent was removed by distillation under reduced pressure. The residue was purified by preparative TLC (hexane:ethyl acetate=3:1) to give the title compound (1.97 mg, 21%).

$^1$H NMR (CDCl$_3$) δ 1.08 (d, J=7.2 Hz, 3H), 1.18 (d, J=0.8 Hz, 3H), 1.90 (dq, J=7.2, 2.5 Hz, 1H), 2.07 (s, 3H), 2.36 (d, J=16.5 Hz, 1H), 2.43 (br dd, J=20.9, 4.6 Hz, 1H), 2.60 (ddd, J=20.9, 8.99, 4.6 Hz, 1H), 2.96 (d, J=16.5 Hz, 1H), 5.14 (br t, 1H), 5.19 (br t, 1H), 5.86 (s, 1H), 6.08 (s, 1H); MS (ESI) m/z 275(M+H)$^+$.

Example B28

(4aR*,5R*,6S*)-4a,5-Dimethyl-6-propyloxy-4a,5,6,7-tetrahydronaphtho[2,3-b]furan-2(4H)-one The title compound was prepared in the same manner as in Example B27, except that the compound prepared in Example B26 was reacted with propionyl chloride.

$^1$H NMR (CDCl$_3$) δ 1.08 (d, J=7.2 Hz, 3H), 1.15 (t, J=7.5 Hz, 3H), 1.18 (s, 3H), 1.93 (dq, J=7.2, 2.5 Hz, 1H), 2.34 (q, J=7.5 Hz, 2H), 2.35–2.45 (m, 2H), 2.59–2.63 (m, 1H), 2.96

(d, J=16.6 Hz, 1H), 5.17 (br t, 1H), 5.79 (br t, 1H), 5.86 (s, 1H), 6.08 (s, 1H); MS (FAB) m/z 289(M+H)+.

Example B29

(4aR*,5R*,6S*)-6-Benzoyloxy-4a,5-dimethyl-4a,5, 6,7-tetrahydronaphtho[2,3-b]furan-2(4H)-one The compound prepared in Example B26 (8.0 mg, 0.03 mmol) was dissolved in pyridine (1.0 ml), benzoyl chloride (20.0 mg, 0.15 mmol) was added thereto, and the mixture was stirred at 25° C. for 2 hr. A 15% aqueous potassium hydrogensulfate solution was added to the reaction solution, followed by extraction with ethyl acetate. The organic layer was washed with saturated saline and dried over magnesium sulfate, and the solvent was removed by distillation under reduced pressure. The residue was purified by preparative TLC (hexane:ethyl acetate=3:1) to give the title compound (3.0 mg, 30%).

$^1$H NMR (CDCl$_3$) δ 1.16 (d, J=7.2 Hz, 3H), 1.34 (s, 3H), 2.05 (dq, J=7.2, 2.5 Hz, 1H), 2.43 (d, J=16.6 Hz, 1H), 2.57 (br dd, J=21.0, 4.7 Hz, 1H), 2.75 (ddd, J=21.0, 5.3, 3.2 Hz, 1H), 3.02 (d, J=16.6 Hz, 1H), 5.43 (br d, J=3.2 Hz, 1H), 5.83 (br t, 1H), 5.89 (s, 1H), 6.12 (s, 1H), 7.43–8.05 (m, 5H); MS (EIS) m/z 337(M+H)+.

Example B30

(4aR*,5R*,6S*)-4a,5-Dimethyl-6-(2-furoyl)oxy-4a, 5,6,7-tetrahydronaphtho[2,3-b]furan-2(4H)-one The title compound was prepared in the same manner as in Example B29, except that the compound prepared in Example B26 was reacted with 2-furoyl chloride.

$^1$H NMR (CDCl$_3$) δ 1.14 (d, J=7.2 Hz, 3H), 1.30 (s, 3H), 2.00 (dq, J=7.2, 2.5 Hz, 1H), 2.40 (br d, J=16.7 Hz, 1H), 2.56 (dd, J=21.4, 4.9 Hz, 1H), 2.69 (br ddd, J=21.4, 8.1, 3.6 Hz, 1H), 3.00 (d, J=16.7 Hz, 1H), 5.38 (br d, J=5.6 Hz, 1H), 5.82 (br t, 1H), 5.88 (s, 1H), 6.11 (s, 1H), 6.51 (dd, J=3.6, 1.8 Hz, 1H), 7.12 (dd, J=3.6, 0.8 Hz, 1H), 7.58 (dd, J=1.8, 0.8 Hz, 1H); MS (ESI) m/z 327(M+H)+.

Example B31

(5'S*,6'R*,7'R*)-Spiro[1,3-dioxolane-2,8'-(5',6', 7'-trimethylbicyclo[4,4,0]deca-1'-ene-3'-one)]

The compound (4) (in the structural formula, R$^5$=H) (500 mg, 2.1 mmol) was dissolved in toluene (30 ml), DDQ (700 mg, 3.1 mmol) was added thereto, and the mixture was heated under reflux for 10 hr. The reaction solution was cooled, and the resultant precipitate was filtered, and the solvent was removed by distillation under reduced pressure. The residue was purified by column chromatography on silica gel (hexane:ethyl acetate=4:1) to give a Δ$^{1,4}$-dienone form (490 mg, 98%).

Cuprous iodide (1.5 g, 8 mmol) was added to anhydrous diethyl ether (15 ml) under an argon gas stream, and the mixture was cooled to 0° C. A 1.0 M methyllithium diethyl ether solution (16 ml, 16 mmol) was added thereto, and the mixture was stirred for 15 min. A solution of the above compound (890 mg, 3.8 mmol) in diethyl ether (10 ml) was added to the reaction solution, and the mixture was stirred for 15 min. A saturated aqueous ammonium chloride solution was added to the reaction solution, followed by extraction with ethyl acetate. The organic layer was washed with saturated saline and dried over magnesium sulfate, and the solvent was removed by distillation under reduced pressure. The residue was purified by column chromatography on silica gel (hexane:ethyl acetate=2:1) to give the title compound (5) (in the structural formula, R$^3$=CH$_3$ and R$^5$=H) (594 mg, 63%).

$^1$H NMR (CDCl$_3$) δ 0.90 (d, J=6.9 Hz, 3H), 0.96 (d, J=6.9 Hz, 3H), 1.35 (s, 3H), 1.54 (ddd, J=17.8, 13.3, 4.4 Hz, 1H), 1.92 (ddd, J=13.3, 5.0, 3.0 Hz, 1H), 2.10 (q, J=6.9 Hz, 1H), 2.10–2.20 (m, 2H), 2.28 (ddd, J=15.0, 4.2, 2.7 Hz, 1H), 2.63 (dddd, J=17.8, 15.0, 4.2, 2.7 Hz, 1H), 2.77 (dd, 1H), 3.84–4.11 (m, 4H), 5.75 (s, 1H); MS (EI) m/z 250 (M)+.

Example B32

(4'S*,5'S,6'R*,7'R*)-Spiro[1,3-dioxolane-2,8'-[4'-(1"-hydroxy-1"-methoxycarbonyl)ethyl-5',6',7'-trimethylbicyclo[4,4,0]deca-1'-en-3'-one]]

A 2 M solution of lithium diisopropylamide in THF (3.5 ml, 17.5 mmol) was added to anhydrous THF (5 ml) at −78° C. under an argon gas stream, a THF solution (10 ml) containing the compound prepared in Example B31 (690 mg, 2.8 mmol) was added thereto, and the mixture was stirred for one hr. Subsequently, a saturated solution of zinc chloride in THF (3.5 ml) and an anhydrous THF solution containing methyl pyruvate (850 mg, 8.3 mmol) were successively added, and the mixture was stirred at −78° C. for one hr. A saturated aqueous ammonium chloride solution was added thereto, followed by extraction with methylene chloride. The organic layer was washed with saturated saline and dried over magnesium sulfate, and the solvent was removed by distillation under reduced pressure. The residue was purified by column chromatography on silica gel (hexane:ethyl acetate=4:1) to give the title compound (6) (in the structural formula, R$^3$=CH$_3$, R$^4$=CH$_3$, R$^5$=H, and R$^6$=CH$_3$) (763 mg, 78%).

$^1$H NMR (CDCl$_3$) δ 0.85–0.96 (d×2, J=6.8 Hz, 3H), 1.02–1.11 (d×2, J=7.2 Hz, 3H), 1.44 (s×2, 3H), 1.55–1.63 (m, 2H), 1.86–1.91 (m, 1H), 2.15 (q, J=6.8 Hz, 1H), 2.27–2.38 (m, 2H), 2.58–2.67 (m, 1H), 3.74–4.13 (m, 7H), 5.79 (s×2, 1H); MS (FAB) m/z 353 (M+H)+.

Example B33

(4R*,4aR*,5R*)-4a,7-Dihydro-3,4,4a,5-tetramethylnaphtho[2,3-b]furan-2,6(4H,5H)-dione The compound prepared in Example B32 (760 mg, 2.2 mmol) was dissolved in benzene (30 ml), p-toluenesulfonic acid (300 mg, 1.8 mmol) was added to the solution, and the mixture was heated under reflux for 4 hr. The reaction mixture was cooled, and a saturated aqueous sodium bicarbonate solution was added thereto, followed by extraction with ethyl acetate. The organic layer was washed with saturated saline and dried over magnesium sulfate, and the solvent was removed by distillation under reduced pressure. The residue was purified by column chromatography on silica gel (hexane:ethyl acetate=4:1) to give the title compound (460 mg, 85%).

$^1$H NMR (CDCl$_3$) δ 0.90 (s, 3H), 1.10 (d, J=7.2 Hz, 3H), 1.12 (d, J=6.7 Hz, 3H),1.95 (s, 3H), 2.80 (q, J=7.2 Hz, 1H), 2.95 (q, J=6.7 Hz, 1H), 2.99 (br dd, J=22.8, 3.8 Hz, 1H), 3.20 (dd, J=22.8, 3.8 Hz, 1H), 5.91 (m, 1H), 5.98 (s, 1H); MS (EI) m/z 258 (M)+.

Example B34

(4R*,4aR*,5R*,6S*)-6-Hydroxy-4a,5,6,7-tetrahydro-3,4,4a,5-tetramethylnaphtho[2,3-b]furan-2(4H)-one The compound prepared in Example B33 (600 mg, 2.1 mmol) was dissolved in methanol (150 ml), sodium borohydride (45 mg, 1.8 mmol) was added thereto, and the mixture was stirred at 25° C. for 30 min. A saturated aqueous ammonium chloride solution was added to the reaction solution, followed by extraction with ethyl acetate. The organic layer was washed with saturated saline and dried over magnesium sulfate, and the solvent was removed by distillation under reduced pressure. The residue was purified by column chromatography on silica gel (hexane:ethyl acetate=4:1) to give the title compound (310 mg, 51%).

$^1$H NMR (CDCl$_3$) δ 0.94 (d, J=7.5 Hz, 3H), 1.13 (s, 3H), 1.14 (d, J=7.2 Hz, 3H), 1.93 (s, 3H), 1.95 (dq, J=7.5, 2.0 Hz, 1H), 2.40 (br dd, J=19.8, 5.4 Hz, 1H), 2.60 (br ddd, J=19.8, 5.4 ,3.8 Hz, 1H), 2.82 (q, J=7.2 Hz, 1H), 4.09 (br s, 1H), 5.88 (m, 1H), 5.95 (s, 1H); MS (EI) m/z 260 (M)$^+$.

Example B35

(4R*,4aR*,5R*,6S*)-6-Acetoxy-4a,5,6,7-tetrahydro-3,4,4a,5-tetramethylnaphtho[2,3-b]furan-2(4H)-one The compound prepared in Example B34 (10 mg, 0.04 mmol) was dissolved in methylene chloride (1.0 ml), 4-dimethylaminopyridine (15.0 mg, 0.12 mmol) and acetyl chloride (20.0 mg, 0.3 mmol) were added thereto, and the mixture was stirred at 25° C. for 7 hr. Water was added to the reaction solution, followed by extraction with methylene chloride. The organic layer was washed with saturated saline and dried over magnesium sulfate, and the solvent was removed by distillation under reduced pressure. The residue was purified by preparative TLC (hexane:ethyl acetate=4:1) to give the title compound (5.7 mg, 50%).

$^1$H NMR (CDCl$_3$) δ 0.95 (d, J=7.1 Hz, 3H), 1.04 (d, J=7.1 Hz, 3H), 1.60 (s, 3H), 1.93 (s, 3H), 2.06 (s, 3H), 2.11 (dq, J=7.2, 2.5 Hz, 1H), 2.40 (br dd, J=20.6, 5.3 Hz, 1H), 2.60 (br ddd, J=20.6, 5.3, 3.8 Hz, 1H), 2.84 (q, J=7.2 Hz, 1H), 5.18 (m, 1H), 5.84 (m, 1H), 5.94 (s, 1H); MS (ESI) m/z 303 (M+H)$^+$.

Example B36

(4R*,4aR*,5R*,6S*)-6-Propionyloxy-4a,5,6,7-tetrahydro-3,4,4a,5-tetramethylnaphtho[2,3-b]furan-2(4H)-one The title compound was prepared in the same manner as in Example B35, except that the compound prepared in Example B34 was reacted with propionyl chloride.

$^1$H NMR (CDCl$_3$) δ 0.95 (d, J=7.2 Hz, 3H), 1.04 (d, J=7.2 Hz, 3H), 1.16 (s, 3H), 1.16 (t, J=7.4 Hz, 3H), 1.93 (s, 3H), 2.12 (dq, J=7.2, 2.8 Hz, 1H), 2.34 (q, J=7.4 Hz, 2H), 2.38 (br dd, J=19.3, 5.5 Hz, 1H), 2.60 (br ddd, J=19.3, 5.5, 3.8 Hz, 1H), 2.84 (q, J=7.4 Hz, 1H), 5.20 (m, 1H), 5.83 (m, 1H), 5.94 (s, 1H); MS (ESI) m/z 317 (M+H)$^+$.

Example B37

(4R*,4aR*,5R*,6S*)-6-Benzoyloxy-4a,5,6,7-tetrahydro-3,4,4a,5-tetramethylnaphtho[2,3-b]furan-2(4H)-one The compound prepared in Example B34 (10 mg, 0.04 mmol) was dissolved in pyridine (1.0 ml), benzoyl chloride (25.0 mg, 0.18 mmol) was added thereto, and the mixture was stirred at 25° C. for 2.5 hr. A 15% aqueous potassium hydrogensulfate solution was added to the reaction solution, followed by extraction with ethyl acetate. The organic layer was washed with saturated saline and dried over magnesium sulfate, and the solvent was removed by distillation under reduced pressure. The residue was purified by preparative TLC (hexane:ethyl acetate=4:1) to give the title compound (5.7 mg, 50%).

$^1$H NMR (CDCl$_3$) δ 0.99 (d, J=7.2 Hz, 3H), 1.12 (d, J=7.2 Hz, 3H), 1.32 (s, 3H), 1.95 (s, 3H), 2.24 (dq, J=7.2, 2.5 Hz, 1H), 2.55 (br dd, J=20.8, 5.1 Hz, 1H), 2.69–2.76 (m, 1H), 2.88 (q, J=7.2 Hz, 1H), 5.46 (m, 1H), 5.87 (m, 1H), 5.97 (s, 1H), 7.42–7.99 (m, 5H); MS (FAB) m/z 365 (M+H)$^+$.

Example B38

(4R*,4aR*,5R*,6S*)-6-(2-Furoyl)oxy-4a,5,6,7-tetrahydro-3,4,4a,5-tetramethylnaphtho[2,3-b]furan-2(4H)-one The title compound was prepared in the same manner as in Example B37, except that the compound prepared in Example B34 was reacted with 2-furoyl chloride.

$^1$H NMR (CDCl$_3$) δ 0.98 (d, J=7.2 Hz, 3H), 1.10 (d, J=7.2 Hz, 3H), 1.28 (s, 3H), 1.95 (s, 3H), 2.20 (dq, J=7.2, 2.5 Hz, 1H), 2.53 (br dd, J=20.8, 5.0 Hz, 1H), 2.69 (br ddd, J=20.8, 5.0, 3.8 Hz, 1H), 2.87 (q, J=7.2 Hz, 1H), 5.41 (m, 1H), 5.86 (m, 1H), 5.96 (s, 1H), 6.50 (dd, J=3.6, 1.8 Hz, 1H), 7.11 (dd, J=3.6, 0.8 Hz, 1H), 7.58 (dd, J=1.8, 0.8 Hz, 1H); MS (ESI) m/z 355 (M+H)$^+$.

Example 39

(4aR*,5R*,6R*,7S*)-6,7-Dihydroxy-4a,5,6,7-tetrahydro-3,4a,5-trimethylnaphtho[2,3-b]furan-2(4H)-one The compound prepared in Example B1 (5 mg, 0.02 mmol) was dissolved in dioxane (1 ml), selenium dioxide (22 mg, 0.20 mmol) was added thereto, and the mixture was stirred at 50° C. for 2 days. The reaction solution was filtered, and the solvent was removed by distillation under reduced pressure. The residue was purified by preparative TLC (hexane:ethyl acetate=1:1) to give the title compound (4.5 mg, 86%).

Reference Example 2

(4aR*,5R*,6R*,7S*)-6-Hydroxy-7-propionyloxy-4a,5,6,7-tetrahydro-3,4a,5-trimethylnaphtho[2,3-b]furan-2(4H)-one The compound prepared in Example B39 (15 mg, 0.06 mmol) was dissolved in methylene chloride (0.3 ml), diisopropylethylamine (25 μl, 0.14 mmol) and propionyl chloride (12 mg, 0.13 mmol) were added to the solution under ice cooling, and the mixture was stirred under ice cooling for 30 min and then at 25° C. for 17 hr. Water was added to the reaction solution, followed by extraction with chloroform. The organic layer was washed with a 5% aqueous potassium hydrogensulfate solution and then with a saturated aqueous sodium bicarbonate solution and dried over anhydrous sodium sulfate, and the solvent was then removed by distillation under reduced pressure. The residue was purified by preparative TLC (hexane:ethyl acetate=1:1) to give the title compound (8.2 mg, 45%).

Reference Example 3

(4aR*,5R*,6R*,7S*)-7-Hydroxy-6-propionyloxy-4a,5,6,7-tetrahydro-3,4a,5-trimethylnaphtho[2,3-b]furan-2(4H)-one The compound prepared in Example B39 (9.9 mg, 0.04 mmol) was dissolved in methylene chloride (0.2 ml), 4-dimethylaminopyridine (4.5 mg, 0.04 mmol) and propionyl chloride (9 mg, 0.09 mmol) were added to the solution under ice cooling, and the mixture was stirred under ice cooling for 30 min and then at 25° C. for 22 hr. Water was added to the reaction solution, followed by extraction with chloroform. The organic layer was washed with a 5% aqueous potassium hydrogensulfate solution and then with a saturated aqueous sodium bicarbonate solution and dried over anhydrous sodium sulfate, and the solvent was then removed by distillation under reduced pressure. The residue was purified by preparative TLC (hexane:ethyl acetate=1:1) to give the title compound (4.9 mg, 41%).

Reference Example 4

(4aR*,5R*,6R*,7S*)-6,7-Dipropionyloxy-4a,5,6,7-tetrahydro-3,4a,5-trimethylnaphtho[2,3-b]furan-2(4H)-one The compound prepared in Example B39 (16 mg, 0.06 mmol) was dissolved in methylene chloride (0.35 ml), 4-dimethylaminopyridine (38 mg, 0.31 mmol) and propionyl chloride (24 μl, 0.28 mmol) were added to the solution under ice cooling, and the mixture was stirred under ice cooling for 30 min and then at 25° C. for 18 hr. Water was added to the reaction solution, followed by extraction with chloroform. The organic layer was washed with a 5% aqueous potassium hydrogensulfate solution and then with a saturated aqueous sodium bicarbonate solution and dried over anhydrous sodium sulfate, and the solvent was then removed by distillation under reduced pressure. The residue was purified by preparative TLC (toluene:ethyl acetate=5:1) to give the title compound (20 mg, 85%).

Example B40

(4aR*,5R*,6R*,7S*)-6,7-Dihydroxy-4a,5,6,7-tetrahydro-3,4a,5,9-tetramethylnaphtho[2,3-b]furan-2(4H)-one The title compound was prepared in the same manner as in Example B39, except that the compound prepared in Example B13 was reacted with selenium dioxide.

$^1$H NMR (CDCl$_3$) δ 1.17 (s, 3H), 1.25 (d, J=7.2 Hz, 3H), 1.80 (dq, J=7.2, 1.5 Hz, 1H), 1.90 (s, 3H), 2.03 (s, 3H), 2.17 (d, J=16.4 Hz, 1H), 2.25–2.37 (m, 2H), 2.83 (d, J=16.4 Hz, 1H), 3.93 (br s, 1H), 4.40 (br s, 1H), 5.76 (s, 1H); MS (ESI) m/z=277(M+H)$^+$.

Example B41

(4aR*,5R*,6R*,7S*)-6,7-Dihydroxy-4a,5-dimethyl-3-ethyl-4a,5,6,7-tetrahydronaphtho[2,3-b]furan-2(4H)-one The title compound was prepared in the same manner as in Example B39, except that the compound prepared in Example B20 was reacted with selenium dioxide.

$^1$H NMR (CDCl$_3$) δ 1.13 (t, J=7.5 Hz, 3H), 1.23 (d, J=7.2 Hz, 3H), 1.26 (d, J=2.7 Hz, 3H), 1.80 (dq, J=7.2, 1.5 Hz, 1H), 2.20 (d, J=16.1 Hz, 1H), 2.30–2.40 (m, 2H), 2.87 (d, J=16.1 Hz, 1H), 3.94 (br s, 1H), 4.37 (br s, 1H), 5.65 (s, 1H), 5.98 (s, 1H); MS (ESI) m/z=276 (M)$^+$.

Example B42

The compound prepared in Example B2 was dissolved in ethanol and adjusted to a concentration of 0.5 mg/ml. This sample was chromatographed using an optical resolution column (CHIRALPAK AS) by elution with a mobile phase (hexane:isopropyl alcohol=9:1) to give optical isomers.

Angle of rotation: front peak: +10.2° (nonnatural type) rear peak: −10.2° (natural type)

Example B43

(6'R*,7'R*)-Spiro[1,3-dioxolane-2,3'-(6',7'-dimethylbicyclo[4,4,0]-deca-1'-en-8'-one)]

Compound (4) (in the structural formula, R$^5$=H) (1 g, 4.24 mmol) was dissolved in methylene chloride (50 ml), and the solution was cooled to 0° C. A 60% aqueous perchloric solution (1 ml) was added to the solution, and the mixture was stirred at that temperature for one hr and then at room temperature for 20 min. A saturated aqueous sodium bicarbonate solution (25 ml) was added to the reaction solution, followed by separation. The organic layer was washed with saturated saline and dried over magnesium sulfate, and the solvent was removed by distillation under reduced pressure. The residue was purified by column chromatography on silica gel (hexane:ethyl acetate=2:1) to give a corresponding diketone form (797 mg, 78%). The above compound (790 mg, 4.11 mmol) was dissolved in anhydrous methylene chloride (5 ml) under an argon gas stream, trimethylsilyl trifluoromethanesulfonate (17 μl, 0.02 mmol) and 1,2-bis(trimethylsilyloxy)ethane (1.2 ml, 4.3 mmol) were added to the solution at −78° C., and the mixture was stirred at that temperature for 4 days. An excess of pyridine was added to the reaction solution, the temperature of the mixture was raised to 25° C., a saturated aqueous ammonium chloride solution was added thereto, followed by extraction with ethyl acetate. The organic layer was washed with saturated saline and dried over magnesium sulfate, and the solvent was removed by distillation under reduced pressure. The residue was purified by column chromatography on silica gel (hexane:ethyl acetate=2:1) to give the title compound (730 mg, 75%).

$^1$H NMR (CDCl$_3$) δ 0.92 (s, 3H), 0.98 (d, J=6.8 Hz, 3H), 1.64–1.86 (m,4H), 2.47–2.50 (m, 4H), 2.56–2.68 (m, 1H), 3.92 –4.08 (m, 4H), 5.47 (s, 1H); MS (ESI) m/z 237 (M+H)$^+$.

Example B44

(6R*,7S*,8S*,9R*)-8-Hydroxy-6,7,9-trimethylbicyclo[4,4,0]deca-1-en-3-one

A 2 M solution of lithium diisopropylamide in THF (2.0 ml, 4.0 mmol) were added to anhydrous THF (2 ml) at −78° C. under an argon gas stream, a THF solution (5 ml) containing the compound (8) (in the structural formula, R$^3$=H and R$^5$=H) (730 mg, 3.8 mmol) was added thereto, and the mixture was stirred for one hr. Methyl iodide (1.4 mg, 10 mmol) was added thereto, the temperature was raised to 25° C., and the mixture was stirred for one hr. A saturated aqueous ammonium chloride solution was added to the reaction mixture, followed by extraction with ethyl acetate. The organic layer was washed with saturated saline and dried over magnesium sulfate. The solvent was removed by distillation under reduced pressure. The resultant crude product was dissolved in THF (10 ml), lithium borohydride (30 mg, 1.4 mmol) was added thereto, and the mixture was stirred at 25° C. for 14 hr. A saturated aqueous ammonium chloride solution was added to the reaction mixture, followed by extraction with methylene chloride. The organic layer was washed with saturated saline and dried over magnesium sulfate, and the solvent was removed by distillation under reduced pressure. Subsequently, the resultant crude product was dissolved in acetone (10 ml), p-toluenesulfonic acid (20 mg, 0.1 mmol) was added thereto, and the mixture was stirred at 25° C. for 20 min. A saturated sodium bicarbonate solution was added to the reaction solution, followed by extraction with ethyl acetate. The organic layer was washed with saturated saline and dried over magnesium sulfate, and the solvent was removed by distillation under reduced pressure. The residue was purified by column chromatography on silica gel (hexane:ethyl acetate=4:1) to give the title compound (250 mg, 40%).

$^1$H NMR (CDCl$_3$) δ 0.91 (d, J=7.3 Hz, 3H), 1.08 (d, J=7.3 Hz, 3H), 1.31 (s, 3H), 1.64 (dq, J=7.3, 2.9 Hz, 1H), 1.61–1.73 (m, 2H), 1.93 (br d, J=13.9 Hz, 1H), 2.03 (ddd, J=13.9, 5.1, 2.9 Hz, 1H), 2.12–2.20 (m, 1H), 2.29–2.35 (m, 1H), 2.45 (dd, J=14.6, 5.1 Hz, 1H), 3.04 (ddd, J=14.6, 3.6, 1.7 Hz, 1H), 3.61 (s, 1H), 5.79 (s, 1H); MS (ESI) m/z 209 (M+H)$^+$.

Example B45

(4S*,6R*,7R*,8S*,9R*)-4-(1'-Hydroxy-1'-methoxycarbonyl)ethyl-8-[(2-methoxyethoxy)methoxy]-6,7,9-trimethylbicyclo[4,4,0]deca-1-en-3-one Compound (9) (in the structural formula, R$^1$=CH$_3$, R$^3$=H, and R$^5$=H) (245 mg, 1.18 mmol) was dissolved in methylene chloride (8 ml), diisopropylethylamine (300 mg, 2.36 mmol) and β-methoxyethoxymethyl chloride (300 mg, 2.36 mmol) were added thereto, and the mixture was stirred at 25° C. for 14 hr. A saturated aqueous ammonium chloride solution was added to the reaction solution, followed by extraction with ethyl acetate. The organic layer was washed with saturated saline and dried over magnesium sulfate, and the solvent was removed by distillation under reduced pressure. The residue was purified by column chromatography on silica gel (hexane:ethyl acetate=4:1) to give a corresponding MEM form (307 mg, 88%). A 2 M solution of lithium diisopropylamide in THF (0.5 ml, 1.0 mmol) was added to anhydrous THF (2 ml) at −78° C. under an argon gas stream, a THF solution (4 ml) containing the compound prepared just above (307 mg, 1.0 mmol) was added thereto, and the mixture was stirred for one hr. Subsequently, a saturated solution of zinc chloride in THF (0.3 ml) and a THF solution (2 ml) containing methyl pyruvate (150 mg, 1.5 mmol) were successively added, and the mixture was stirred at −78° C. for 20 min. A saturated aqueous ammonium chloride solution was added thereto, followed by extraction with ethyl acetate. The organic layer was washed with saturated saline and dried over magnesium sulfate, and the solvent was removed by distillation under reduced pressure. The residue was purified by column chromatography on silica gel (hexane:ethyl acetate=4:1) to give the title compound (310 mg, 75%).

$^1$H NMR (CDCl$_3$) δ 0.86 (d×2, J=7.0 Hz, 3H), 1.04–1.08 (d×2, J=7.2 Hz, 3H), 1.30 (s, 3H), 1.32–1.34 (s×2, 3H), 1.67–1.79 (m, 2H), 1.90–2.19 (m, 2H), 2.28–2.31 (m, 1H), 2.71–3.03 (dd×3, J=14.0, 5.1 Hz, 2H), 3.36–3.40 (s×2, 3H), 3.45 (br s, 1H), 3.71–3.79 (s×2, 3H), 3.56–3.83 (m, 4H), 4.71–4.84 (d×2, J=7.1 Hz, 2H), 5.73–5.75 (s×2, 1H); MS (ESI) m/z 399 (M+H)$^+$.

Example B46

(4aR*,5R*,6S*,7R*)-6-Hydroxy-4a,5,6,7-tetrahydro-3,4a,5,7-tetramethylnaphtho[2,3-b]furan-2(4H)-one Compound (10) (in the structural formula, R$^1$=CH$_3$, R$^3$=H, R$^4$=CH$_3$, R$^5$=H, and P$^1$≈MEM) (310 mg, 0.78 mmol) was dissolved in benzene (10 ml), p-toluenesulfonic acid (80 mg, 0.42 mmol) was added to the solution, and the mixture was heated under reflux for 30 min. The reaction solution was cooled, a saturated aqueous sodium bicarbonate solution was added thereto, followed by extraction with ethyl acetate. The organic layer was washed with saturated saline and dried over magnesium sulfate, and the solvent was then removed by distillation under reduced pressure. The residue was purified by column chromatography on silica gel (hexane:ethyl acetate=4:1) to give the title compound (60 mg, 30%).

$^1$H NMR (CDCl$_3$) δ 0.98 (d, J=7.6 Hz, 3H), 1.10 (s, 3H), 1.14 (d, J=7.3 Hz, 3H), 1.72 (dq, J=7.3, 2.4 Hz, 1H), 1.84 (s, 3H), 2.10 (br d, J=16.1 Hz, 1H), 2.41 (m, 1H), 2.77 (d, J=16.1 Hz, 1H), 3.62 (br s, 1H), 5.67 (d, J=4.6 Hz, 1H), 5.91 (s, 1H); MS (ESI) m/z 261 (M+H)$^+$.

Example B47

(4aR*,5R*,6S*,7R*)-6-Acetoxy-4a,5,6,7-tetrahydro-3,4a,5,7-tetramethylnaphtho[2,3-b]furan-2(4H)-one The compound prepared in Example B46 (8 mg, 0.03 mmol) was dissolved in methylene chloride (1.0 ml), 4-dimethylaminopyridine (15 mg, 0.12 mmol) and acetyl chloride (20.0 mg, 0.3 mmol) were added thereto, and the mixture was stirred at 25° C. for 14 hr. Water was added to the reaction solution, followed by extraction with methylene chloride. The organic layer was washed with saturated saline and dried over magnesium sulfate, and the solvent was removed by distillation under reduced pressure. The residue was purified by preparative TLC (hexane:ethyl acetate=4:1) to give the title compound (5.1 g, 55%).

$^1$H NMR (CDCl$_3$) δ 1.10 (d, J=7.1 Hz, 3H), 1.11 (d, J=7.3 Hz, 3H), 1.15 (s, 3H), 1.92 (s, 3H), 1.92 (dq, J=7.3, 2.7 Hz, 1H), 2.06 (s, 3H), 2.20 (br d, J=16.1 Hz, 1H), 2.44 (m, 1H), 2.86 (d, J=16.1 Hz, 1H), 4.81 (m, 1H), 5.69 (d, J=4.6 Hz, 1H), 5.97 (s, 1H); MS (ESI) m/z 303 (M+H)$^+$.

Example B48

(4aR*,5R*,6S*,7R*)-6-Propionyloxy-4a,5,6,7-tetrahydro-3,4a,5,7-tetramethylnaphtho[2,3-b]furan-2(4H)-one The title compound was prepared in the same manner as in Example B47, except that the compound prepared in Example B46 was reacted with propionyl chloride.

$^1$H NMR (CDCl$_3$) δ 1.09 (d, J=7.5 Hz, 3H), 1.12 (d, J=8.0 Hz, 3H), 1.14 (s, 3H), 1.14 (t, J=7.5 Hz, 3H), 1.92 (s, 3H), 1.94 (dq, J=7.8, 2.7 Hz, 1H), 2.02 (d, J=16.8 Hz, 1H), 2.34 (q, J=7.5 Hz, 2H), 2.42 (m, 1H), 2.85 (d, J=16.8 Hz, 1H), 4.81 (m, 1H), 5.69 (d, J=4.6 Hz, 1H), 5.96 (s, 1H); MS (ESI) m/z 317 (M+H)$^+$.

Example B49

(4aR*,5R*,6S*,7R*)-6-Benzoyloxy-4a,5,6,7-tetrahydro-3,4a,5,7-tetramethylnaphtho[2,3-b]furan-2(4H)-one The compound prepared in Example B46 (10 mg, 0.04 mmol) was dissolved in pyridine (1.0 ml), benzoyl chloride (25.0 mg, 0.18 mmol) was added thereto, and the mixture was stirred at 25° C. for 2.5 hr. A 15% aqueous potassium hydrogensulfate solution was added to the reaction solution, followed by extraction with ethyl acetate. The organic layer was washed with saturated saline and dried over magnesium sulfate, and the solvent was removed by distillation under reduced pressure. The residue was purified by preparative TLC (hexane:ethyl acetate=4:1) to give the title compound (4.0 mg, 35%).

$^1$H NMR (CDCl$_3$) δ 1.18 (d, J=7.1 Hz, 3H), 1.20 (d, J=7.6 Hz, 3H), 1.31 (s, 3H), 1.94 (s, 3H), 2.07 (dq, J=7.1, 2.9 Hz, 1H), 2.27 (br d, J=16.1 Hz, 1H), 2.60 (br dq, J=7.1, 4.4 Hz, 1H), 2.91 (d, J=16.1 Hz, 1H), 5.07 (m, 1H), 5.73 (d, J=4.4 Hz, 1H), 6.00 (s, 1H), 7.42–8.12 (m, 5H); MS (ESI) m/z 365 (M+H)$^+$.

Example B50

(4aR*,5R*,6S*,7R*)-6-(2-Furoyl)oxy-4a,5,6,7-tetrahydro-3,4a,5,7-tetramethylnaphtho[2,3-b]furan-2(4H)-one The title compound was prepared in the same manner as in Example B49, except that the compound prepared in Example B46 was reacted with 2-furoyl chloride.

$^1$H NMR (CDCl$_3$) δ 1.16 (d, J=7.1 Hz, 3H), 1.17 (d, J=7.3 Hz, 3H), 1.26 (s, 3H), 1.93 (s, 3H), 2.02 (dq, J=7.3, 2.7 Hz, 1H), 2.24 (br d, J=16.1 Hz, 1H), 2.57 (br dq, J=7.3, 4.6 Hz, 1H), 2.89 (d, J=16.1 Hz, 1H), 5.04 (m, 1H), 5.72 (d, J=4.6 Hz, 1H), 5.99 (s, 1H), 6.50 (dd, J=3.6, 1.8 Hz, 1H), 7.11 (dd, J=3.6, 0.7 Hz, 1H), 7.58 (d, J=1.8, 0.7 Hz, 1H); MS (ESI) m/z 355 (M+H)$^+$.

Example C1

(3R,4R,5R)-(−)-3,4-Dimethyl-5-hydroxymethyl-2-furanone (R)-(+)-5-Hydroxymethyl-2 (5H)-furanone (1.94 g, 17.0 mmol) was dissolved in anhydrous pyridine (60 mol), triphenylmethyl chloride (14.3 g, 51.2 mmol) was added to the solution at room temperature, and the mixture was stirred for 6 hr. Ethanol was added to the reaction solution at 0° C., and the mixture was stirred for one hr. The reaction solution was concentrated under reduced pressure, and the concentrate was subjected to azeotropic distillation twice with toluene and purified by column chromatographic separation on silica gel (hexane:ethyl acetate=3:1 to 2:1) to give (R)-(+)-5-triphenylmethyloxymethyl-2 (5H)-furanone (5.47 g, 90%).

$^1$H NMR (CDCl$_3$) δ 3.39 (dd, J=10.0, 5.0 Hz, 1H), 3.41 (dd, J=10.0, 5.0 Hz, 1H), 5.08 (dddd, J=5.0, 5.0, 1.5, 1.5 Hz, 1H), 6.19 (dd, J=6.0, 2.0 Hz, 1H), 7.2–7.5 (m, 16H); [α]$_D$ +87° (c 0.7, CHCl$_3$).

Copper iodide (I) (6.49 g, 34.1 mmol) was suspended in anhydrous ether (120 ml) under an argon atmosphere, and a 1.0 M solution of methyllithium in ether (64.9 ml, 64.9 mmol) was added to the suspension at 0° C. The resultant colorless and transparent solution was cooled to −78° C., and chlorotrimethylsilane (4.3 ml, 34.0 mmol) was added thereto. The mixture was stirred for 15 min, and a solution of the compound prepared just above (6.06 g, 17.0 mmol) in anhydrous THF (8 ml) was added to the reaction solution, followed by stirring for 2 hr. The reaction solution was poured into a mixed solution of ethyl acetate and water, sodium thiosulfate was added thereto, and the mixture was stirred until the mixed solution became colorless and transparent, followed by separation. The organic layer was concentrated under reduced pressure. The concentrate was then purified by column chromatographic separation on silica gel (hexane:ethyl acetate=3:1) to give (4R,5R)-(−)-4-methyl-5-triphenylmethyloxymethyl-2-furanone (4.50 g, 71%).

$^1$H NMR (CDCl$_3$) δ 1.16 (d, J=7.0 Hz, 3H), 2.17 (dd, J=17.5, 7.0 Hz, 1H), 2.48 (dddq, J=8.0, 8.0, 8.0, 7.0 Hz, 1H), 2.82 (dd, J=17.5, 8.0 Hz, 1H), 3.18 (dd, J=11.0, 4.0 Hz, 1H), 3.42 (dd, J=11.0, 3.0 Hz, 1H), 4.14 (ddd, J=8.0, 4.0, 3.0 Hz, 1H), 7.2–7.5 (m, 15H); [α]$_D$ −34° (c 1.2, CHCl$_3$).

The compound prepared just above (2.14 g, 5.77 mmol) was dissolved in anhydrous THF (43 ml) under an argon atmosphere, and a 1.0 M solution of lithiumbistrimethylsilylamide in hexane (5.48 ml, 5.48 mmol) was added to the solution at −78° C. The solution was stirred for one hr, methyl iodide (3.59 ml, 57.7 mmol) was added thereto, and the mixture was stirred for additional 2 hr. The reaction solution was poured into a mixed solution of ethyl acetate and water, followed by separation. The organic layer was concentrated under reduced pressure. The concentrate was then purified by column chromatographic separation on silica gel (hexane ether=5:2) to give (3R,4R,5R)-(−)-3,4-dimethyl-5-triphenylmethyloxymethyl-2-furanone (1.32 g, 60%).

$^1$H NMR (CDCl$_3$) δ 0.95 (d, J=7.5 Hz, 3H), 1.16 (d, J=7.5 Hz, 3H), 2.47 (ddq, J=7.5, 7.5, 5.0 Hz, 1H), 2.87 (dq, J=7.5, 7.5 Hz, 1H), 3.20 (dd, J=10.5, 5.0 Hz, 1H), 3.40 (dd, J=10.5, 5.0 Hz, 1H), 4.14 (q-like, J=5.0 Hz, 1H), 7.2–7.5 (m, 15H); [α]$_D$ −34° (c 1.2, CHCl$_3$).

The compound (2.09 g, 5.41 mmol) prepared just above was dissolved in a 90% aqueous methanol solution (60 ml), Amberlyst IR-15 (H$^+$) (0.42 g) was added thereto, and a reaction was allowed to proceed at 80° C. for 19 hr. The resin was removed from the reaction solution by filtration, and the mother liquor was concentrated under reduced pressure. The concentrate was then purified by column chromatographic separation on silica gel (methylene chloride:ethyl acetate=3:1) to give the title compound (0.71 g, 92%).

$^1$H NMR (CDCl$_3$) δ 1.06 (d, J=7.0 Hz, 3H), 1.18 (d, J=7.5 Hz, 3H), 1.98 (t-like, J=7.0 Hz, 1H), 2.55 (ddq, J=7.5, 7.5, 7.0 Hz, 1H), 2.81 (dq, J=7.5, 7.5 Hz, 1H), 3.70 (ddd, J=12.5, 7.0, 5.0 Hz, 1H), 3.90 (ddd, J=12.5, 7.0, 3.0 Hz, 1H), 4.14 (ddd, J=7.5, 5.0, 3.0 Hz, 1H); [α]$_D$ −56° (c 2.1, CHCl$_3$).

Example C2

(3R,4R,5R)-(−)-5-Dimethoxymethyl-3,4-dimethyl-2-furanone

Oxalyl chloride (1.04 ml, 12.1 mmol) was dissolved in anhydrous methylene chloride (17.5 ml) under an argon atmosphere. The solution was cooled to −78° C., and a solution of DMSO (1.29 ml, 18.2 mmol) in anhydrous methylene chloride (2 ml) was dropwise added to the cooled solution. After foaming quieted down, a solution of the compound prepared in Example C1 (0.87 g, 6.07 mmol) in anhydrous methylene chloride (2 ml) was added to the reaction solution, and the mixture was stirred for 20 min. Triethylamine (4.23 ml, 30.3 mmol) was added thereto, and the mixture was stirred at −78° C. for 15 min and then at room temperature for 15 min. The reaction solution was poured into a mixed solution (50 ml) composed of methyl orthoformate and methanol (=4:1) and containing camphorsulfonic acid (7.75 g, 33.6 mmol), and a reaction was allowed to react at room temperature for 30 min. The reaction solution was concentrated under reduced pressure, and the concentrate was dissolved in a mixed solution of ethyl acetate and water, followed by separation. The organic phase was concentrated under reduced pressure, and the concentrate was then purified by column chromatographic separation on silica gel (hexane:ethyl acetate=4:1) to give the title compound (1.10 g, 96%).

$^1$H NMR (CDCl$_3$) δ 1.02 (d, J=7.0 Hz, 3H), 1.11 (d, J=7.5 Hz, 3H), 2.65 (ddq, J=9.0, 7.5, 3.5 Hz, 1H), 2.85 (dq, J=9.0, 7.5 Hz, 1H), 3.44 (s, 3H), 3.45 (s, 3H), 4.01 (dd, J=3.5, 3.0 Hz, 1H), 4.36 (d, J=3.0 Hz, 1H); MS (FAB) m/z 189 (M+H)+; $[\alpha]_D$ −4.00° (c 1.1, CHCl$_3$).

Example C3

(3R,4R,5R)-2-Benzenesulfonylmethyl-5-dimethoxymethyl-3,4-dimethyl-2-hydroxyoxolane Methylphenylsulfone (0.98 g, 6.25 mmol) was dissolved in anhydrous THF (30 ml) under an argon atmosphere. The solution was cooled to −78° C., and a 1.6 M solution of n-butyllithium in hexane (3.6 ml, 5.76 mmol) was dropwise added to the cooled solution. The mixture was stirred for 30 min, a solution of the compound prepared in Example C2 (0.90 g, 4.80 mmol) in anhydrous THF (4 ml) was added thereto, and the mixture was stirred at −78° C. for 30 min. After the completion of the reaction, an aqueous ammonium chloride solution was added, and the temperature of the mixture was raised to room temperature. The reaction solution was concentrated under reduced pressure, and ether was added to the concentrate, followed by separation. The organic layer was concentrated under reduced pressure, and the concentrate was then purified by column chromatographic separation on silica gel (methylene chloride:ethyl acetate=15:1) to give the title compound (1.41 g, 85%).

$^1$H NMR (CDCl$_3$): (major) δ 0.96 (d, J=7.5 Hz, 3H), 1.05 (d, J=7.0 Hz, 3H), 1.9–2.2 (m, 2H), 3.09 (s, 3H), 3.22 (s, 3H), 3.4–3.8 (m, 3H), 4.86 (s, 1H), 7.4–7.7 (m, 3H), 7.9–8.1 (m, 2H).

$^1$H NMR (CDCl$_3$): (minor) δ 0.82 (d, J=7.5 Hz, 3H), 0.99 (d, J=7.0 Hz, 3H), 2.3–2.7 (m, 2H), 3.37 (s, 3H), 3.41 (s, 3H), 3.4–3.8 (m, 2H), 4.29 (d, J=6.0 Hz, 1H), 4.75 (s, 1H), 7.4–7.7 (m, 3H), 7.9–8.1 (m, 2H).

Example C4

(3R,4R,5R)-1-Benzenesulfonyl-2,5-di(t-butyldimethylsilyloxy)-6,6-dimethoxy-3,4-dimethyl-1-hexene The compound (0.54 g, 1.18 mmol) prepared in Example C3 was dissolved in anhydrous THF (20 ml) under an argon atmosphere, 2,6-lutidine (0.40 ml, 3.55 mmol) and t-butyldimethylsilyl trifluoromethanesulfonate (0.57 ml, 2.35 mmol) were successively added to the solution, and a reaction was allowed to react at room temperature for 13 hr. After the completion of the reaction, the reaction solution was concentrated under reduced pressure, and the concentrate was then purified by column chromatographic separation on silica gel (toluene:ether=10:1) to give the title compound (0.61 g, 90%).

$^1$H NMR (CDCl$_3$) δ 0.06 (s, 3H), 0.09 (s, 3H), 0.23 (s, 6H), 0.8–0.9 (m, 3H), 0.89 (s, 18H), 1.15 (d, J=7.0 Hz, 3H), 1.5–1.6 (m, 1H), 2.37 (dq, J=11.5, 7.5 Hz, 1H), 3.33 (s, 3H), 3.44 (s, 3H), 3.73 (dd, J=7.0, 2.5 Hz, 1H), 4.12 (d, J=7.0 Hz, 1H), 5.60 (s, 1H), 7.4–7.6 (m, 3H), 7.8–7.9 (m, 2H).

Example C5

(4R,5R,6R)-(+)-2-Benzenesulfonyl-4-(t-butyldimethylsilyloxy)-5,6-dimethyl-2-cyclohexen-1-one The compound prepared in Example C4 (1.39 g, 2.43 mmol) was dissolved in anhydrous methylene chloride (30 ml) under an argon atmosphere. The solution was cooled to −78° C., and tin(IV) chloride (0.3 ml, 2.56 mmol) was dropwise added to the cooled solution. The reaction solution was stirred for one hr, tin(IV) chloride (0.6 ml, 5.12 mmol) was again dropwise added to the reaction solution, and the mixture was stirred for additional 2 hr. After the completion of the reaction, an aqueous sodium hydrogencarbonate solution was added thereto, and the temperature of the mixture was raised to room temperature, followed by separation. The organic layer was concentrated under reduced pressure, and the concentrate was then purified by column chromatographic separation on silica gel (toluene:ether=15:1) to give the title compound (0.87 g, 91%).

$^1$H NMR (CDCl$_3$) δ 0.15 (s, 3H), 0.19 (s, 3H), 0.74 (d, J=7.0 Hz, 3H), 0.95 (s, 9H), 1.05 (d, J=7.0 Hz, 3H), 2.32 (dddq, J=7.0, 5.0, 3.5, 1.5 Hz, 1H), 2.59 (dq, J=7.0, 3.5 Hz, 1H), 4.89 (dd, J=5.0, 1.5 Hz, 1H), 7.4–7.6 (m, 3H), 7.78 (t-like, J=1.5 Hz, 1H), 7.8–7.9 (m, 2H); MS (FAB) m/z 395 (M+H)$^+$; $[\alpha]_D$ +162° (c 1.2, CHCl$_3$).

Example C6

(2R,3R,4R)-(+)-4-t-Butyldimethylsilyloxy-2,3-dimethylcyclohexanone

The compound (0.41 g, 1.04 mmol) prepared in Example C5 was dissolved in a 90% aqueous 1,4-dioxane solution (25 ml), and disodium hydrogenphosphate (0.59 g, 4.18 mmol) was added to the solution. Aluminum-mercury amalgam (aluminum: 0.42 g, 15 mmol) was added to the reaction solution, and the mixture was vigorously stirred at room temperature for 4 hr. After the completion of the reaction, the alumina was removed by filtration, and the filtrate was concentrated under reduced pressure. The concentrate was again dissolved in a mixed solution of ether and water, followed by separation. The organic layer was concentrated under reduced pressure, and the concentrate was then purified by column chromatographic separation on silica gel (hexane:ether=6:1) to give the title compound (0.15 g, 56%).

$^1$H NMR(benzene-d$_6$) δ 0.05 (s, 3H), 0.06 (s, 3H), 0.82 (d, J=7.0 Hz, 3H), 0.99 (s, 9H), 1.03 (d, J=7.0 Hz, 3H), 1.5–1.6 (m, 1H), 1.75 (dddd, J=12.5, 12.5, 10.5, 5.0 Hz, 1H), 1.86 (ddd, J=13.5, 12.5, 7.0 Hz, 1H), 1.9–2.2 (m, 2H), 2.21 (ddd, J=13.5, 5.0, 3.5 Hz, 1H), 3.88 (ddd, J=10.0, 4.5, 4.5 Hz, 1H); $[\alpha]_D$ +24° (c 1.2, CHCl$_3$).

Example C7

(6R,7R,8S)-8-t-Butyldimethylsilyloxy-6,7-dimethylbicyclo[4,4,0]deca-1-en-3-one

The compound (0.18 g, 0.70 mmol) prepared in Example C6 was dissolved in anhydrous methylene chloride (3.6 ml) under an argon atmosphere. Hexamethyldisilazane (0.19 ml, 0.91 mmol) and trimethylsilane iodide (0.11 ml, 0.77 mmol) were successively added to the solution, and a reaction was allowed to react at room temperature for 30 min. The reaction solution was diluted with hexane, the resultant precipitate was removed through Florisil, and the filtrate was evaporated to dryness. The residue was dissolved in anhydrous THF (4.0 ml) under an argon atmosphere, and the solution was cooled to −78° C. A 1.0 M solution of methyllithium in ether (0.78 ml, 0.78 mmol) was added to the cooled solution, the temperature of the mixture was raised to room temperature, and the mixture was stirred for 30 min. The reaction solution was again cooled to −78° C., α-trimethylsilylmethyl vinyl ketone (0.24 g, 1.41 mmol) was added to the cooled solution, the temperature of the mixture was raised to 0° C., and the mixture was stirred for one hr. The reaction solution was diluted with ether, an aqueous ammonium chloride was added thereto, the temperature was raised to room temperature, followed by separation. The organic layer was evaporated to dryness. The residue was dissolved in methanol (3 ml), a 28% solution of sodium methoxide in methanol (0.14 g, 0.70 mmol) was added thereto, and a reaction was allowed to proceed at 50° C. for 2 hr. Ammonium chloride was added to the reaction solution to pH 7, and the reaction solution was then concentrated under reduced pressure. The concentrate was then purified by column chromatographic separation on silica gel (hexane:ethyl acetate=5:1) to give the title compound (0.12 g, 57%).

$^1$H NMR (CDCl$_3$) δ 0.07 (s, 3H), 0.08 (s, 3H), 0.93 (s, 9H), 1.01 (d, J=7.0 Hz, 3H), 1.30 (s, 3H), 1.42 (dq, J=7.0, 3.0 Hz, 1H), 1.6–1.7 (m, 1H), 1.65 (ddd, J=14.5, 14.5, 5.0 Hz, 1H), 1.90 (dddd, J=14.0, 6.0, 5.0, 3.0 Hz, 1H), 2.00 (ddd, J=14.5, 5.5, 3.0 Hz, 1H), 2.08 (ddd, J=14.0, 3.0, 3.0 Hz, 1H), 2.31 (dddd, J=18.0, 5.0, 3.0, 1.0 Hz, 1H), 2.47 (ddd, J=18.0, 14.5, 5.5 Hz, 1H), 2.82 (dddd, J=14.0, 14.0, 5.0, 2.0 Hz, 1H), 3.86 (br q, J=3.0 Hz, 1H), 5.76 (br s, 1H); MS (FAB) m/z 309 (M+H)$^+$; [α]$_D$ +142° (c 1.0, CHCl$_3$).

Example C8

(4R,6R,7R,8S)-8-t-Butyldimethylsilyloxy-4-(1'-hydroxy-1'-methoxycarbonyl)ethyl-6,7-dimethylbicyclo[4,4,0]deca-1-en-3-one The compound prepared in Example C7 (0.12 g, 0.40 mmol) was dissolved in anhydrous THF (3 ml) under an argon atmosphere, and a 1.0 M solution of lithiumbistrimethylsilylamide in hexane (2.0 ml, 2.0 mmol) was added to the solution at −78° C. The mixture was stirred for 30 min, a 1.0 M solution of zinc(II) chloride in ether (0.44 ml, 0.44 mmol) was poured into the mixture. The mixture was stirred for 10 min, methyl pyruvate (0.18 ml, 1.99 mmol) was dropwise added to the mixture, and the mixture was stirred for additional 30 min. Thereafter, the reaction solution was diluted with ether, an aqueous ammonium chloride solution was added thereto, the temperature was raised to room temperature, followed by separation. The organic layer was concentrated under reduced pressure, and the concentrate was then purified by column chromatographic separation on silica gel (hexane ethyl:acetate=3 1) to give the title compound (0.16 g, 97%).

$^1$H NMR (CDCl$_3$): (major) δ 0.07 (s, 6H), 0.93 (s, 9H), 1.02 (d, J=7.0 Hz, 3H), 1.3–2.2 (m, 12H), 2.71 (dd, J=13.5, 5.5 Hz, 1H), 2.80 (m, 1H), 3.73 (s, 3H), 3.86 (m, 1H), 4.87 (s, 1H), 5.75 (d, J=2.0 Hz, 1H);

$^1$H NMR (CDCl$_3$): (minor) δ 0.07 (s, 6H), 0.93 (s, 9H), 1.05 (d, J=7.0 Hz, 3H), 1.3–2.2 (m, 12H), 2.80 (m, 1H), 3.03 (dd, J=15.0, 5.0 Hz, 1H), 3.36 (s, 1H), 3.81 (s, 3H), 3.86 (m, 1H), 5.72 (d, J=2.0 Hz, 1H).

Example C9

(4aR,5R,6S)-(−)-6-Hydroxy-4a,5,6,7-tetrahydro-3,4a,5-trimethylnaphtho[2,3-b]furan-2(4H)-one The compound prepared in Example C8 (0.16 g, 0.39 mmol) was dissolved in a 90% aqueous 1,4-dioxane solution (8 ml), camphorsulfonic acid (0.10 g, 0.44 mmol) was added thereto, and a reaction was allowed to proceed at 105° C. for 28 hr. The reaction solution was neutralized with sodium hydrogencarbonate to pH 7 and then concentrated under reduced pressure. The concentrate was then purified by column chromatographic separation on silica gel (toluene:ether=2:1) to give the title compound (49 mg, 51%).

$^1$H NMR (CDCl$_3$) δ 1.18 (s, 3H), 1.21 (d, J=7.0 Hz, 3H), 1.76 (dq, J=7.0, 2.0 Hz, 1H), 1.91 (br s, 3H), 2.20 (br d, J=16.0 Hz, 1H), 2.42 (dd, J=20.0, 4.0 Hz, 1H), 2.59 (ddd, J=20.0, 4.0, 3.0 Hz, 1H), 2.83 (d, J=16.0 Hz, 1H), 4.04 (br s, 1H), 5.76 (br t, J=4.0 Hz, 1H), 5.99 (s, 1H); MS (FAB) m/z 247 (M+H)$^+$; [α]$_D$ −224° (c 0.5, CHCl$_3$).

Example C10

Substance PF1092C

Selenium dioxide (36 mg, 0.32 mmol) was suspended in a 97% aqueous 1,4-dioxane solution (0.6 ml), and the suspension was stirred at 105° C. for 30 min. The compound prepared in Example C9 (27 mg, 0.11 mmol) was added to the reaction solution, and a reaction was allowed to proceed at 105° C. for 21 hr. Thereafter, the reaction solution was diluted with ether, an aqueous sodium thiosulfate was added thereto, and the stirring was continued until the organic phase became transparent, followed by separation. The organic layer was concentrated under reduced pressure, and the concentrate was then purified by column chromatographic separation on silica gel (toluene:ethyl acetate=1:1) to give the title compound (a compound represented by the general formula (I) wherein R$^1$ and R$^2$ represent a hydrogen atom) (15 mg, 53%).

m.p.: 169–174° C. (decomp.), white acicular crystal (recrystallized from toluene).

$^1$H NMR (CDCl$_3$) δ 1.21 (s, 3H), 1.26 (d, J=7.0 Hz, 3H), 1.80 (dq, J=7.0, 1.5 Hz, 1H), 1.92 (br s, 3H), 2.19 (br d, J=16.0 Hz, 1H), 2.27 (d, J=3.0 Hz, 1H), 2.29 (d, J=8.0 Hz, 1H), 2.85 (d, J=16.0 Hz, 1H), 3.94 (ddd, J=5.0, 3.0, 1.5 Hz, 1H), 4.39 (ddd, J=8.0, 5.0, 2.0 Hz, 1H), 5.66 (br s, 1H), 5.99 (s, 1H); MS (EI) m/z 262 (M)$^+$; [α]$_D$ −97° (c 0.5, CHCl$_3$).

Example C11

Substance PF1092A

The compound prepared in Example C10 (19 mg, 0.07 mmol) was dissolved in anhydrous DMF (0.4 ml), imidazole (50 mg, 0.73 mmol) and t-butyldimethylsilyl chloride (65 mg, 0.43 mmol) were added to the solution, and the mixture was stirred at room temperature for 7 hr. Thereafter, the reaction solution was diluted with chloroform and washed with a 5% aqueous potassium hydrogensulfate solution and an aqueous sodium hydrogencarbonate solution in that order. The organic layer was dried over anhydrous sodium sulfate and then concentrated under reduced pressure. The concentrate was purified by preparative TLC separation (toluene:ethyl acetate=10:1) to give a corresponding t-butyldimethylsilyl form (23 mg, 85%).

The compound prepared just above (21 mg, 0.06 mmol) was dissolved in methylene chloride (0.45 ml), pyridine (22 μl, 0.27 mmol) and acetyl chloride (17 μl, 0.24 mmol) were added to the solution under ice cooling, the mixture was stirred under ice cooling for 30 min, the temperature was raised to room temperature, and the mixture was stirred at room temperature for additional 22 hr. The reaction solution was diluted with chloroform and washed with a 5% aqueous potassium hydrogensulfate solution and an aqueous sodium hydrogencarbonate solution in that order. The organic layer was dried over anhydrous sodium sulfate and then concentrated under reduced pressure. The concentrate was purified by preparative TLC separation (toluene:ethyl acetate=20:1) to give a corresponding acetyl form (21 mg, 89%).

The compound prepared just above (18 mg, 0.04 mmol) was dissolved in anhydrous THF (0.5 ml), hydrogen fluoride-pyridine complex (33 μl, 0.40 mmol) was added to the solution under ice cooling, the mixture was stirred under ice cooling for 30 min, the temperature was raised to room temperature, and the mixture was stirred for additional 2 hr. The reaction solution was diluted with chloroform and washed with a 5% aqueous potassium hydrogensulfate solution and an aqueous sodium hydrogencarbonate solution in that order. The organic layer was dried over anhydrous sodium sulfate and then concentrated under reduced pressure. The concentrate was purified by preparative TLC separation (hexane:ethyl acetate=1:1) to give the title compound (a compound represented by the general formula (I) wherein $R^1$ represents an acetyl group and $R^2$ represents a hydrogen atom) (5.5 mg, 42%).

Various spectral data of the title compound were in agreement with those of substance PF1092A disclosed in Japanese Patent Laid-Open No. 253467/1996.

Example C12

Substance PF1092B

The compound prepared in Example C10 (15 mg, 0.06 mmol) was dissolved in anhydrous methylene chloride (0.3 ml), diisopropylethylamine (25 μl, 0.14 mmol) and acetyl chloride (9 μl, 0.13 mmol) were added to the solution under ice cooling, the mixture was stirred under ice cooling for 30 min, the temperature was raised to room temperature, and the mixture was stirred for 17 hr. The reaction solution was diluted with chloroform and washed with a 5% aqueous potassium hydrogensulfate solution and an aqueous sodium hydrogencarbonate solution in that order. The organic layer was dried over anhydrous sodium sulfate and then concentrated under reduced pressure. The concentrate was purified by preparative TLC separation (hexane:ethyl acetate=1:1) to give the title compound (a compound represented by the general formula (I) wherein $R^1$ represents a hydrogen atom and $R^2$ represents an acetyl group) (7.8 mg, 45%).

Various spectral data of the title compound were in agreement with those of substance PF1092B disclosed in Japanese Patent Laid-Open No. 253467/1996.

Activity Evaluation Test

The progesterone receptor binding activity of the compounds of the present invention was measured in the following manner in accordance with the method of H. Kondo et. al. (J. Antibiotics, Vol. 43, pp. 1533–1542, 1990).

That is, uteri taken from hogs in 5 mM phosphate buffer were disrupted using Polytron homogenizer, and the resulting solution was centrifuged (100,000×g, 30 min) to separate the supernatant, thereby preparing a cytosol containing progesterone receptor. A given concentration of a test drug solution (10 μl) was added to a solution composed of 50 μl of the cytosol obtained just above (2–3 mg protein/ml) and 40 μl of a solution of [$^3$H]-progesterone as a ligand (3.84 TBq/mmol, 18.5 kBq/ml), and they were incubated in a test tube for 60 min at 4° C. to effect a reaction. Then, 100 μl of a 0.5% activated carbon solution was added to the reaction solution, and the mixture was allowed to stand for 10 min and then centrifuged (2,000×g, 10 min). The radioactivity of the supernatant was measured with a liquid scintillation counter.

Separately, the radioactivity was measured in the same manner as described above, except that no test drug was added. Further, the radioactivity was measured in the same manner as described above, except that 10 μl of Medroxyprogesterone Acetate (MPA) (10 μg/ml) was added instead of the test drug. The radioactivity with no test drug added was defined as the amount of total binding of [$^3$H]-progesterone to the cytosol, and the radioactivity with MPA added was defined as the amount of non-specific binding. The inhibition ratio was calculated from these measured values by the following equation to determine the binding inhibitory activity ($IC_{50}$).

$$\text{Inhibition ratio (\%)} = \left\{1 - \frac{(\text{total binding amount with test drug added}) - (\text{non-specific binding amount})}{(\text{total binding amount with no test drug added}) - (\text{non-specific binding amount})}\right\} \times 100$$

The compounds prepared in Examples A1, A3, A4, A6b, A7, A8, A10, A12, A17, A19, A21, A23, A30, A41, A44, and A45, the compounds prepared in Examples B2, B4, B7, B8, B27, B28, B30, and B42, and Mifepristone (RU38486) had the following inhibitory activity against progesterone receptor binding.

TABLE 1

Inhibitory activity against progesterone receptor binding

| Ex. No. of compound | Inhibitory activity ($IC_{50}$) (nM) |
|---|---|
| A3 | 12 |
| A17 | 17 |
| A23 | 18 |
| A21 | 27 |
| A45 | 29 |
| A4 | 32 |
| A19 | 47 |
| A30 | 47 |
| A10 | 75 |
| A12 | 83 |
| A8 | 97 |
| A44 | 276 |
| A6b | 288 |
| A41 | 400 |
| A1 | 1000 |
| A7 | 2840 |
| B2 | 55 |
| B4 | 53 |
| B7 | 54 |
| B8 (Racemic modification) | 74 |
| B8 (Natural type) | 21 |
| B27 | 39 |
| B28 | 66 |
| B30 | 60 |
| B42 (Nonnatural type) | 797 |
| B42 (Natural type) | 33 |
| RU38486 | 106 |

Example D1

A medium composed of 2.0% of starch, 1.0% of glucose, 0.5% of polypeptone, 0.6% of wheat germ, 0.3% of yeast extract, 0.2% of soybean meal and 0.2% of calcium carbonate (pH 7.0 before sterilization) was used as a seed culture medium. Another medium prepared by adding 0.3% of soybean meal to sufficiently water-absorbed rice was used as a prajuction medium.

A 20 ml portion of the seed culture medium dispensed in a 100 ml capacity conical flask was sterilized at 120° C. for 15 minutes, and one loopful of Penicillium sp. PF1092 (FERM BP-5350) cells grown on a slant agar medium were inocculated into the medium and cultured at 25° C. for 3 days on a shaker to obtain a seed culture. Next, a 100 g portion of the aforementioned production medium dispensed in a 500 ml capacity conical flask was sterilized at 120° C. for 15 minutes, and 5 ml of the just obtained seed culture was inoculated into the medium, mixed thoroughly and then subjeeted to 10 days of static culturing at 28° C.

Example D2

A 6 kg portion of the thus obtained culture mixture was extracted with 12 liters of ethyl acetate, and the resulting ethyl acetate layer containing active components was evaporated to obtain 15.3 g of oily material. The thus obtained oily material was applied to a column packed with 400 g of silica gel (Wakogel C-200, manutactured by Wako Pure Chemical Industries), washed with chloroform and then chromatographed using chloroform-methanol (100:1 to 100:3) as a developing solvent, and the resulting active fraction was evaporated to obtain 4.6 g of crude powder. Next, the crude powder was applied to a column packed with 150 g of silica gel (Wakogel C-200, manutactured by Wako Pure Chemical Industries), washed with hexane-ethyl acetate (8:1 to 5:1) and then chromatographed using hexane-ethyl to acetate (4:1 to 3:1) as a developing solvent to effect elution of substance PF1092B, and the resulting active fraction was evaporated to obtain 282 mg of crude powder containing substance PF1092B. The chromatography was continued using hexane-ethyl acetate (2:1 to 1:1) as a developing solvent to effect elution of substance PF1092A and substance PF1092C, and the resulting active fraction was evaporated to obtain 763 mg of crude powder containing substance PF1092A and substance PF1092C. Next, the crude powder containing substance PF1092B was purified by Sephadex LH-20 (700 ml, manutactured by Pharmacia) column chromatography using chloroform-methanol (1:1) as a developing solvent, and the active fraction containing substance PF1092B was evaporated to obtain 157.0 mg of substance PF1092B as colorless powder. The colorless powder of substance PF1092B was then dissolved in a chloroform-methanol mixture and allowed to stand to obtain 49.1 mg of substance PF1092B as colorless needle crystals.

On the other hand, the crude powder containing substance PF1092A and substance PF1092C obtained by the silica gel column chromatography using hexane-ethyl acetate (2:1 to 1:1) as a developing solvent was purified by Sepha-dex LH-20 (700 ml) column chromatography using chloroform-methanol (1:1) as a developing solvent to obtain 298 mg of substance PF1092A as colorless powder and then 159 mg of substance PF1092C as colorless powder. Thereafter, the colorless power of substance PF1092A was dissolved in a chloroform-methanol mixture and allowed to stand to obtain 60.0 mg of substance PF1092A as colorless needle crystals, and the colorless powder of substance PF1092C was dissolved in ethyl acetate and allowed to stand to obtain 30.1 mg of substance PF1092C as colorless needle crystals. These substances have the aforementioned physicochemical properties.

Structures of the compounds of the above examples are summarized in the following table.

TABLE 2

| Example | R$^1$ | R$^2$ | R$^3$ | R$^4$ | R$^5$ |
|---|---|---|---|---|---|
| A1 | C$_2$H$_5$CO—O— | HO— | H | CH$_3$ | H |
| A2 | HO— | C$_2$H$_5$CO—O— | H | CH$_3$ | H |
| A3 | HO— | 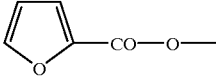 | H | CH$_3$ | H |
| A4 | C$_2$H$_5$CO—O— | C$_2$H$_5$CO—O— | H | CH$_3$ | H |
| A6a | C$_3$H$_7$NHCO—O— | HO— | H | CH$_3$ | H |
| A6b | HO— | C$_3$H$_7$NHCO—O— | H | CH$_3$ | H |
| A6c | C$_3$H$_7$NHCO—O— | C$_3$H$_7$NHCO—O— | H | CH$_3$ | H |
| A7 | 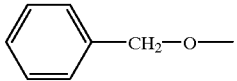 | HO— | H | CH$_3$ | H |
| A8 | CH$_3$OCH$_2$O— | 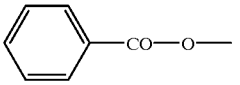 | H | CH$_3$ | H |
| A9 | HO— | 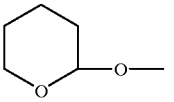 | H | CH$_3$ | H |
| A10 | CH$_3$O— | C$_2$H$_5$CO—O— | H | CH$_3$ | H |
| A11a | HO— | CH$_3$CONH— | H | CH$_3$ | H |
| A11b | HO— | CH$_3$CONH— | H | CH$_3$ | H |
| A12 | HO— | Cl—CH$_2$CO—O— | H | CH$_3$ | H |

TABLE 2-continued

| Example | R¹ | R² | R³ | R⁴ | R⁵ |
|---|---|---|---|---|---|
| A13 | HO— | 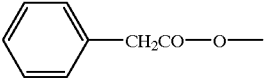PhCH₂CO—O— | H | CH₃ | H |
| A14 | C₂H₅CO—O— | 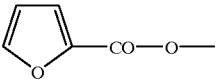furan-2-CO—O— | H | CH₃ | H |
| A15 | 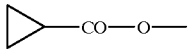cyclopropyl-CO—O— | C₂H₅CO—O— | H | CH₃ | H |
| A16 | HO— | (CH₃)₂CHCO—O— | H | CH₃ | H |
| A17 | HO— | 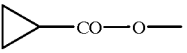cyclopropyl-CO—O— | H | CH₃ | H |
| A18 | 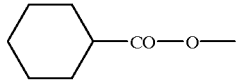cyclohexyl-CO—O— | HO— | H | CH₃ | H |
| A19 | HO— | 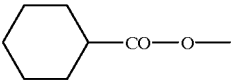cyclohexyl-CO—O— | H | CH₃ | H |
| A20 | HO— | 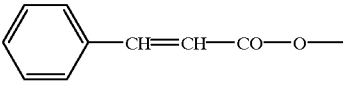Ph-CH=CH-CO—O— | H | CH₃ | H |
| A21 | HO— | 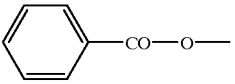Ph-CO—O— | H | CH₃ | H |
| A22 | 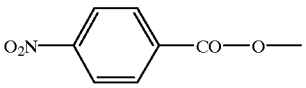O₂N-C₆H₄-CO—O— | HO— | H | CH₃ | H |
| A23 | HO— | 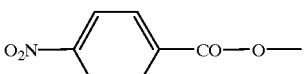O₂N-C₆H₄-CO—O— | H | CH₃ | H |
| A24 | 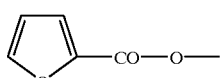furan-2-CO—O— | 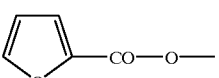furan-2-CO—O— | H | CH₃ | H |
| A25 | HO— | 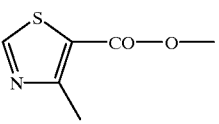4-methylthiazol-5-CO—O— | H | CH₃ | H |
| A26 | HO— | 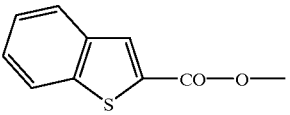benzothiophene-2-CO—O— | H | CH₃ | H |
| A27 | CH₃NHCO—O— | HO— | H | CH₃ | H |

TABLE 2-continued

| Example | R¹ | R² | R³ | R⁴ | R⁵ |
| --- | --- | --- | --- | --- | --- |
| A28 | C₆H₅-NHCO-O- | C₆H₅-NHCO-O- | H | CH₃ | H |
| A29 | CH₃-O- | CH₃-O- | H | CH₃ | H |
| A30 | CH₃-O- | CH₃-CO-O- | H | CH₃ | H |
| A31 | CH₃-O- | (2-furyl)-CO-O- | H | CH₃ | H |
| A32 | CH₃-O- | (2-thienyl)-CO-O- | H | CH₃ | H |
| A33 | C₃H₇O- | CH₃CO-O- | H | CH₃ | H |
| A34 | CH₃-O- | C₂H₅O-CO-O- | H | CH₃ | H |
| A35 | CH₃-O- | C₆H₅-O-CO-O- | H | CH₃ | H |
| A36 | C₂H₅CO-O- | CH₃-O-CH₂-O- | H | CH₃ | H |
| A37 | C₆H₅-CO-O- | CH₃-O-CH₂-O- | H | CH₃ | H |
| A38 | CH₃OC₂H₄OCH₂O- | C₆H₅-CO-O- | H | CH₃ | H |
| A39 | CH₃O- | (2-furyl)-CO-O- | H | CH₃ | H |
| A40 | C₂H₅O- | (2-furyl)-CO-O- | H | CH₃ | H |
| A41 | C₂H₅O- | (2-thienyl)-CO-O- | H | CH₃ | H |
| A42 | CH₃O- | CH₃O- | H | CH₃ | H |
| A43 | CH₃O- | CH₃SO₂-O- | H | CH₃ | H |
| A44 | CH₃CO-O- | (2-furyl)-CO-O- | H | CH₃ | H |
| A45 | HO- | (2-thienyl)-CO-O- | H | CH₃ | H |
| A46 | CH₃O- | CH₃CONH- | H | CH₃ | H |
| B1 | H | HO- | H | CH₃ | H |
| B2 | H | CH₃CO-O- | H | CH₃ | H |
| B3 | H | C₂H₅CO-O- | H | CH₃ | H |
| B4 | H | C₃H₇CO-O- | H | CH₃ | H |
| B5 | H | (CH₃)₂CHCO-O- | H | CH₃ | H |
| B6 | H | (CH₃)₂CHCH₂CO-O- | H | CH₃ | H |

TABLE 2-continued

| Example | R¹ | R² | R³ | R⁴ | R⁵ |
|---|---|---|---|---|---|
| B7 | H | phenyl-CO—O— | H | CH₃ | H |
| B8 | H | furan-2-yl-CO—O— | H | CH₃ | H |
| B9 | H | thiophen-2-yl-CO—O— | H | CH₃ | H |
| B13 | H | HO— | H | CH₃ | CH₃ |
| B14 | H | CH₃CO—O— | H | CH₃ | CH₃ |
| B15 | H | C₂H₅CO—O— | H | CH₃ | CH₃ |
| B16 | H | phenyl-CO—O— | H | CH₃ | CH₃ |
| B17 | H | furan-2-yl-CO—O— | H | CH₃ | CH₃ |
| B20 | H | HO— | H | C₂H₅ | H |
| B21 | H | CH₃CO—O— | H | C₂H₅ | H |
| B22 | H | C₂H₅CO—O— | H | C₂H₅ | H |
| B23 | H | phenyl-CO—O— | H | C₂H₅ | H |
| B24 | H | furan-2-yl-CO—O— | H | C₂H₅ | H |
| B26 | H | HO— | H | H | H |
| B27 | H | CH₃CO—O— | H | H | H |
| B28 | H | C₂H₅CO—O— | H | H | H |
| B29 | H | phenyl-CO—O— | H | H | H |
| B30 | H | furan-2-yl-CO—O— | H | H | H |
| B34 | H | HO— | CH₃ | H | H |
| B35 | H | CH₃CO—O— | CH₃ | H | H |
| B36 | H | C₂H₅CO—O— | CH₃ | H | H |
| B37 | H | phenyl-CO—O— | CH₃ | H | H |
| B38 | H | furan-2-yl-CO—O— | CH₃ | H | H |

TABLE 2-continued

| Example | R¹ | R² | R³ | R⁴ | R⁵ |
|---|---|---|---|---|---|
| B39 | HO— | HO— | H | CH₃ | H |
| B40 | HO— | HO— | H | CH₃ | CH₃ |
| B41 | HO— | HO— | H | C₂H₅ | H |
| B46 | CH₃ | HO— | H | CH₃ | H |
| B47 | CH₃ | CH₃CO—O— | H | CH₃ | H |
| B48 | CH₃ | C₂H₅CO—O— | H | CH₃ | H |
| B49 | CH₃ | 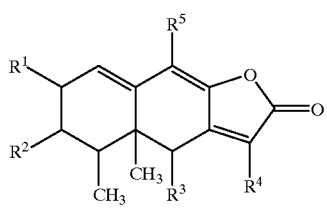 | H | CH₃ | H |
| B50 | CH₃ | 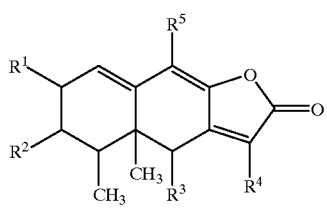 | H | CH₃ | H |

Preparation Tablets

The compound of Example A4, lactose, crosslinked polyvidone, hydroxypropylmethyl cellulose were granulated by the wet process, and magnesium stearate was added thereto.

The mixture was then compressed to prepare tablets. Each tablet had the following composition.

| | |
|---|---|
| Compound of Example A4 | 5.0 mg |
| Lactose | 185 mg |
| Crosslinked polyvidone | 7.0 mg |
| Hydroxypropylmethyl cellulose | 2.5 mg |
| Magnesium stearate | 0.5 mg |
| Total | 200 mg |

Acute Toxicity

The compound of Example A4 dissolved in 0.2% of methylcellulose solution was hypodermically administered to SD male rat (16 weeks old) at a dose of 60 mg/kg. As a result, all the animals survived and there is no significant toxicity.

What is claimed is:

1. A compound represented by the following formula (I) or a pharmaceutically acceptable salt thereof:

wherein
$R^1$ represents
a hydroxyl group,
optionally substituted $C_1$–$C_{10}$ alkyloxy,
optionally substituted $C_2$–$C_{10}$ alkenyloxy,
optionally substituted $C_2$–$C_{10}$ alkynyloxy,
$C_3$–$C_6$ cycloalkyloxy,
$C_2$–$C_{12}$ alkoxyalkyloxy,
five- or six-membered cycloalkyloxy containing one oxygen atom,
optionally substituted $C_7$–$C_{15}$ aralkyloxy,
optionally substituted $C_2$–$C_{11}$ alkylcarbonyloxy,
optionally substituted $C_3$–$C_{11}$ alkenylcarbonyloxy,
optionally substituted $C_3$–$C_{11}$ alkynylcarbonyloxy,
$C_4$–$C_{15}$ cycloalkylcarbonyloxy,
$C_2$–$C_{11}$ alkoxycarbonyloxy,
$C_7$–$C_{15}$ aryloxy carbonyloxy,
optionally substituted $C_8$–$C_{15}$ aralkylcarbonyloxy,
optionally substituted $C_7$–$C_{15}$ aromatic acyloxy,
optionally substituted $C_3$–$C_{15}$ heteroaromatic acyloxy having at least one hetero atom selected from the group consisting of nitrogen, oxygen, and sulfur atoms,
optionally substituted $C_4$–$C_{12}$ saturated heterocyclic carbonyloxy having at least one hetero atom selected from the group consisting of nitrogen, oxygen, and sulfur atoms,
$C_1$–$C_6$ alkylsulfonyloxy,
optionally substituted $C_6$–$C_{12}$ aromatic sulfonyloxy,
$C_2$–$C_7$ alkylcarbamoyloxy,
optionally substituted $C_7$–$C_{12}$ aromatic carbamoyloxy,
optionally substituted $C_2$–$C_{11}$ alkylcarbonylamino,
optionally substituted $C_7$–$C_{15}$ aromatic acylamino,
a hydrogen atom,
optionally substituted $C_1$–$C_{10}$ alkyl,
optionally substituted $C_2$–$C_{10}$ alkenyl, or
optionally substituted $C_2$–$C_{10}$ alkynyl;
$R^2$ represents
a hydroxyl group,
optionally substituted $C_1$–$C_{10}$ alkyloxy,
optionally substituted $C_2$–$C_{10}$ alkenyloxy,
optionally substituted $C_2$–$C_{10}$ alkynyloxy,
$C_3$–$C_6$ cycloalkyloxy,
$C_2$–$C_{12}$ alkoxyalkyloxy,
five- or six-membered cycloalkyloxy containing one oxygen atom,
optionally substituted $C_7$–$C_{15}$ aralkyloxy,
optionally substituted $C_2$–$C_{11}$ alkylcarbonyloxy,
optionally substituted $C_3$–$C_{11}$ alkenylcarbonyloxy,
optionally substituted $C_3$–$C_{11}$ alkynylcarbonyloxy,
$C_4$–$C_{15}$ cycloalkylcarbonyloxy,
$C_2$–$C_{11}$ alkoxycarbonyloxy,
$C_7$–$C_{15}$ aryloxy carbonyloxy,
optionally substituted $C_8$–$C_{15}$ aralkylcarbonyloxy,
optionally substituted $C_7$–$C_{15}$ aromatic acyloxy,
optionally substituted $C_3$–$C_{15}$ heteroaromatic acyloxy having at least one hetero atom selected from the group consisting of nitrogen, oxygen, and sulfur atoms, optionally substituted $C_4$–$C_{12}$ saturated heterocyclic carbonyloxy having at least one hetero atom selected from the group consisting of nitrogen, oxygen, and sulfur atoms, $C_1$–$C_6$ alkylsulfonyloxy, optionally substituted $C_6$–$C_{12}$ aromatic sulfonyloxy, $C_2$–$C_7$ alkylcarbamoyloxy, optionally substituted $C_7$–$C_{12}$ aromatic carbamoyloxy, optionally substituted $C_2$–$C_{11}$ alkylcarbonylamino, optionally substituted $C_7$–$C_{15}$ aromatic acylamino;

$R^3$ represents a hydrogen atom optionally substituted $C_1$–$C_{10}$ alkyl, or optionally substituted $C_2$–$C_{10}$ alkenyl;

$R^4$ represents a hydrogen atom optionally substituted $C_1$–$C_{10}$ alkyl, or optionally substituted $C_2$–$C_{10}$ alkenyl; and $R^5$ represents a hydrogen atom optionally substituted $C_1$–$C_{10}$ alkyl, or optionally substituted $C_2$–$C_{10}$ alkenyl, provided that a compound wherein both $R^1$ and $R^2$ represent a hydroxyl group, $R^3$ and $R^5$ represent a hydrogen atom, and $R^4$ represents methyl, a compound wherein $R^1$ represents methylcarbonyloxy, and $R^2$ represents a hydroxyl group, $R^3$ and $R^5$ represent a hydrogen atom, and $R^4$ represents methyl, a compound wherein $R^1$ represents a hydroxyl group, $R^2$ represents methylcarbonyloxy, $R^3$ and $R^5$ represent a hydrogen, and $R^4$ represents methyl, and a compound wherein $R^1$ represents a hydrogen atom, $R^2$ represents $C_{1-15}$ alkyloxy or $C_{2-5}$ alkylcarbonyloxy, $R^3$ represents a hydrogen atom, $R^4$ represents methyl, and $R^5$ represents a hydrogen atom, are excluded.

2. The compound according to claim 1, wherein $R^1$ represents a hydroxyl group, $C_1$–$C_{10}$ alkyloxy, $C_3$–$C_6$ cycloalkyloxy, $C_2$–$C_{12}$ alkoxyalkyloxy, optionally substituted $C_7$–$C_{15}$ aralkyloxy, optionally substituted $C_2$–$C_{11}$ alkylcarbonyloxy, $C_4$–$C_{15}$ cycloalkylcarbonyloxy, $C_2$–$C_{11}$ alkoxycarbonyloxy, $C_7$–$C_{15}$ aryloxy carbonyloxy, optionally substituted $C_8$–$C_{15}$ aralkylcarbonyloxy, optionally substituted $C_7$–$C_{15}$ aromatic acyloxy, optionally substituted $C_3$–$C_{15}$ heteroaromatic acyloxy having at least one hetero atom selected from the group consisting of nitrogen, oxygen, and sulfur atoms, optionally substituted $C_4$–$C_{12}$ saturated heterocyclic carbonyloxy having at least one hetero atom selected from the group consisting of nitrogen, oxygen, and sulfur atoms, $C_1$–$C_6$ alkylsulfonyloxy, $C_2$–$C_7$ alkylcarbamoyloxy optionally substituted $C_7$–$C_{12}$ aromatic carbamoyloxy, optionally substituted $C_2$–$C_{11}$ alkylcarbonylamino, a hydrogen atom, or optionally substituted $C_1$–$C_{10}$ alkyl;

$R^2$ represents a hydroxyl group;

$R^3$ represents a hydrogen atom or optionally substituted $C_1$–$C_{10}$ alkyl;

$R^4$ represents a hydrogen atom or optionally substituted $C_1$–$C_{10}$ alkyl; and $R^5$ represents a hydrogen atom or optionally substituted $C_1$–$C_{10}$ alkyl.

3. The compound according to claim 1, wherein $R^1$ represents a hydroxyl group;

$R^2$ represents a hydroxyl group, $C_1$–$C_{10}$ alkyloxy, $C_3$–$C_6$ cycloalkyloxy, $C_2$–$C_{12}$ alkoxyalkyloxy, optionally substituted $C_7$–$C_{15}$ aralkyloxy, optionally substituted $C_2$–$C_{11}$ alkylcarbonyloxy, $C_4$–$C_{15}$ cycloalkylcarbonyloxy, $C_2$–$C_{11}$ alkoxycarbonyloxy, $C_7$–$C_{15}$ aryloxy carbonyloxy, optionally substituted $C_8$–$C_{15}$ aralkylcarbonyloxy, optionally substituted $C_7$–$C_{15}$ aromatic acyloxy, optionally substituted $C_3$–$C_{15}$ heteroaromatic acyloxy having at least one hetero atom selected from the group consisting of nitrogen, oxygen, and sulfur atoms, optionally substituted $C_4$–$C_{12}$ saturated heterocyclic carbonyloxy having at least one hetero atom selected from the group consisting of nitrogen, oxygen, and sulfur atoms, $C_1$–$C_6$ alkylsulfonyloxy, $C_2$–$C_7$ alkylcarbamoyloxy optionally substituted $C_7$–$C_{12}$ aromatic carbamoyloxy, optionally substituted $C_2$–$C_{11}$ alkylcarbonylamino, a hydrogen atom, or optionally substituted $C_1$–$C_{10}$ alkyl;

$R^3$ represents a hydrogen atom or optionally substituted $C_1$–$C_{10}$ alkyl;

$R^4$ represents a hydrogen atom or optionally substituted $C_1$–$C_{10}$ alkyl; and $R^5$ represents a hydrogen atom or optionally substituted $C_1$–$C_{10}$ alkyl.

4. The compound according to claim 1, wherein $R^1$ and $R^2$ each independently represent a hydroxyl group;

$C_1$–$C_{10}$ alkyloxy, $C_3$–$C_6$ cycloalkyloxy, $C_2$–$C_{12}$ alkoxyalkyloxy, optionally substituted $C_7$–$C_{15}$ aralkyloxy, optionally substituted $C_2$–$C_{11}$ alkylcarbonyloxy, $C_4$–$C_{15}$ cycloalkylcarbonyloxy, $C_2$–$C_{11}$ alkoxycarbonyloxy, $C_7$–$C_{15}$ aryloxy carbonyloxy, optionally substituted $C_8$–$C_{15}$ aralkylcarbonyloxy, optionally substituted $C_7$–$C_{15}$ aromatic acyloxy, optionally substituted $C_3$–$C_{15}$ heteroaromatic acyloxy having at least one hetero atom selected from the group consisting of nitrogen, oxygen, and sulfur atoms, optionally substituted $C_4$–$C_{12}$ saturated heterocyclic carbonyloxy having at least one hetero atom selected from the group consisting of nitrogen, oxygen, and sulfur atoms,
$C_1$–$C_6$ alkylsulfonyloxy,
$C_2$–$C_7$ alkylcarbamoyloxy
optionally substituted $C_7$–$C_{12}$ aromatic carbamoyloxy,
optionally substituted $C_2$–$C_{11}$ alkylcarbonylamino,
a hydrogen atom, or
optionally substituted $C_1$–$C_{10}$ alkyl;
$R^3$ represents
a hydrogen atom or
optionally substituted $C_1$–$C_{10}$ alkyl;
$R^4$ represents
a hydrogen atom or
optionally substituted $C_1$–$C_{10}$ alkyl; and
$R^5$ represents
a hydrogen atom or
optionally substituted $C_1$–$C_{10}$ alkyl.

5. The compound according to claim 1, wherein
$R^1$ represents a hydrogen atom;
$R^2$ represents
a hydroxyl group,
$C_2$–$C_{10}$ alkylcarbonyloxy,
$C_3$–$C_{10}$ alkenylcarbonyloxy,
optionally substituted $C_2$–$C_{10}$ alkylcarbonyloxy,
$C_4$–$C_{15}$ cycloalkylcarbonyloxy,
optionally substituted $C_8$–$C_{15}$ aralkylcarbonyloxy,
optionally substituted $C_7$–$C_{15}$ aromatic acyloxy, or
optionally substituted $C_3$–$C_{15}$ heteroaromatic acyloxy having at least one nitrogen, oxygen, or sulfur atom;
$R^3$ represents
a hydrogen atom
optionally substituted $C_1$–$C_{10}$ alkyl, or
optionally substituted $C_2$–$C_{10}$ alkenyl;
$R^4$ represents
a hydrogen atom,
$C_1$–$C_{10}$ alkyl,
optionally substituted $C_1$–$C_{10}$ alkyl,
optionally substituted $C_2$–$C_{10}$ alkenyl; and
$R^5$ represents
a hydrogen atom
optionally substituted $C_1$–$C_{10}$ alkyl, or
optionally substituted $C_2$–$C_{10}$ alkenyl.

6. The compound according to claim 1, wherein
$R^2$ represents 2-tetrahydropyranyloxy, propionyloxy, isobutyryloxy, chloroacetyloxy, phenylacetyloxy, cyclopropylcarbonyloxy, cyclohexylcarbonyloxy, cinnamoyloxy, benzoyloxy, 4-nitrobenzoyloxy, 2-thenoyloxy, 2-furoyloxy, 1-benzothiophen-2-ylcarbonyloxy, 4-methyl-5-thiazolylcarbonyloxy, n-propylcarbamoyloxy, or acetylamino, and
$R^1$ represents a hydroxyl group.

7. The compound according to claim 1, wherein
$R^2$ represents methoxy, acetyloxy, propionyloxy, cyclopropylcarbonyloxy, benzoyloxy, 2-thenoyloxy, 2-furoyloxy, ethoxycarbonyloxy, phenoxycarbonyloxy, methylsulfonyloxy, or acetylamino; and
$R^1$ represents methoxy.

8. The compound according to claim 1, wherein
$R^2$ represents acetyloxy, propionyloxy, cyclopropylcarbonyloxy, benzoyloxy, 2-thenoyloxy, or 2-furoyloxy; and
$R^1$ represents ethoxy.

9. The compound according to claim 1, wherein
$R^2$ represents acetyloxy, propionyloxy, cyclopropylcarbonyloxy, benzoyloxy, 2-thenoyloxy, or 2-furoyloxy; and
$R^1$ represents n-propyloxy.

10. The compound according to claim 1, wherein
$R^2$ represents a hydroxyl group, acetyloxy, propionyloxy, cyclopropylcarbonyloxy, benzoyloxy, 2-furoyloxy, 2-thenoyloxy, or methoxymethyloxy; and
$R^1$ represents propionyloxy.

11. The compound according to claim 1, wherein
$R^2$ represents a hydroxyl group,
$R^1$ represents benzyloxy, cyclopropylcarbonyloxy, cyclohexylcarbonyloxy, benzoyloxy, 4-nitrobenzoyloxy, 2-thenoyloxy, 2-furoyloxy, methylcarbamoyloxy, or n-propylcarbamoyloxy.

12. The compound according to claim 1, wherein
$R^2$ represents 2-furoyloxy; and
$R^1$ represents acetyloxy, cyclopropylcarbonyloxy, benzoyloxy, 2-thenoyloxy, or 2-furoyloxy.

13. The compound according to claim 1, wherein
$R^2$ represents propionyloxy; and
$R^1$ represents acetyloxy, cyclopropylcarbonyloxy, benzoyloxy, 2-thenoyloxy, or 2-furoyloxy.

14. The compound according to claim 1, wherein
$R^2$ represents benzoyloxy; and
$R^1$ represents methoxymethyloxy or methoxyethoxymethyloxy.

15. The compound according to claim 1, wherein
$R^2$ represents methoxymethyloxy; and
$R^1$ represents benzoyloxy.

16. The compound according to claim 1, wherein
$R^2$ represents n-propylcarbamoyloxy; and
$R^1$ represents n-propylcarbamoyloxy.

17. The compound according to claim 1, wherein
$R^2$ represents phenylcarbamoyloxy; and
$R^1$ represents phenylcarbamoyloxy.

18. The compound according to claim 1, wherein
$R^1$ represents a hydrogen atom;
$R^2$ represents a hydroxyl atom, acetyloxy, propionyloxy, butyryloxy, isobutyryloxy, isovaleryloxy, benzoyloxy, 2-furoyloxy, or 2-thenoyloxy;
$R^3$ represents a hydrogen atom;
$R^4$ represents methyl; and
$R^5$ represents a hydrogen atom.

19. The compound according to claim 1, wherein
$R^1$ represents a hydrogen atom;
$R^2$ represents a hydroxyl group, acetyloxy, propionyloxy, butyryloxy, isobutyryloxy, isovaleryloxy, benzoyloxy, 2-furoyloxy, or 2-thenoyloxy;

$R^3$ represents a hydrogen atom;
$R^4$ represents methyl; and
$R^5$ represents methyl.

20. The compound according to claim 1, wherein
$R^1$ represents a hydrogen atom;
$R^2$ represents a hydroxyl group, acetyloxy, propionyloxy, butyryloxy, isobutyryloxy, isovaleryloxy, benzoyloxy, 2-furoyloxy, or 2-thenoyloxy;
$R^3$ represents a hydrogen atom;
$R^4$ represents ethyl; and
$R^5$ represents a hydrogen atom.

21. The compound according to claim 1, wherein
$R^1$ represents a hydrogen atom;
$R^2$ represents a hydroxyl group, acetyloxy, propionyloxy, butyryloxy, isobutyryloxy, isovaleryloxy, benzoyloxy, 2-furoyloxy, or 2-thenoyloxy;
$R^3$ represents a hydrogen atom;
$R^4$ represents a hydrogen atom; and
$R^5$ represents a hydrogen atom.

22. The compound according to claim 1, wherein
$R^1$ represents a hydrogen atom;
$R^2$ represents a hydroxyl group, acetyloxy, propionyloxy, butyryloxy, isobutyryloxy, isovaleryloxy, benzoyloxy, 2-furoyloxy, or 2-thenoyloxy;
$R^3$ represents methyl;
$R^4$ represents methyl; and
$R^5$ represents a hydrogen atom.

23. The compound according to claim 1, wherein
$R^1$ represents methyl;
$R^2$ represents a hydroxyl group, acetyloxy, propionyloxy, butyryloxy, isobutyryloxy, isovaleryloxy, benzoyloxy, 2-furoyloxy, or 2-thenoyloxy;
$R^3$ represents a hydrogen atom;
$R^4$ represents methyl; and
$R^5$ represents a hydrogen atom.

24. The compound according to claim 1, wherein
$R^1$ and $R^2$ each independently represent
a hydroxyl group,
optionally substituted $C_1$–$C_{10}$ alkyloxy,
optionally substituted $C_2$–$C_{10}$ alkenyloxy,
optionally substituted $C_2$–$C_{10}$ alkynyloxy,
$C_3$–$C_6$ cycloalkyloxy,
$C_2$–$C_{12}$ alkoxyalkyloxy,
five- or six-membered cycloalkyloxy containig one oxygen atom,
optionally substituted $C_7$–$C_{15}$ aralkyloxy,
optionally substituted $C_2$–$C_{11}$ alkylcarbonyloxy,
optionally substituted $C_3$–$C_{11}$ alkenylcarbonyloxy,
optionally substituted $C_3$–$C_{11}$ alkynylcarbonyloxy,
$C_4$–$C_{15}$ cycloalkylcarbonyloxy,
$C_2$–$C_{11}$ alkoxycarbonyloxy,
$C_7$–$C_{15}$ aryloxy carbonyloxy,
optionally substituted $C_8$–$C_{15}$ aralkylcarbonyloxy,
optionally substituted $C_7$–$C_{15}$ aromatic acyloxy,
optionally substituted $C_3$–$C_{15}$ heteroaromatic acyloxy having at least one hetero atom selected from the group consisting of nitrogen, oxygen, and sulfur atoms,
optionally substituted $C_4$–$C_{12}$ saturated heterocyclic carbonyloxy having at least one hetero atom selected from the group consisting of nitrogen, oxygen, and sulfur atoms,
$C_1$–$C_6$ alkylsulfonyloxy,
optionally substituted $C_6$–$C_{12}$ aromatic sulfonyloxy,
$C_2$–$C_7$ alkylcarbamoyloxy
optionally substituted $C_7$–$C_{12}$ aromatic carbamoyloxy,
optionally substituted $C_2$–$C_{11}$ alkylcarbonylamino;
$R^3$ represents a hydrogen atom;
$R^4$ represents
a hydrogen atom or
$C_1$–$C_{10}$ alkyl; and
$R^5$ represents a hydrogen atom.

25. The compound according to claim 2, wherein
$R^1$ and $R^2$ each independently represent
a hydroxyl group,
$C_1$–$C_6$ alkyloxy group,
$C_2$–$C_{12}$ alkoxyalkyloxy which may be substituted by $C_1$–$C_6$ alkoxy group,
$C_7$–$C_{15}$ aralkyloxy,
$C_2$–$C_7$ alkylcarbonyloxy which may be substituted by a halogen,
$C_4$–$C_{15}$ cycloalkylcarbonyloxy,
$C_2$–$C_7$ alkoxycarbonyloxy,
$C_7$–$C_{15}$ aryloxycarbonyloxy,
$C_8$–$C_{15}$ aralkylcarbonyloxy,
$C_7$–$C_{15}$ arylcarbonyloxy which may be substituted by nitro,
five- or six-membered heteroaromatic acyloxy containing one oxygen or sulfur atom,
five- or six-membered heteroaromatic acyloxy, containing an nitrogen or sulfur atom, which may be substituted by $C_1$–$C_6$ alkyl,
five- or six-membered saturated heterocyclic carbonyloxy having at least one hetero atom selected from nitrogen, oxygen, and sulfur atoms,
$C_1$–$C_6$ alkylsulfonyloxy,
$C_2$–$C_7$ alkylcarbamoyloxy,
$C_7$–$C_{12}$ arylcarbamoyloxy,
$C_2$–$C_7$ alkylcarbonylamino:
$R^3$ represents a hydrogen atom;
$R^4$ represents $C_1$–$C_6$ alkyl; and
$R^5$ represents a hydrogen atom.

26. A pharmaceutical composition comprising as an active ingredient the compound according to claim 1.

27. The pharmaceutical composition according to claim 26, which is a therapeutic or prophylactic agent for progesterone-related diseases.

28. The pharmaceutical composition according to claim 26, which is an abortifacient, an oral contraceptive pill, an carcinostatic agent for breast cancer or ovarian cancer, a therapeutic agent for endometriosis, meningioma, or myeloma, or a therapeutic or prophylactic agent for osteoporosis or climacteric disturbance.

29. A method for treating or preventing progesterone-related diseases, comprising administering the compound according to claim 1 to a mammal.

30. A method for treating or preventing abortion, contraception, breast or ovarian cancer, endometriosis, meningioma, myeloma, osteoporosis, or climacteric disturbance, comprising administering the compound according to claim 1 to a mammal.

31. A process for producing a compound represented by the formula (I) according to claim 1, wherein $R^1$ and $R^2$ represent a hydroxyl group, $R^3$ represents a hydrogen atom, $R^4$ represents a hydrogen atom, optionally substituted $C_1$–$C_{10}$ alkyl, or $C_2$–$C_{10}$ alkenyl and $R^5$ represents a hydrogen atom, said process comprising the steps of:

(a) oxidizing the following compound (11):

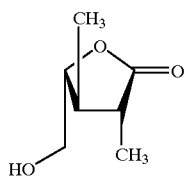
(11)

and then conducting acetal protection;

(b) reacting the resultant compound (12):

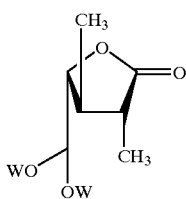
(12)

wherein W is a protective group of an acetal group, with benzenesulfonylmethyl in the presence of a base;

(c) protecting the resultant compound (13):

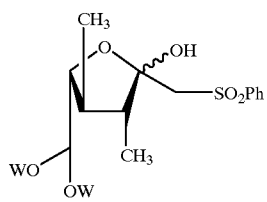
(13)

with a hydroxyl group and then conducting a ring-opening reaction in the presence of a base;

(d) subjecting the resultant compound (14):

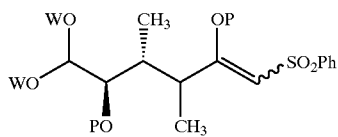
(14)

to a ring-closing reaction with a Lewis acid;

(e) reducing the resultant compound (15):

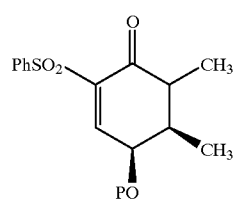
(15)

(f) subjecting the resultant compound (16):

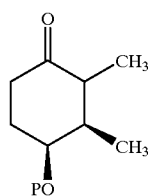
(16)

and 3-trimethylsilyl-3-buten-2-one to Michael addition and cyclocondensation in the presence of a base;

(g) condensing the resultant compound (17):

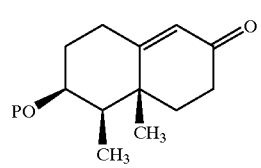
(17)

with α-keto ester by aldol condensation in the presence of a base and optionally a catalytic amount of zinc chloride;

(h) heating the resultant compound (18):

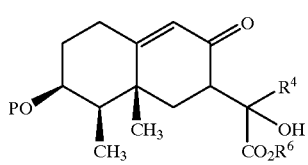
(18)

wherein $R^4$ is as defined above in connection with the formula (I) and $R^6$ is as defined above, under reflux in the presence of an acid catalyst;

(i) oxidizing the resultant compound (19):

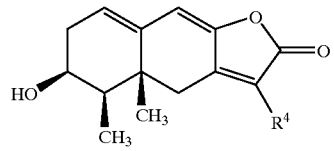
(19)

32. A method for the production of the compound according to claim 1 which comprises employing as a reactant, the compound:

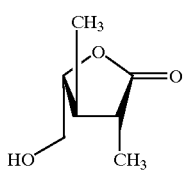

* * * * *